United States Patent
Wahr et al.

(10) Patent No.: US 7,654,978 B2
(45) Date of Patent: Feb. 2, 2010

(54) EMBOLI PROTECTION DEVICES AND RELATED METHODS OF USE

(75) Inventors: Dennis W. Wahr, Ann Arbor, MI (US); Thomas V. Ressemann, St. Cloud, MN (US); Peter T. Keith, St. Paul, MN (US); David J. Blaeser, Champlin, MN (US); Michael Berman, Minnetonka, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 11/034,824

(22) Filed: Jan. 14, 2005

(65) Prior Publication Data

US 2005/0131447 A1  Jun. 16, 2005

Related U.S. Application Data

(62) Division of application No. 09/845,162, filed on May 1, 2001, now Pat. No. 7,422,579.

(51) Int. Cl.
*A61M 29/00* (2006.01)
(52) U.S. Cl. .................. 604/101.01; 604/96.01
(58) Field of Classification Search ............ 604/101.01, 604/101.04, 101.02, 103.04, 96.01, 103.07; 606/194
See application file for complete search history.

(56) References Cited

U.S. PATENT DOCUMENTS

| | | | |
|---|---|---|---|
| 4,655,746 A | 4/1987 | Daniels et al. | |
| 4,696,668 A | * | 9/1987 | Wilcox .................. 604/28 |

(Continued)

FOREIGN PATENT DOCUMENTS

EP  0 427 429 A2  5/1991

(Continued)

OTHER PUBLICATIONS

Hurst, Robert W., MD, "Carotid Angioplasty," *Radiology*, vol. 201, No. 3, Dec. 1996, pp. 613-616.

(Continued)

*Primary Examiner*—Nicholas D Lucchesi
*Assistant Examiner*—Christopher D Koharski
(74) *Attorney, Agent, or Firm*—O'Melveny & Myers LLP

(57) ABSTRACT

An evacuation sheath assembly and method of treating occluded vessels which reduces the risk of distal embolization during vascular interventions is provided. The evacuation sheath assembly includes an elongated tube defining an evacuation lumen having proximal and distal ends. A proximal sealing surface is provided on a proximal portion of the tube and is configured to form a seal with a lumen of a guided catheter. A distal sealing surface is provided on a distal portion of the tube and is configured to form a seal with a blood vessel. A method of treatment of a blood vessel using the evacuation sheath assembly includes advancing the evacuation sheath assembly into the blood vessel through a guide catheter. Prior to advancing a device across a stenosis to be treated, normal antegrade blood flow in the blood vessel proximate to the stenosis is stopped. While blood flow is stopped, the stenosis is treated. Retrograde blood flow is induced within the blood vessel to carry embolic material dislodged during treating into the evacuation sheath assembly.

15 Claims, 48 Drawing Sheets

U.S. PATENT DOCUMENTS

| | | |
|---|---|---|
| 4,784,636 A | 11/1988 | Rydell |
| 4,883,460 A | 11/1989 | Zanetti |
| 4,921,478 A | 5/1990 | Solano et al. |
| 5,011,488 A | 4/1991 | Ginsburg |
| 5,059,178 A | 10/1991 | Ya |
| 5,074,845 A * | 12/1991 | Miraki et al. .......... 604/103.08 |
| 5,108,414 A | 4/1992 | Enderle et al. |
| 5,219,355 A | 6/1993 | Parodi et al. |
| 5,250,060 A | 10/1993 | Carbo et al. |
| 5,324,260 A | 6/1994 | O'Neill |
| 5,350,395 A | 9/1994 | Yock |
| 5,368,566 A | 11/1994 | Crocker |
| 5,385,562 A | 1/1995 | Adams et al. |
| 5,395,333 A * | 3/1995 | Brill ..................... 604/101.05 |
| 5,423,742 A | 6/1995 | Theron |
| 5,451,207 A | 9/1995 | Yock |
| 5,451,233 A | 9/1995 | Yock |
| 5,453,099 A | 9/1995 | Lee et al. |
| 5,466,222 A | 11/1995 | Ressemann |
| 5,484,412 A | 1/1996 | Pierpont |
| 5,514,092 A * | 5/1996 | Forman et al. ......... 604/101.03 |
| 5,527,292 A | 6/1996 | Adams et al. |
| 5,533,987 A | 7/1996 | Pray et al. |
| 5,536,242 A | 7/1996 | Willard |
| 5,569,204 A | 10/1996 | Cramer |
| 5,573,508 A | 11/1996 | Thornton |
| 5,643,208 A | 7/1997 | Parodi |
| 5,709,701 A | 1/1998 | Parodi |
| 5,716,340 A * | 2/1998 | Schweich et al. ...... 604/101.05 |
| 5,749,888 A | 5/1998 | Yock |
| 5,769,868 A | 6/1998 | Yock |
| 5,779,721 A | 7/1998 | Nash |
| 5,797,949 A | 8/1998 | Parodi |
| 5,820,595 A | 10/1998 | Parodi |
| 5,833,644 A | 11/1998 | Zadno-Azizi |
| 5,833,650 A | 11/1998 | Imran |
| 5,843,022 A | 12/1998 | Willard et al. |
| 5,868,706 A | 2/1999 | Cox |
| 5,879,361 A | 3/1999 | Nash |
| 5,891,090 A | 4/1999 | Thornton |
| 5,938,672 A | 8/1999 | Nash |
| 5,951,514 A * | 9/1999 | Sahota .................. 604/101.05 |
| 5,971,938 A | 10/1999 | Hart et al. |
| 5,989,263 A | 11/1999 | Shmulewitz |
| 5,997,558 A | 12/1999 | Nash |
| 6,007,545 A | 12/1999 | Venturelli |
| 6,013,085 A | 1/2000 | Howard |
| 6,022,336 A | 2/2000 | Zadno-Azizi et al. |
| 6,030,362 A * | 2/2000 | Boussignac et al. .... 604/101.01 |
| 6,036,715 A | 3/2000 | Yock |
| 6,042,605 A | 3/2000 | Martin et al. |
| 6,080,170 A | 6/2000 | Nash |
| 6,117,124 A | 9/2000 | Parodi |
| 6,126,635 A | 10/2000 | Simpson et al. |
| 6,135,991 A | 10/2000 | Muni et al. |
| 6,146,370 A | 11/2000 | Barbut |
| 6,152,909 A | 11/2000 | Bagaoisan et al. |
| 6,156,005 A | 12/2000 | Theron |
| 6,159,195 A | 12/2000 | Ha et al. |
| 6,176,844 B1 | 1/2001 | Lee |
| 6,206,868 B1 | 3/2001 | Parodi |
| 6,228,072 B1 | 5/2001 | Omaleki et al. |
| 6,231,588 B1 | 5/2001 | Zadno-Azizi |
| 6,270,477 B1 | 8/2001 | Bagaoisan et al. |
| 6,295,989 B1 | 10/2001 | Connors, III |
| 6,312,407 B1 | 11/2001 | Zadno-Azizi et al. |
| 6,355,016 B1 | 3/2002 | Bagaoisan et al. |
| 6,361,637 B2 | 3/2002 | Martin et al. |
| 6,398,773 B1 | 6/2002 | Bagaoisan et al. |
| 6,413,235 B1 | 7/2002 | Parodi |
| 6,423,032 B2 | 7/2002 | Parodi |
| 6,454,741 B1 | 9/2002 | Muni et al. |
| 6,485,500 B1 | 11/2002 | Kokish |
| 6,497,670 B1 | 12/2002 | Parodi |
| 6,520,986 B2 | 2/2003 | Martin et al. |
| 6,524,323 B1 | 2/2003 | Nash |
| 6,533,800 B1 | 3/2003 | Barbut |
| 6,540,712 B1 | 4/2003 | Parodi et al. |
| 6,544,276 B1 | 4/2003 | Azizi |
| 6,569,147 B1 | 5/2003 | Evans |
| 6,569,148 B2 | 5/2003 | Bagaoisan et al. |
| 6,582,396 B1 | 6/2003 | Parodi |
| 6,589,264 B1 | 7/2003 | Barbut et al. |
| 6,592,546 B1 | 7/2003 | Barbut et al. |
| 6,592,557 B2 | 7/2003 | Barbut et al. |
| 6,595,980 B1 | 7/2003 | Barbut |
| 6,605,074 B2 | 8/2003 | Zadno-Azizi et al. |
| 6,605,102 B1 | 8/2003 | Mazzocchi et al. |
| 6,623,471 B1 | 9/2003 | Barbut |
| 6,626,886 B1 | 9/2003 | Barbut |
| 6,632,236 B2 | 10/2003 | Hogendijk |
| 6,635,029 B1 | 10/2003 | Venturelli |
| 6,635,046 B1 | 10/2003 | Barbut |
| 6,645,222 B1 | 11/2003 | Parodi et al. |
| 6,652,480 B1 | 11/2003 | Imran et al. |
| 6,652,546 B1 | 11/2003 | Nash |
| 6,682,505 B2 | 1/2004 | Bates et al. |
| 6,682,543 B2 | 1/2004 | Barbut et al. |
| 6,712,806 B2 | 3/2004 | St. Germain et al. |
| 6,733,474 B2 | 5/2004 | Kusleika |
| 6,743,196 B2 | 6/2004 | Barbut et al. |
| 6,786,888 B1 | 9/2004 | Zadno-Azizi et al. |
| 6,790,204 B2 | 9/2004 | Zadno-Azizi et al. |
| 6,805,692 B2 | 10/2004 | Muni et al. |
| 6,827,701 B2 | 12/2004 | MacMahon et al. |
| 6,830,577 B2 | 12/2004 | Nash |
| 6,830,579 B2 | 12/2004 | Barbut |
| 6,837,881 B1 | 1/2005 | Barbut |
| 6,840,949 B2 | 1/2005 | Barbut |
| 6,843,797 B2 | 1/2005 | Nash |
| 6,849,068 B1 | 2/2005 | Bagaoisan et al. |
| 6,855,136 B2 | 2/2005 | Dorros et al. |
| 6,878,128 B2 | 4/2005 | MacMahon et al. |
| 6,887,220 B2 | 5/2005 | Hogendijk |
| 6,887,227 B1 | 5/2005 | Barbut |
| 6,896,663 B2 | 5/2005 | Barbut |
| 6,902,540 B2 | 6/2005 | Dorros et al. |
| 6,905,490 B2 | 6/2005 | Parodi |
| 6,905,505 B2 | 6/2005 | Nash |
| 6,908,474 B2 | 6/2005 | Hogendijk et al. |
| 6,936,056 B2 | 8/2005 | Nash |
| 2001/0012951 A1 | 8/2001 | Bates |
| 2001/0037085 A1 | 11/2001 | Keith et al. |
| 2001/0044598 A1 | 11/2001 | Parodi |
| 2001/0047184 A1 | 11/2001 | Connors, III |
| 2001/0049550 A1 | 12/2001 | Martin et al. |
| 2002/0002397 A1 | 1/2002 | Martin et al. |
| 2002/0016564 A1 | 2/2002 | Courtney et al. |
| 2002/0016565 A1 | 2/2002 | Zadno-Azizi et al. |
| 2002/0022859 A1 | 2/2002 | Hogendijk |
| 2002/0026145 A1 | 2/2002 | Bagaoisan et al. |
| 2002/0029031 A1 | 3/2002 | Bagaoisan et al. |
| 2002/0035347 A1 | 3/2002 | Bagaoisan et al. |
| 2002/0052638 A1 | 5/2002 | Zadno-Azizi |
| 2002/0062119 A1 | 5/2002 | Zadno-Azizi |
| 2002/0065507 A1 | 5/2002 | Zadno-Azizi |
| 2002/0087119 A1 | 7/2002 | Parodi |
| 2002/0091407 A1 | 7/2002 | Zadno-Azizi et al. |
| 2002/0107479 A1 | 8/2002 | Bates et al. |
| 2002/0151922 A1 | 10/2002 | Hogendijk et al. |
| 2002/0161395 A1 | 10/2002 | Douk et al. |
| 2002/0173815 A1 | 11/2002 | Hogendijk et al. |
| 2002/0177800 A1 | 11/2002 | Bagaoisan et al. |
| 2002/0188314 A1 | 12/2002 | Anderson et al. |

| | | | |
|---|---|---|---|
| 2003/0009146 A1 | 1/2003 | Muni et al. | |
| 2003/0023200 A1 | 1/2003 | Barbut et al. | |
| 2003/0023204 A1 | 1/2003 | Vo et al. | |
| 2003/0023227 A1 | 1/2003 | Zadno-Azizi et al. | |
| 2003/0040694 A1 | 2/2003 | Dorros et al. | |
| 2003/0040704 A1 | 2/2003 | Dorros et al. | |
| 2003/0040705 A1 | 2/2003 | Dorros et al. | |
| 2003/0040762 A1 | 2/2003 | Dorros et al. | |
| 2003/0055398 A1 | 3/2003 | Imran | |
| 2003/0069549 A1 | 4/2003 | MacMahon et al. | |
| 2003/0083617 A1 | 5/2003 | St. Germain et al. | |
| 2003/0097036 A1 | 5/2003 | St. Germain et al. | |
| 2003/0150821 A1 | 8/2003 | Bates et al. | |
| 2003/0158518 A1 | 8/2003 | Schonholz et al. | |
| 2003/0171769 A1 | 9/2003 | Barbut | |
| 2003/0171770 A1 | 9/2003 | Kusleika et al. | |
| 2003/0171771 A1 | 9/2003 | Anderson et al. | |
| 2003/0187390 A1 | 10/2003 | Bates et al. | |
| 2003/0187391 A1 | 10/2003 | Hogendijk | |
| 2003/0187392 A1 | 10/2003 | Hogendijk | |
| 2003/0191434 A1 | 10/2003 | Dorros et al. | |
| 2003/0208222 A1 | 11/2003 | Zadno-Azizi | |
| 2003/0233117 A1 | 12/2003 | Adams et al. | |
| 2004/0010280 A1 | 1/2004 | Adams et al. | |
| 2004/0010282 A1 | 1/2004 | Kusleika | |
| 2004/0015150 A1 | 1/2004 | Zadno-Azizi | |
| 2004/0019310 A1 | 1/2004 | Hogendijk | |
| 2004/0034366 A1 | 2/2004 | van der Burg et al. | |
| 2004/0054347 A1 | 3/2004 | Zadno-Azizi et al. | |
| 2004/0054348 A1 | 3/2004 | Hogendijk | |
| 2004/0064092 A1 | 4/2004 | Tsugita et al. | |
| 2004/0092869 A1 | 5/2004 | Venturelli | |
| 2004/0127885 A1 | 7/2004 | Barbut | |
| 2004/0193099 A1 | 9/2004 | MacMahon et al. | |
| 2004/0260239 A1 | 12/2004 | Kusleika | |
| 2005/0004517 A1 | 1/2005 | Courtney et al. | |
| 2005/0004594 A1 | 1/2005 | Nool et al. | |
| 2005/0010247 A1 | 1/2005 | Kusleika et al. | |
| 2005/0020973 A1 | 1/2005 | MacMahon et al. | |
| 2005/0085769 A1 | 4/2005 | MacMahon et al. | |
| 2005/0090854 A1 | 4/2005 | Barbut | |
| 2005/0124849 A1 | 6/2005 | Barbut et al. | |
| 2005/0124973 A1 | 6/2005 | Dorros et al. | |
| 2005/0131453 A1 | 6/2005 | Parodi | |
| 2005/0149112 A1 | 7/2005 | Barbut | |
| 2005/0154298 A1 | 7/2005 | Barbut | |
| 2005/0159640 A1 | 7/2005 | Barbut et al. | |

FOREIGN PATENT DOCUMENTS

| | | |
|---|---|---|
| WO | WO 97/42879 | 11/1997 |
| WO | WO 97/44082 | 11/1997 |
| WO | WO 98/38929 | 9/1998 |
| WO | WO 98/38930 | 9/1998 |
| WO | WO 98/39046 | 9/1998 |
| WO | WO 98/39047 | 9/1998 |
| WO | WO 99/08744 | 2/1999 |
| WO | WO 99/42059 | 8/1999 |
| WO | WO 99/42157 | 8/1999 |
| WO | WO 99/45835 | 9/1999 |
| WO | WO 00/07657 | 2/2000 |
| WO | WO 00/44429 | 8/2000 |
| WO | WO 00/51675 | 9/2000 |
| WO | WO 00/54673 | 9/2000 |
| WO | WO 00/56391 A1 | 9/2000 |
| WO | WO 00/76390 | 12/2000 |
| WO | WO 00/76390 A2 | 12/2000 |
| WO | WO 01/05329 A1 | 1/2001 |
| WO | WO 01/12104 A1 | 2/2001 |
| WO | WO 01/45590 A2 | 6/2001 |
| WO | WO 01/45592 A1 | 6/2001 |
| WO | WO 01/58382 A2 | 8/2001 |
| WO | WO 01/70326 A1 | 9/2001 |
| WO | WO 01/91844 A1 | 12/2001 |
| WO | WO 02/22199 A2 | 3/2002 |
| WO | WO 02/32495 A1 | 4/2002 |
| WO | WO 03/007797 A2 | 1/2003 |
| WO | WO 03/008015 A2 | 1/2003 |
| WO | WO 03/009880 A2 | 2/2003 |
| WO | WO 2004/002564 A1 | 1/2004 |
| WO | WO 2004/011058 A2 | 2/2004 |

OTHER PUBLICATIONS

Kachel, R., "Current Status and Future Possibilities of Balloon Angioplasty in the Carotid Artery," Connors. Wojak (Eds); *Interventional Neuroradiology Strategies and Practical Techniques*, Chap. 46, pp. 473-484, 1998.

Kachel, Reiner, M.D., "Results of Balloon Angioplasty in the Carotid Arteries," *J. Andovasc. Surg.*, 1996, vol. 3, pp. 22-30.

Kinney, Thomas B., et al., "Shear Force in Angioplasty: Its Relation to Catheter Design and Function," *American Journal of Roentgenology*, Jan. 1985, pp. 115-122.

Kinoshita, Akira et al., "Percutaneous Transluminal Angioplasty of Internal Carotid Artery: A Preliminary Report of Seesaw Balloon Technique," *Neurological Research*, 1993.

McCleary, A.J., et al., "Cerebral Haemodynamics and Embolization During Carotid Angioplasty in High-Risk Patients," *The British Journal of Surgery*, vol. 85, No. 6, Jun. 1988, pp. 771-774.

Soler-Singla, L., et al., "Angioplastia Carotidea Con Proteccion Cerebral Y Prótesis Endovascular," *Revista De Neurologia*, 1997; vol. 25, No. 138, pp. 287-290.

Tanaka, Masato, et al., "Percutaneous Transluminal Angioplasty (PTA) for Stenosis at the Subclavian Artery and at the Origin of the Vertebral Artery: Therapeutic Indication and Some Adjunctive Safe Methods During PTA," *Neurological Surgery*, vol. 22, No. 10, 1994, pp. 939-946.

Terada, Tomoaki, et al., "Newly Developed Blocking Balloon Catheter for PTA of Internal Carotid Artery," *Neurological Surgery*, vol. 21, No. 10, 1993, pp. 891-895.

Therón, Jacques, MD, "Angioplasty of Brachiocephalic Vessels," *Interventional Neuroradiology Endovascular Therapy of the Central Nervous System*, Chapter 13, 1992, pp. 167-180.

Therón, Jacques, MD, "Carotid Artery Stenosis: Treatment with Protected Balloon Angioplasty and Stent Placement," *Radiology*, vol. 201, No. 3, Dec. 1996, pp. 627-636.

Therón, Jacques, MD, "Cerebral Protection During Carotid Angioplasty," Letters to the Editors, *J. Endovasc. Surg.*, vol. 3, 1996, pp. 484-486.

Theron, J. et al., "New Triple Coaxial Catheter System for Carotid Angioplasty with Cerebral Protection," American Journal of Neuroradiology, Sep. 1990, pp. 869-874.

* cited by examiner

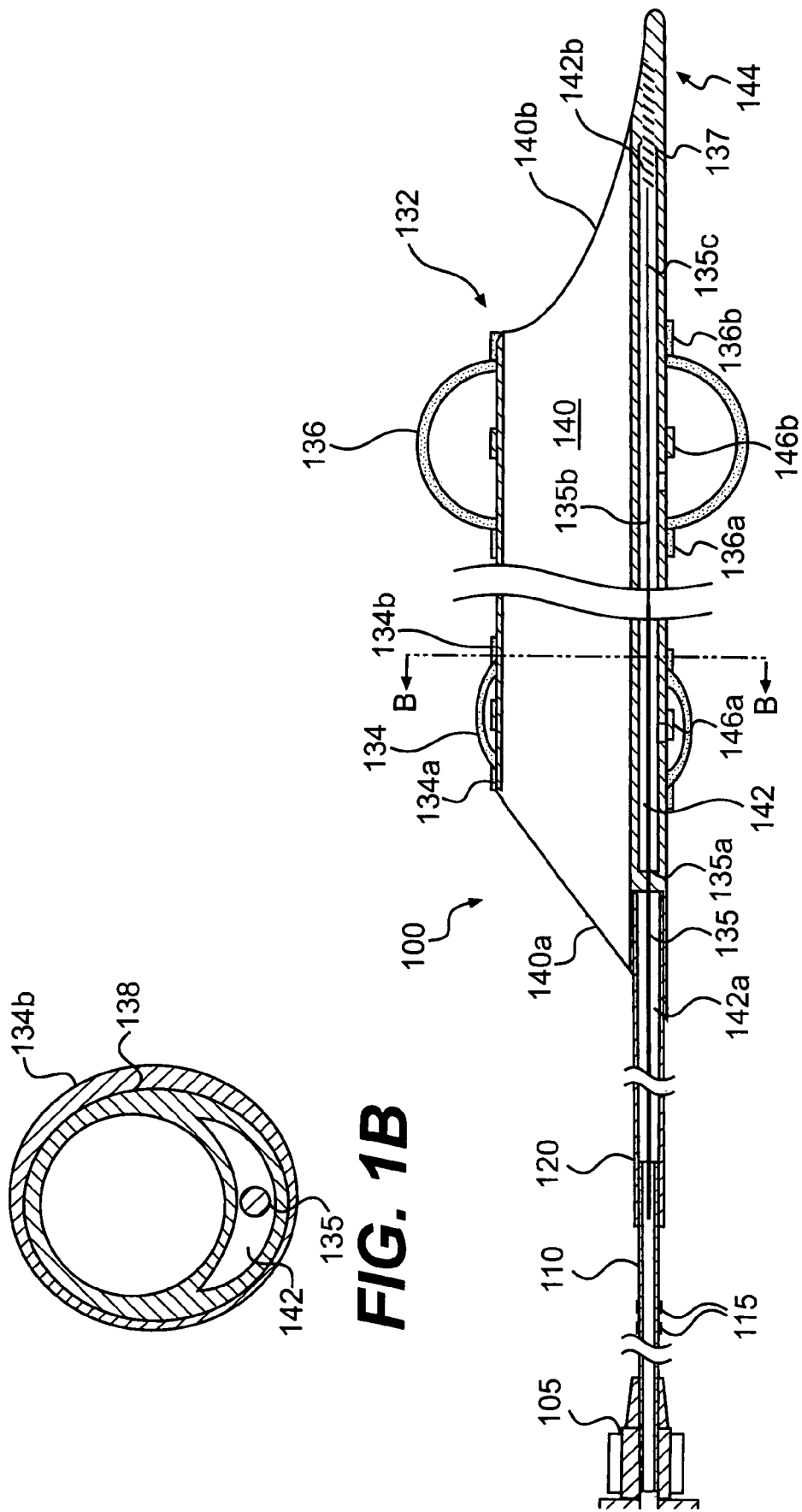

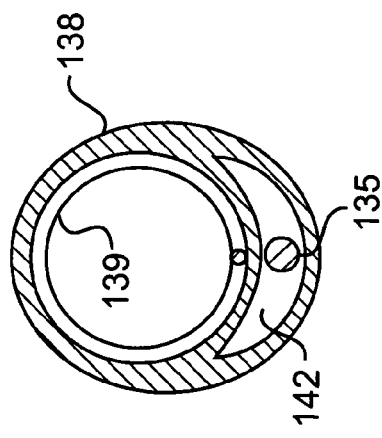
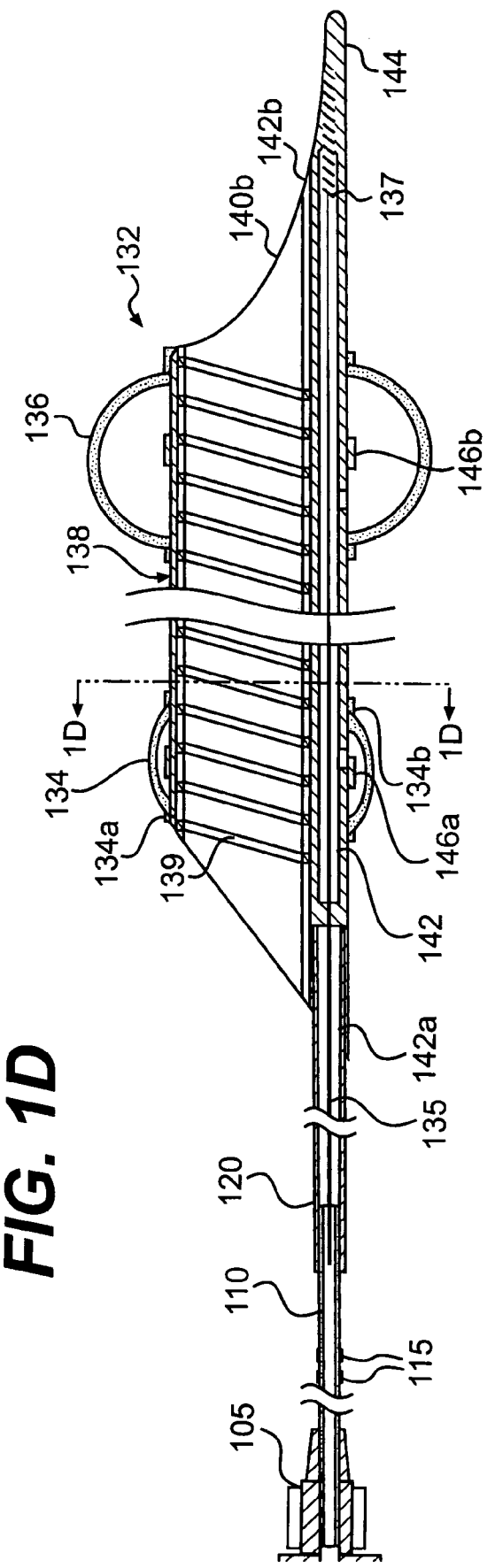

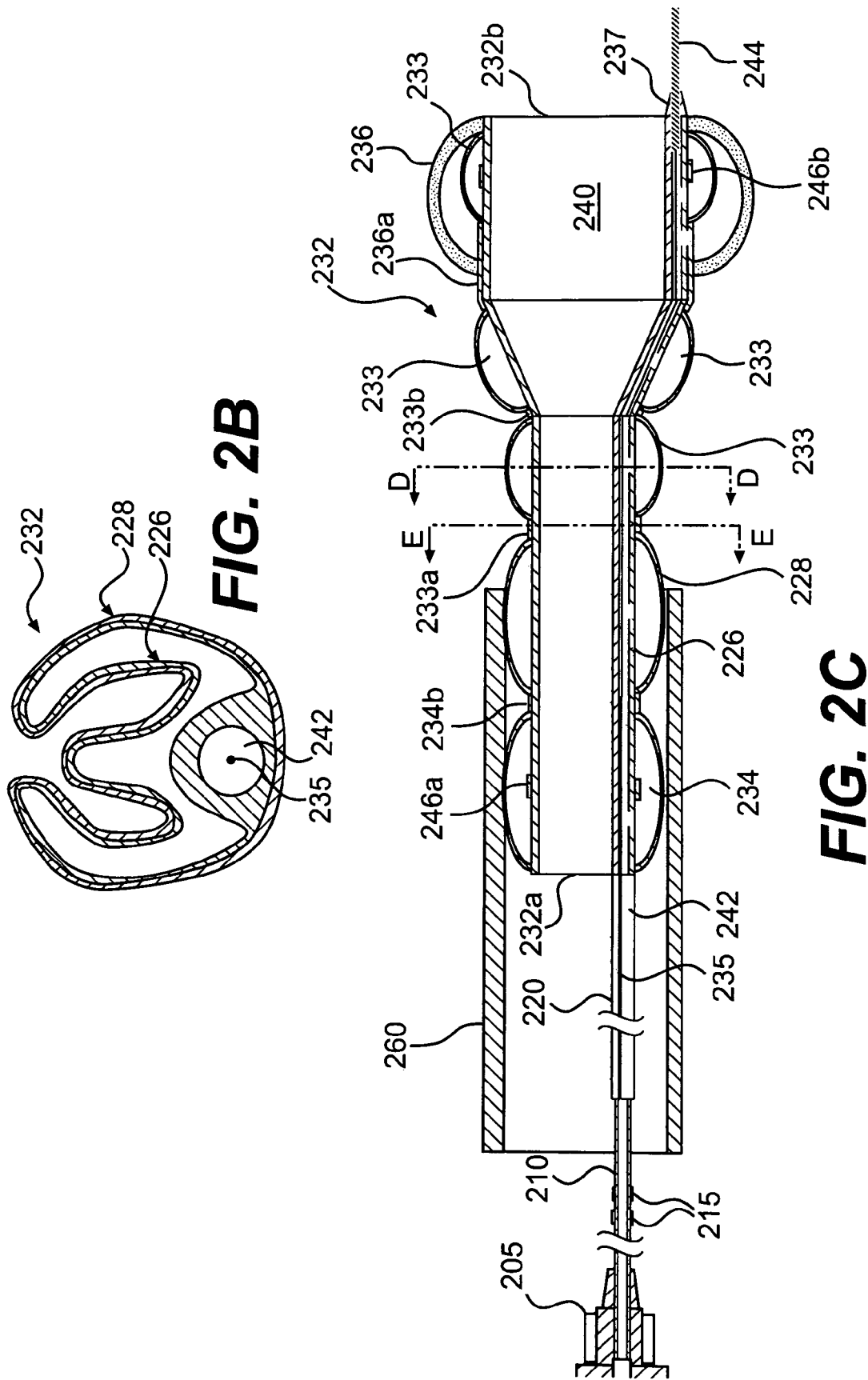

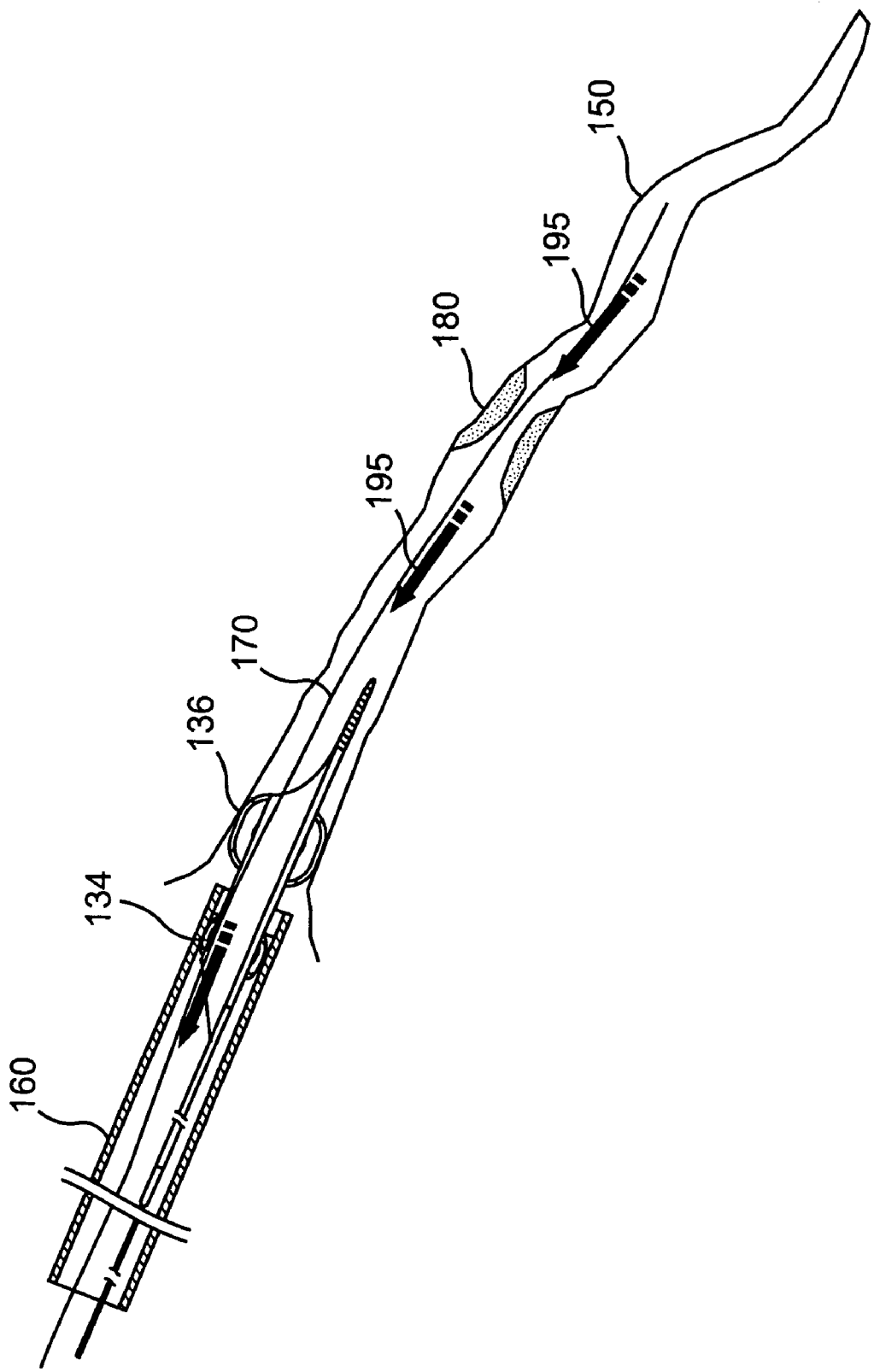

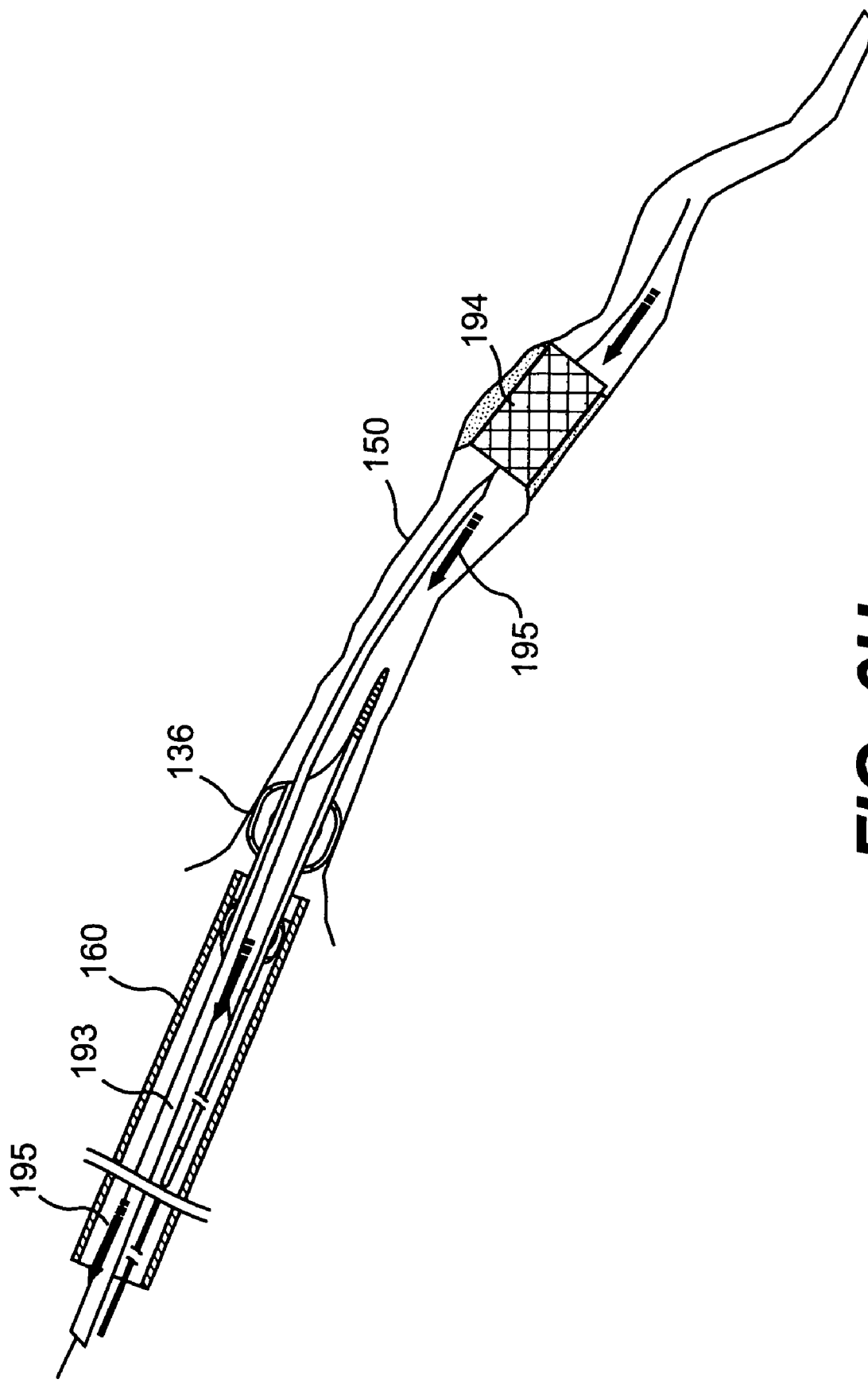

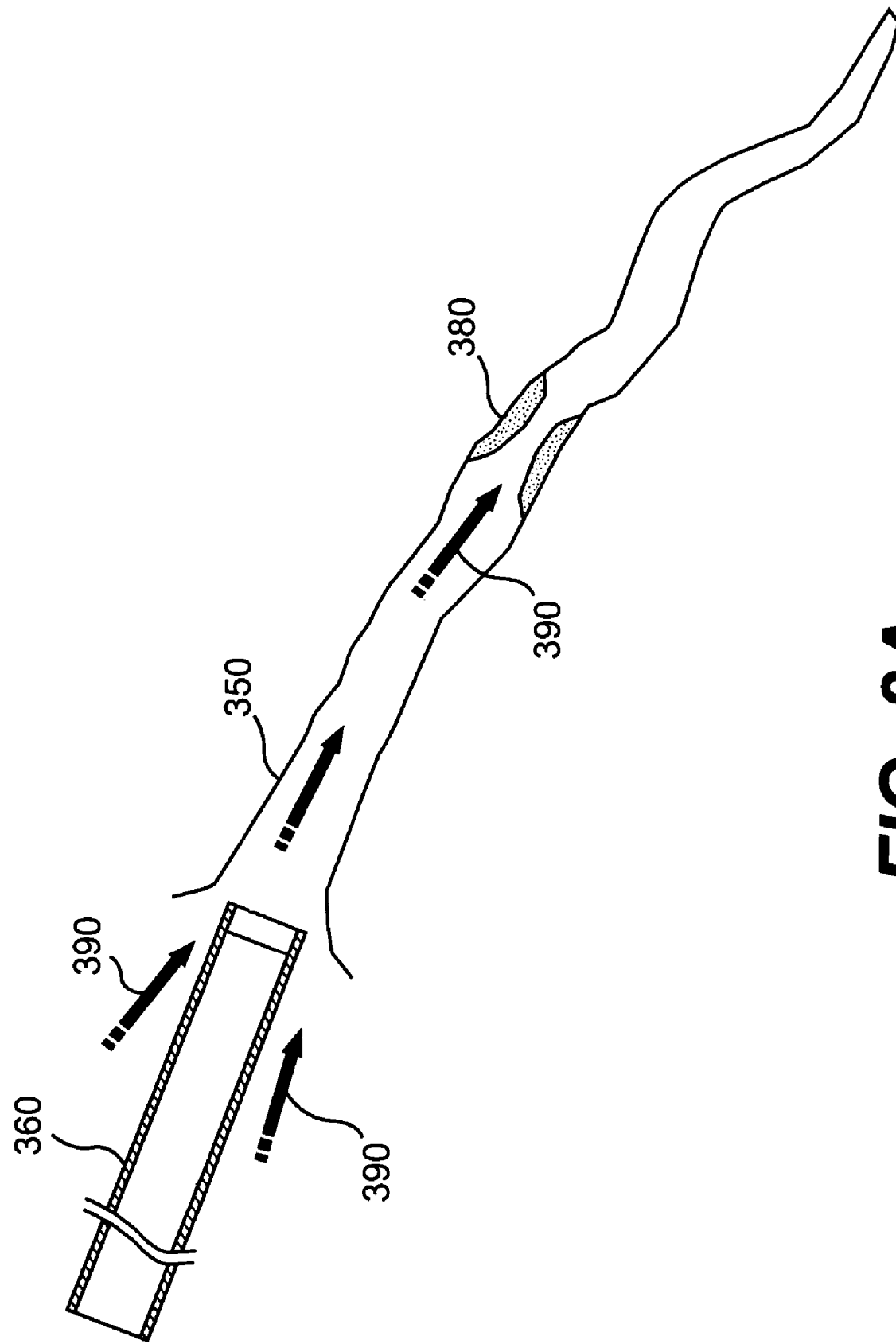

EMBOLI PROTECTION DEVICES AND RELATED METHODS OF USE

This application is a divisional of U.S. application Ser. No. 09/845,162, filed May 1, 2001, now U.S. Pat. No. 7,422,579 entitled "Emboli Protection Devices and Related Methods of Use," the entire disclosure of which is incorporated herein by reference.

FIELD OF THE INVENTION

The present invention relates to apparatus and methods used to prevent the introduction of emboli into the bloodstream during and after surgery performed to reduce or remove blockage in blood vessels.

BACKGROUND OF THE INVENTION

Narrowing or occlusion of blood vessels, such as the walls of an artery, inhibit normal blood flow. Such blockages, whether partial or full, can have serious medical consequences, depending upon their location within a patient's vascular system. Narrowing or blockage of the coronary vessels that supply blood to the heart, a condition known as atherosclerosis, may cause damage to the heart. Heart attacks (myocardial infarction) may also result from this condition. Other vessels are also prone to narrowing, including carotids, renals, cerebrals, and other peripheral arteries.

Various surgical procedures are currently used to reduce or remove the blockage in blood vessels. Such procedures include balloon angioplasty, which involves inserting a balloon catheter into the narrowed or occluded area, expanding the balloon in the narrow or occluded area, and if necessary, placing a stent in the now expanded area to keep it open. Another common procedure used is atherectomy where the lesion is cut away and removed from the vessel, or abrasively ground, sending the small particulates downstream. Other endovascular procedures make use of thrombectomy, drug delivery, radiation, stent-grafts, and various diagnostic devices.

Another alternative is bypass surgery in which a section of vein is removed from, for example, the patient's leg, e.g., a saphenous vein, to be used as a graft to form a pathway to bypass the occluded area. The saphenous vein graft (SVG), however, is also susceptible to becoming occluded in a manner similar to that of the bypassed vessel. In such a case, angioplasty (with or without the use of a stent) or atherectomy is often used on the SVG to remove or reduce the blockage.

Each of the above described procedures carries with it the risk that some of the treated plaque will be disrupted, resulting in embolic particulates released in the bloodstream. These emboli, if allowed to flow through the vascular system, may cause subsequent infarctions or ischemia in the patient. SVGs treated by angioplasty or atherectomy carry a particularly high risk of this result, but such problems are also encountered in the other types of procedures mentioned, such as carotids, or native coronary arteries, particularly those whose lesions include thrombus.

Several systems to prevent emboli being released into the bloodstream during such procedures have been tried. One system uses a balloon to totally occlude the artery distal (downstream) to the area of blockage to be treated. In this system, a guidewire with a balloon is introduced into the narrowed or occluded area, and passes through the narrowed or occluded area to a position downstream of the blockage. The balloon is inflated, the blockage is reduced or removed, and then the blood proximal to the balloon is withdrawn from the blood vessel to remove any particles or emboli which have resulted from the reduction of the blockage. While this system has shown a decrease in emboli related complications in patients undergoing such treatments, the event rate remains significant. One particular problem with this system is passing the guidewire and balloon through the narrowed or occluded area prior to occlusion with the balloon, creating the risk that emboli will be produced as the balloon passes through the blockage. Thus, any particulate or plaque disturbed during this passage which forms emboli prior to inflation of the balloon is free to flow through the vascular system, increasing the risk for infarction or ischemia. Also, any debris or particulate matter which gathers around the edges of the balloon may slip downstream during deflation and retrieval of the balloon. In addition, this system requires that blood flow be totally occluded in the vessel for relatively prolonged intervals that may induce adverse cardiac events. Although this may not be a problem clinically, many patients perceive the occlusion of blood flow for this period of time as problematic.

Another system used to prevent emboli being released into the bloodstream during surgical intervention is a filter. As with the occlusion balloon, the filter must pass through the narrowed or occluded area and is deployed distal (downstream) to the blockage. The filter then catches any particulate material generated during the removal of the blockage. The filter offers the benefit that blood flow is not totally occluded. However, because the filter must pass through the blockage, it suffers from the same drawback as the previous system—risk of the creation of emboli during passage of the filter through the blockage. In addition, it is difficult to deploy the filter securely against the walls of the vessel to prevent flow around the filter and any debris or particulate matter which gathers around the edges of the filter may slip downstream during its retrieval. Also, in order to allow blood flow during the procedure, the pores of the filter should be at least 100 microns in diameter. The majority of emboli have a diameter between about 40 microns and about 100 microns. Thus, the filter will not catch the majority of emboli, which may flow downstream and cause a infarction or ischemia. The filter also cannot prevent the passage of certain neurohumoral or vasoactive substances which are released into the blood during the procedure and may contribute to generalized vasospasm of the distal coronary tree.

Thus, there is a need for an improved system and method of treating occluded vessels which can reduce the risk of distal embolization during vascular interventions. There is also a need for a system which reduces the amount of time that total occlusion of the blood flow is necessary.

SUMMARY OF THE INVENTION

In accordance with the invention, methods and apparatuses for reducing or removing a blockage within a vessel without permitting embolization of particulate matter are provided. The methods and apparatuses occlude blood flow for a minimal amount of time and capture particulate matter created during each step of the surgical process.

According to one aspect of the invention, a method of treatment of a blood vessel is provided. The method includes advancing an evacuation sheath assembly into the blood vessel, prior to advancing a device across a stenosis to be treated, stopping normal antegrade blood flow in the blood vessel proximate to the stenosis, treating the stenosis while blood flow is stopped, and inducing retrograde blood flow within the blood vessel to carry embolic material dislodged during treating into the evacuation sheath assembly.

According to another aspect of the invention, a method for treating a diseased blood vessel is provided. The method includes positioning a guide catheter proximate to the diseased blood vessel, positioning an evacuation sheath assembly within the diseased blood vessel, prior to advancing a device across a diseased area of the blood vessel, stopping normal antegrade blood flow in the blood vessel proximate to the diseased area, advancing a guidewire through the guide catheter and the evacuation sheath assembly across the diseased area of the blood vessel while the blood flow is stopped, causing retrograde flow of blood within the diseased blood vessel to remove embolic debris dislodged by advancement of the guidewire, advancing an interventional catheter into the blood vessel to treat the diseased area of the blood vessel, and causing retrograde flow of blood within the vessel to remove embolic debris dislodged by advancement of the interventional catheter.

According to another aspect of the present invention, a method of performing a procedure on a blood vessel is provided. The method includes positioning a guide catheter proximate to the blood vessel, positioning an evacuation sheath assembly within the guide catheter, measuring pressure in the blood vessel to obtain a first pressure measurement, creating a seal between the evacuation sheath assembly and the blood vessel, measuring pressure in the blood vessel to obtain a second pressure measurement, and comparing the first and second pressure measurements.

According to yet another aspect of the invention, a method of isolating fluid communication between a catheter and a blood vessel to facilitate visualization of the blood vessel is provided. The method includes advancing a catheter proximate to the blood vessel, advancing an evacuation sheath assembly including a sealing surface through the catheter and partially into the blood vessel, expanding the sealing surface to create a seal between the blood vessel and the evacuation sheath assembly thereby stopping normal blood flow in the vessel, and injecting contrast dye into the blood vessel while the normal blood flow is stopped.

According to one aspect of the present invention, an evacuation sheath assembly is provided. The evacuation sheath assembly includes a tube having first and second lumens and first and second sealing surfaces, wherein the first lumen is an evacuation lumen configured to be placed in fluid communication with a bloodstream and wherein the second lumen is an inflation lumen in fluid communication with at least one of the first and second sealing surfaces, and a shaft in fluid communication with the inflation lumen and configured to connect to an inflation source.

According to another aspect of the invention, evacuation sheath assembly is provided. The evacuation sheath assembly includes an elongated tube defining an expandable evacuation lumen having a compressed delivery configuration and an expanded operational configuration, and a first sealing surface configured to form a seal within a catheter and a second sealing surface configured to form a seal with a blood vessel.

According to yet another aspect of the present invention, a combination for isolating fluid communication between a blood vessel and a catheter is provided. The combination includes a catheter having a lumen, and an evacuation sheath assembly configured to move within the lumen of the catheter and having an evacuation lumen and first and second sealing surfaces.

According to another aspect of the present invention, an evacuation sheath assembly comprises an elongated tube defining an evacuation lumen having proximal and distal ends, a proximal sealing surface at a proximal end of the tube configured to form a seal with a catheter, and a distal sealing surface configured to form a seal with a blood vessel.

According to a further aspect of the present invention, an evacuation sheath assembly is provided. The evacuation sheath assembly includes an elongated tube defining an evacuation lumen having open proximal and distal ends and an inflation lumen having an open proximal end and a closed distal end, and a first sealing region on a proximal portion of the evacuation lumen and a second sealing region on a distal portion of the evacuation lumen, wherein at least one of the first and second sealing regions is in fluid communication with the inflation lumen, and wherein the first sealing region is expandable to a first diameter and the second sealing region is expandable to a second diameter different than the first diameter.

According to another aspect of the present invention, an evacuation sheath assembly is provided and includes an elongated tube defining an inflation lumen and an expandable evacuation lumen having a compressed configuration and an expanded configuration, and a plurality of expandable surfaces along a length of the tube, wherein a most proximal expandable surface forms a proximal sealing surface and wherein a most distal expandable surface forms a distal sealing surface, and wherein expansion of the plurality of expandable surfaces expands the evacuation lumen from the compressed configuration to the expanded configuration.

According to another aspect of the present invention, an evacuation sheath assembly is provided. The evacuation sheath assembly includes an elongated sheath defining an evacuation lumen having open proximal and distal ends, wherein the sheath is expandable from a delivery configuration to an operational configuration, a proximal hollow shaft connected to a proximal end of the sheath, and an actuation wire connected to a distal end of the sheath, the actuation wire being movable within said shaft from a distal position to a proximal position to expand said sheath.

According to one aspect of the present invention, a method of treatment of a blood vessel is provided. The method includes advancing a guide catheter proximate to the blood vessel, advancing an evacuation sheath assembly through the guide catheter and into the blood vessel while retaining a proximal portion of the evacuation sheath assembly within the guide catheter, creating a first seal between the proximal portion of the evacuation sheath assembly and the guide catheter, creating a second seal between a distal portion of the evacuation sheath assembly and the blood vessel, stopping normal antegrade blood flow within the blood vessel, treating a stenosis within the blood vessel, causing retrograde flow within the blood vessel to thereby remove embolic material dislodged during the treating and carried by the retrograde flow into the evacuation sheath assembly, and re-establishing normal antegrade blood flow within the blood vessel.

According to another aspect of the present invention, an evacuation sheath assembly is provided. The evacuation sheath assembly includes an elongated tube defining an expandable evacuation lumen having first a first delivery configuration and a second operational configuration, and a sealing surface on a distal portion of the evacuation lumen, the sealing surface having a non-sealing configuration that corresponds to the first delivery configuration and a sealing configuration that corresponds to the second operational configuration, wherein the sealing configuration is configured to create a seal with a blood vessel.

According to another aspect of the present invention, an evacuation sheath assembly is provided. The evacuation sheath assembly includes an elongated tube defining an evacuation lumen having open proximal and distal ends and an inflation lumen having an open proximal end and a closed distal end, at least one inflatable sealing surface in fluid communication with the inflation lumen, and a soft steerable tip on a distal end of the elongated tube.

According to yet another aspect of the present invention, an evacuation sheath assembly includes an elongated tube defining an evacuation lumen having open proximal and distal ends and an inflation lumen having an open proximal end and a closed distal end, and at least one inflatable sealing surface in fluid communication with the inflation lumen, wherein the open distal end of the evacuation lumen is angled.

According to another aspect of the present invention, an evacuation sheath assembly is provided and includes an elongated tube defining an evacuation lumen having open proximal and distal ends and an inflation lumen having an open proximal end and a closed distal end, and first and second sealing surfaces on the tube, wherein the open proximal end of the evacuation lumen is angled.

According to a further aspect of the present invention, an evacuation sheath assembly includes an elongated tube defining an evacuation lumen having open proximal and distal ends and an inflation lumen having an open proximal end and a closed distal end, and at least one inflatable sealing surface in fluid communication with the inflation lumen, wherein the evacuation lumen is shorter than the inflation lumen.

According to another aspect of the invention, an evacuation sheath assembly is provided and includes an elongated tube defining an evacuation lumen having open proximal and distal ends and an inflation lumen having an open proximal end and a closed distal end, and at least one inflatable sealing surface in fluid communication with the inflation lumen, wherein a proximal portion of the evacuation lumen has a first diameter and a distal portion of the evacuation lumen has a second diameter larger than the first diameter.

According to another aspect of the present invention, a method for treating a diseased blood vessel is provided. The method includes positioning a guide catheter within the ostium of a target vessel, advancing an evacuation sheath assembly through the guide catheter and beyond a major side branch of the target vessel, forming a first seal between the target vessel and a distal portion of the evacuation sheath assembly, forming a second seal between the catheter and a proximal portion of the evacuation sheath assembly, and advancing an interventional device through a lumen of the evacuation sheath assembly to treat the target vessel.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings, FIG. 1A is a cross-sectional side view of a partial length evacuation sheath according to one embodiment of the present invention;

FIG. 1B is a cross-sectional view of the partial length evacuation sheath taken along line 1B-1B of FIG. 1A;

FIG. 1C is a cross-sectional side view of an alternative embodiment of a partial length evacuation sheath according to one embodiment of the present invention;

FIG. 1D is a cross-sectional view of the partial length evacuation sheath taken along line 1D-1D of FIG. 1C;

FIG. 2B is a cross-sectional view of the unexpanded expandable evacuation sheath taken along line 2B-2B of FIG. 2A;

FIG. 2C is a cross-sectional side view of the expandable evacuation sheath of FIG. 2A in an expanded state;

FIG. 48 is cross-sectional view of the guiding catheter/evacuation sheath combination taken along line 4B-4B of FIG. 4A;

FIGS. 6A-6I are cross-sectional views of the partial length evacuation sheath of FIGS. 1A and 1B as employed in a method according to one aspect of the present invention;

FIGS. 7A-7I are cross-sectional views of the expandable evacuation sheath of FIGS. 2A-2D as employed in a method according to another aspect of the present invention;

FIGS. 8A-8I are cross-sectional views of the full-length evacuation sheath of FIGS. 3A and 3B as employed in a method according to a further aspect of the present invention;

DESCRIPTION OF THE EMBODIMENTS

Figure 2A:
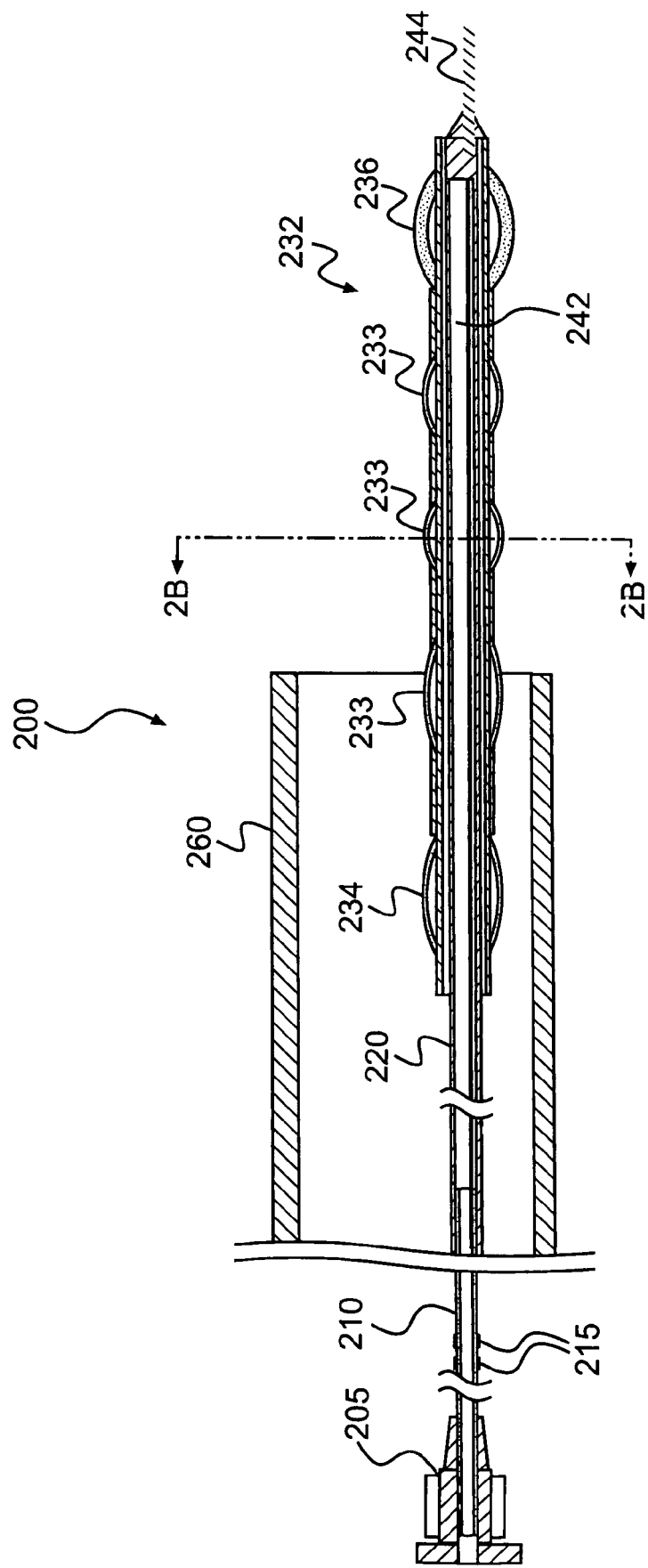
FIG. 2A is a cross-sectional side view of an expandable evacuation sheath, shown in an unexpanded state, according to another embodiment of the present invention.

Reference will now be made in detail to the present embodiments of the invention, examples of which are illustrated in the accompanying drawings. Wherever possible, the same reference numbers will be used throughout the drawings to refer to the same or like parts.

The present invention provides a system and method for evacuating emboli, particulate matter, and other debris from a blood vessel, and particularly from an occluded blood vessel. As used herein, an "occlusion," "blockage," or "stenosis" refers to both complete and partial blockages of the vessels, stenoses, emboli, thrombi, plaque, debris and any other particulate matter which at least partially occludes the lumen of the blood vessel.

Additionally, as used herein, "proximal" refers to the portion of the apparatus closest to the end which remains outside the patient's body, and "distal" refers to the portion closest to the end inserted into the patient's body.

This method and apparatus are particularly suited to be used in diseased blood vessels that have particularly fragile lesions, or vessels whereby the consequences of even small numbers of small emboli may be clinically significant. Such blood vessels include diseased SVGs, carotid arteries, coronary arteries with thrombus, and renal arteries. However, it is contemplated that the method and apparatus can be adapted to be used in other areas, such as other blood vessels.

As embodied herein and shown in FIG. 1A, an evacuation sheath assembly 100 is provided. Evacuation sheath assembly 100 includes an evacuation head and a shaft. As embodied herein and shown in FIG. 5A, the evacuation sheath assembly 100 is sized to fit inside a guide catheter to advance a distal end of the evacuation sheath assembly into a blood vessel to treat a stenosis.

Although described herein with respect to coronary artery intervention, it is contemplated that evacuation sheath assembly 100 may be suitable for use in other surgical procedures in other vessels, where reduction or removal of a blockage in a blood vessel is beneficial. Additionally, although the method of use of the evacuation sheath assembly will be described with respect to placing a stent within a vessel, the evacuation sheath assembly 100 can be used during other therapies, such as angioplasty, atherectomy, thrombectomy, drug delivery, radiation, and diagnostic procedures.

As shown in FIG. 1A, an evacuation head 132 is provided. Evacuation head 132 includes a multi-lumen tube 138 is preferably made of a relatively flexible polymer such as low-density polyethylene, polyurethane, or low durometer Pebax® material. Alternatively, the multi-lumen tube 138 can be made of a composite polymer and metal material or from other suitable biocompatible materials exhibiting appropriate flexibility, for example. The multi-lumen tube 138 preferably includes first and second lumens. The first and preferably larger of the lumens, an evacuation lumen 140, is designed to allow for the passage of interventional devices such as, but not limited to, stent delivery systems and angioplasty catheters. The evacuation lumen 140 is also designed to allow for fluid flow, such as blood, blood/solid mixtures, radiographic dye and saline, within the evacuation lumen 140. This flow of fluid may occur regardless of whether an interventional device is within the evacuation lumen 140. The proximal and distal ends 140a, 140b of the evacuation lumen 140 are preferably angled to allow for smoother passage of the evacuation sheath assembly 100 through a guide catheter, and into a blood vessel, and to facilitate smoother passage of other therapeutic devices through the evacuation lumen 140 of the evacuation head 132. The larger area of the angled open ends also allows for larger deformable particulate matter to pass through the lumen more smoothly.

The second and preferably smaller lumen of the multi-lumen tube 138 is an inflation lumen 142 (having an open proximal end 142a and a closed distal end 142b) designed to provide fluid to inflate balloons on the evacuation head 132. The fluid may be either gas or liquid in form.

An alternative construction of the multi-lumen tube 138 of the evacuation head 132 is shown in FIG. 1C. Depending on the tortuosity of the curves of the guide catheter and the blood vessel through which the evacuation head 132 is to be advanced, it may be desirable to incorporate a kink resisting structure. As embodied herein and shown in FIG. 1C, a coil 139 may be embedded within the multi-lumen tube 138. A coil 139 may be positioned on the inside surface defining the evacuation lumen 140. The coil 139 can be "wound-down" initially then re-expanded to make contact with the inner surface of evacuation lumen 140. A covering of polyurethane can then be applied to contain the coil 139, and secure it in position within evacuation lumen 140. The polyurethane may be applied by a solvent casting of polyurethane in an appropriate solvent. Alternatively, the structure may be formed by coextruding the shaft tube together with a coil or braid or by other suitable means. A further alternative may include positioning the coil on the outer surface of the multi-lumen tube 138.

According to one aspect of the invention, the evacuation head includes at least one expandable sealing surface. As embodied herein and shown in FIG. 1A, two expandable sealing surfaces are provided. A first proximal sealing surface is configured to form a seal within the guide catheter which delivers the evacuation sheath assembly 100 to the surgical site, as will be described. First proximal sealing surface is preferably a proximal sealing balloon 134. A second distal sealing surface is configured to form a seal within the blood vessel, as also will be described. Second distal sealing surface is preferably a distal sealing balloon 136. As shown in FIG. 1A, it is preferable that the distal sealing balloon 136 be larger in size than the proximal sealing balloon 134. The proximal balloon 134 and the distal balloon 136 are in fluid communication with the inflation lumen 142 of evacuation head 132. Inflation lumen 142 is in fluid communication with a balloon inflation device 199 (see FIG. 5A). Although only a single inflation lumen 142 is shown, it is possible to use more than one inflation lumen. In such an embodiment, the multi-lumen tube 138 would comprise three lumens, two inflation lumens, each one in fluid communication with one of the sealing balloons 134, 136, and one evacuation lumen. Each lumen would be in fluid communication with its own lumen extending proximally to an inflation device (not shown).

Preferably, the proximal and distal balloons 134, 136 are formed of an elastomer such as polyurethane or silicone. It is preferable to utilize elastomeric balloons, particularly for the distal sealing balloon 136, to allow the balloon to have a range of inflated diameters, depending on the volume of fluid infused into the balloon. Each sealing balloon 134, 136 includes two waist portions, one proximal 134a, 136a and one distal 134b, 136b of a body portion of the balloon. The waists portions 134a, 134b, 136a, 136b are preferably secured to an exterior of the multi-lumen tube 138 using heat welding, solvent bonding, or other suitable adhesive bonding techniques.

Although use of separate proximal and distal sealing balloons 134, 136 is preferred, it is possible to instead use a single elastomeric tube extending nearly the full length of the multi-lumen tube 138. The single elastomeric tube would be secured to the outside of the multi-lumen tube 138 at the distal and proximal ends 140b, 140a of evacuation lumen 140, as well as in the middle region of the evacuation lumen 140. In this manner, two expandable sealing surfaces are provided by the two regions of the single elastomeric tube which are not secured to the exterior of the shaft tube, i.e., the region between the proximal end 140a and the middle region would form a proximal sealing surface, and the region between the distal end 140b and the middle region would form a distal sealing surface.

As embodied herein, the balloons 134, 136 may be blow molded from tubing or dip molded to approximate the shape and minimum anticipated diameter of their final inflated condition. Particularly for the distal sealing balloon 136, further inflation would further increase the diameter, as the balloon is preferably elastomeric. Alternatively, however, the balloons need not be pre-molded to the expanded shape. In such a variation, each balloon 134, 136 is preferably a uniform diameter tube between the two balloon-waists 134a, 134b, 136a, 136b. As the uniform diameter tubes are preferably elastomeric materials, they can be elastically expanded to the same shape and size as the alternative pre-molded balloons. The non-pre-molded balloons would require a higher inflation pressure to expand to a particular dimension. Furthermore, the non-pre-molded elastomeric balloons would deflate more easily, as the elasticity would help to force the inflation fluid from the interior of the balloons. To improve the range of expandability of the elastomeric balloons, it is preferable for the body portion of each balloon 134, 136 to have a length at least as great as the maximum inflated diameter, and more preferably several times longer, for example about 3-4 times longer.

While it is preferred to provide the two expandable sealing surfaces of two elastomeric balloons 134, 136, as described above, it is possible to fabricate the proximal sealing balloon 134 of a non-elastomeric polymer molded to the shape and size as shown in FIG. 1A. Since the proximal balloon 134 is intended to be inflated within the guide catheter, it is only necessary for the proximal balloon 134 to be inflated against the internal diameter of the guide catheter. The distal sealing balloon 136, however, preferably has a relatively wide range of expanded diameters, and therefore benefits from being elastomeric. Additionally, if the distal sealing balloon 136 is elastomeric, and the proximal sealing balloon 134 is fabricated of a pre-molded thin-walled polymer such as PET or nylon, and if both balloons are inflated from a common inflation lumen 142, then the proximal sealing balloon 134 will expand against the internal surface of the guide catheter, causing a seal, prior to any significant expansion of the distal sealing balloon 136 beyond its initial dimension.

Figure 5A:
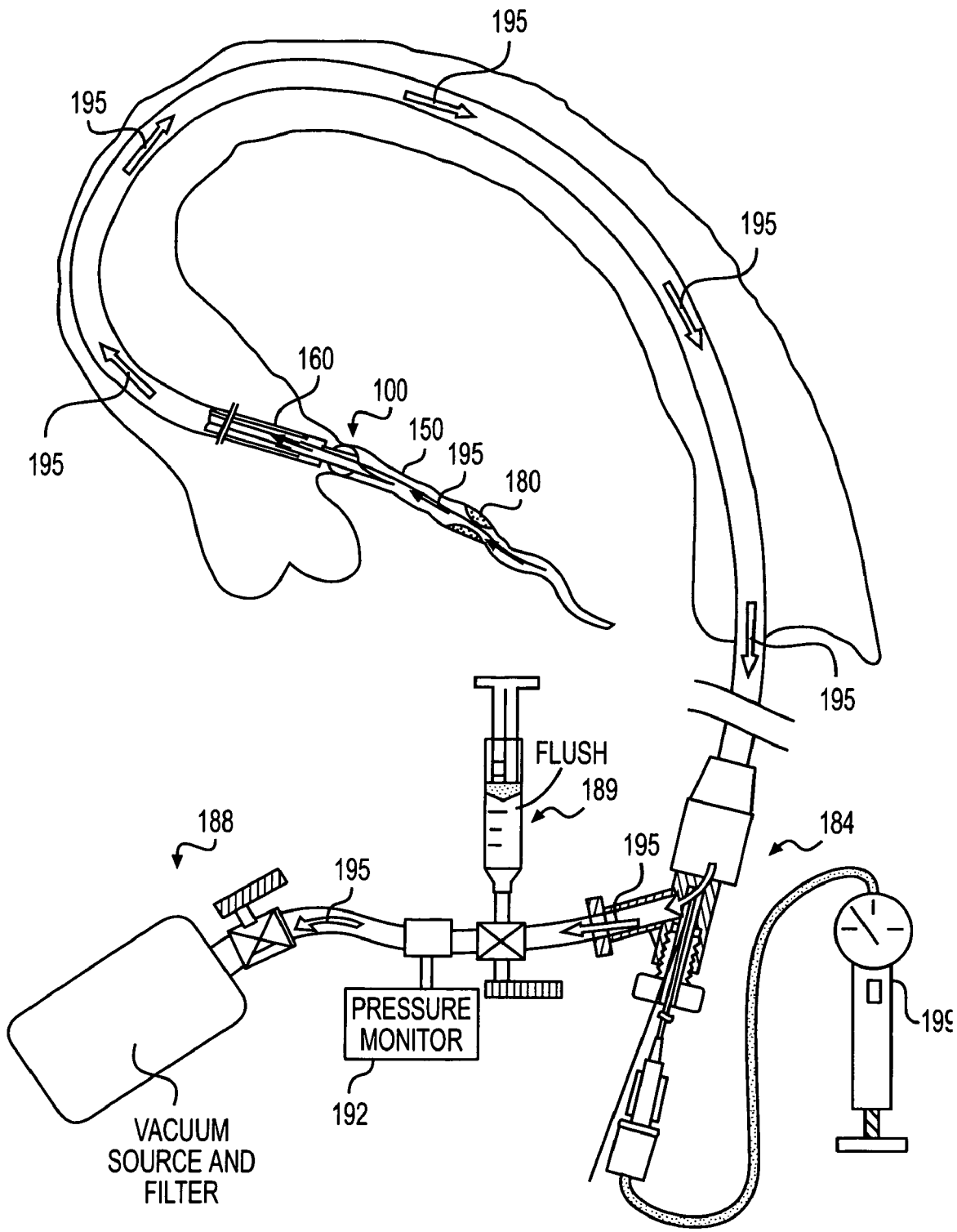
FIG. 5A is cross-sectional view of the partial evacuation sheath of FIGS. 1A and 1B deployed within a vessel.
Figure 5B:
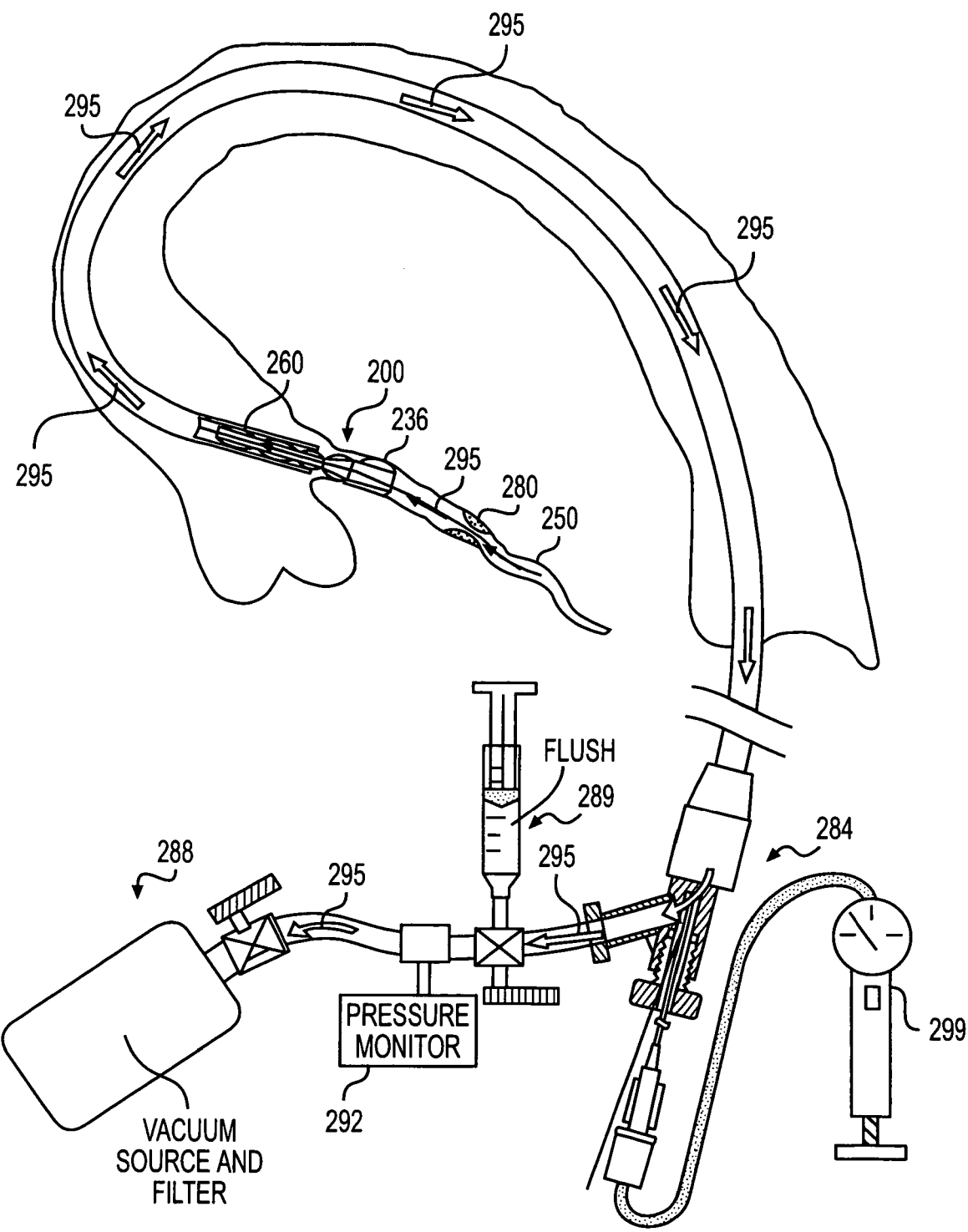
FIG. 5B is cross-sectional view of the expandable evacuation sheath of FIGS. 2A-2D deployed within a vessel.
Figure 6A:
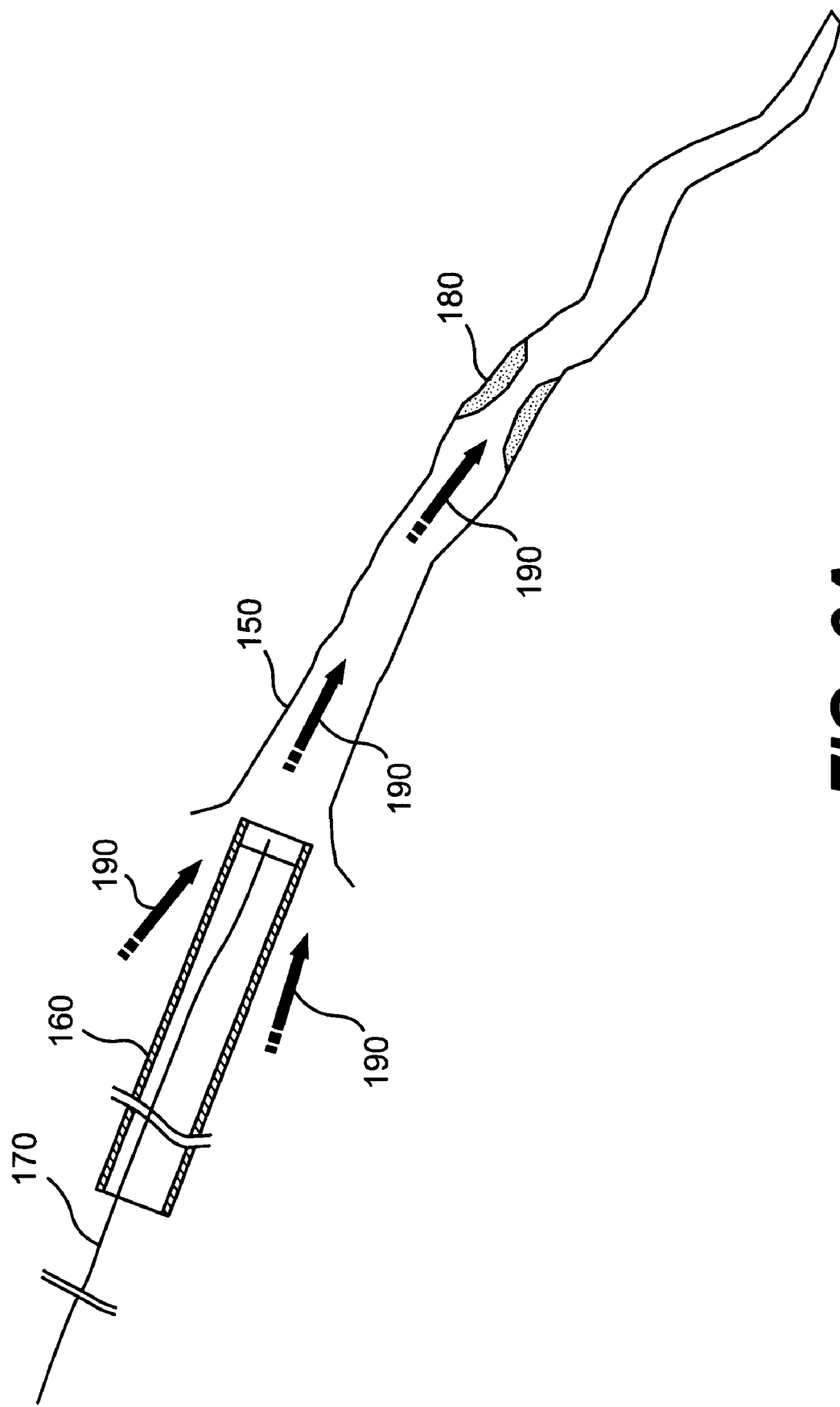

As discussed earlier, the evacuation sheath assembly 100 is configured to be used with a guiding catheter 160 (see FIGS. 5A and 6A). The guiding catheter 160 performs an evacuation function in combination with the evacuation lumen 140. The guiding catheter 160 also maintains a contrast delivery function. The evacuation head 132, with its two sealing balloons 134, 136 inflated, is intended to isolate fluid communication of the internal lumen of the guide catheter 160 to the blood vessel 150 in which it is inserted. Preferably, proximal and distal radiopaque markers 146a, 146b are placed at the site of each balloon 134, 136. Alternatively, two markers may be placed proximally and distally adjacent to each balloon 134, 136. The proximal and distal radiopaque markers 146a, 146b allow the operator to radiographically position the two sealing balloons 134, 136 in the proper location within the guiding catheter 160 and the blood vessel 150.

In use, the distal balloon 136 is intended to be positioned distal of the distal tip of a guiding catheter 160 and inflated against the inside surface of the blood vessel 150 causing a fluid tight seal between the blood vessel 150 and the balloon 136. The proximal balloon 134 is intended to be positioned proximal of the distal end of the guiding catheter 160 and inflated against the guiding catheter 160 causing a fluid tight seal.

The preferred inflated diameters of the sealing balloons 134, 136 are thus determined by the intended application. For example, if the evacuation sheath assembly 100 is intended to be used in a diseased saphenous vein bypass graft, (SVG), a guiding catheter of 8 French may be utilized. The proximal sealing balloon 134 will therefore require an inflated diameter capable of sealing against the inside of the guiding catheter, typically in the range of about 0.088-0.096 inches. The distal sealing balloon 136 will need to be capable of sealing against the inside of the SVG, which typically has an inside diameter ranging from about 2.5-6 mm.

The length of the evacuation head 132 is dependent on the application for which the evacuation sheath assembly 100 is intended to be used. It is intended that the evacuation head 132 be long enough for the proximal sealing balloon 134 to be sealingly inflated within the guide catheter 160, and the distal sealing balloon 136 to be sealingly inflated within the blood vessel of interest. In many applications, therefore, evacuation head 132 can be relatively short. For example, in the case of an SVG application, this length may be on the order of 2 to 5 cm. However, in a native coronary artery application, particularly in the left coronary circulation, it may be desired to have the evacuation head 132 longer, such that the distal sealing balloon 136 is positioned beyond the first or other main bifurcation. For example, it may be desired to position the distal sealing balloon 136 within the left anterior descending artery, distal of the left main artery. For this application, the evacuation head 132 is preferably about 5 to about 20 cm in length.

The diameter of the evacuation head 132 is also dependent on the intended application. As an example, preferred dimensions are described here with respect to an application in SVGs, with use of an 8 French guide catheter whose inner diameter is about 0.090 inches. The evacuation lumen 140 may be approximately 0.061 inches, which will allow the passage of most therapeutic devices such as angioplasty catheters, stent delivery catheters, atherectomy catheters, drug delivery catheters, etc. The inflation lumen 142 may have a dimension of about 0.005 inches at the widest portion of the crescent (vertical direction in FIG. 1B). The wall thickness for most of the multi-lumen tube wall 138 may be about 0.002 inches, and the balloon waist thickness may be approximately 0.002 inches. These dimensions create an evacuation head 132 having a maximum diameter (in delivery condition) of about 0.076 inches, less than the inner diameter of the guide catheter 160.

According to another aspect of the invention, the evacuation sheath assembly 100 includes a shaft. As embodied herein and shown in FIG. 1A, the shaft includes a proximal shaft portion 110, an intermediate shaft portion 120, and a distal shaft portion 130 (not shown in FIG. 1A, shaft portion 130 includes evacuation-head 132).

Proximal shaft portion 110 forms a hollow tube. Preferably, proximal shaft portion 110 is made of stainless steel, however, other structures and materials, such as polymer and metallic composites, (e.g., braid reinforced polymer tubes), nickel-titanium alloy, or other suitable materials exhibiting appropriate biocompatibility and flexibility properties may be used. The proximal shaft portion 110 provides fluid communication between an inflation apparatus (not shown) and the intermediate and distal shaft portions 120, 130. The proximal shaft portion 110 may also be coated with a polymer sleeve or spray coating for lubricity.

Preferably, the proximal shaft portion 110 includes markers 115 on its exterior surface. These markers 115 are positioned to indicate to a user that the evacuation sheath assembly 100 has been advanced through the guiding catheter 160 to a location where the distal end of the evacuation sheath assembly 100 is just proximal to the distal end of the guiding catheter 160. The proximal shaft portion 110 is preferably secured to a luer hub 105, for example by an overlapping weld or adhesive bond joint. The luer hub 105 allows the evacuation sheath assembly 100 to be connected to an inflation apparatus for the inflation of the sealing balloons 134, 136. Any suitable inflation device may be used, including those resident in hospital cath labs.

An intermediate shaft portion 120 is secured to the proximal and distal shaft portions 110, 130, preferably by an overlapping weld or bond joint. Intermediate shaft portion 120 forms a hollow tube. Intermediate shaft portion 120 is preferably formed of polyethylene or Pebax, however, other polymers and polymer metallic composites, such as polyimide with an incorporated braid of stainless steel wire, or other suitable material exhibiting appropriate biocompatibility and flexibility characteristics, may be used. The intermediate shaft portion 120 provides fluid communication between the proximal shaft portion 110 and the distal shaft portion 130. The intermediate shaft portion 120 also transmits longitudinal force from the proximal shaft portion 110 to the distal shaft portion 130. The intermediate shaft portion 120 is preferably more flexible than the proximal shaft portion 110, to allow navigation of the curves within the distal region of the guiding catheter, as are often present, particularly in cardiac related applications.

A distal end of the intermediate shaft portion 120 is connected to a distal shaft portion 130, preferably by welding or bonding. Distal shaft portion 130 includes the inflation lumen 142 of multi-lumen tube 138 and a soft distal tip portion 144. As shown in FIG. 1A, the inflation lumen 142 is in fluid communication with the proximal shaft portion 110 and intermediate shaft portion 120. The distal end of inflation lumen 142 ends in a solid portion forming the distal end of the distal shaft portion 130. The distal end of the distal shaft portion 130 is tapered to form soft tip 144. The soft tip 144 may comprise a more flexible polymer secured to the distal end of the multi-lumen tube 138 of the evacuation head 132. For example, if the multi-lumen tube 138 is fabricated of high density polyethylene, the soft tip 144 may be fabricated of a low durometer polyurethane or Pebax. The soft tip 144 allows the evacuation sheath assembly 100 to be placed atraumatically into the blood vessel, even if the blood vessel exhibits tortuosity.

The shaft of the evacuation sheath assembly preferably includes a stiffness transition member 135. Stiffness transition member 135 is attached to the distal end of the proximal shaft portion 110, for example by welding or bonding. The stiffness transition member 135 is preferably made of stainless steel, but other metals such as nickel titanium alloy or polymers may be used. The stiffness transition member 135 is located co-axially in the inflation lumen 142 (as shown in FIG. 1B) and extends from the proximal shaft portion 110 to the soft tip 144. A distal end 137 of the stiffness transition member 135 preferably includes a spring tip embedded into the material of the soft tip 144. Embedding the spring tip into the soft tip 144 allows the stiffness transition member 135 to prevent longitudinal stretching or compressing of the evacuation sheath assembly 100.

Alternatively, the distal end 137 of the stiffness transition member 135 can have a enlarged welded ball or other shape which can serve to mechanically interlock the stiffness transition member 135 within the soft tip 144. The portion of the stiffness transition member 135 within the tip 144 of the evacuation sheath assembly 100 also serves to allow the tip to be formed in a "J-bend", similar to that for coronary guide wires. The stiffness transition member 135 can then transfer rotational forces and motion imparted from the proximal region of the evacuation sheath assembly 100 to the tip 144, to facilitate steering and navigation of the evacuation head 132 to a desired site in the blood vessel.

The stiffness transition member's bending stiffness decreases gradually from the proximal end to the distal end of the stiffness transition member 135. Preferably, this is accomplished by reducing the cross sectional area of the member 135 as shown in FIG. 1A, where stiffness transition member 135 includes three portions of decreasing diameter 135a, 135b, 135c from proximal to distal end. However, this can also be accomplished by changes in shape and/or materials. The stiffness transition member 135 allows for a gradual stiffness reduction in the evacuation sheath assembly 100, which allows it to more smoothly navigate the curves of the guiding catheter and the blood vessel. This shaft construction is exemplary only, and is not intended to limit the invention.

As mentioned, although described herein with respect to stent placement in an SVG or coronary artery having a stenosis, evacuation sheath assembly 100 may be used in other surgical procedures and with other therapeutic devices, such as balloon angioplasty, atherectomy, thrombectomy, drug delivery, radiation, and diagnostic procedures.

As embodied herein and shown in simplified drawing FIG. 6A, the lumen of a blood vessel 150 is accessed with the distal end of a guiding catheter 160, which is well known in the art and typical for coronary-type procedures. A coronary guide wire 170 then is advanced to a location just proximal to the distal tip of the guiding catheter 160. Blood flow at this point remains in the direction of normal arterial blood flow. The blood is flowing around and past the distal tip of the guiding catheter 160 and through the stenosis 180 as indicated by arrows 190.

Figure 6B:
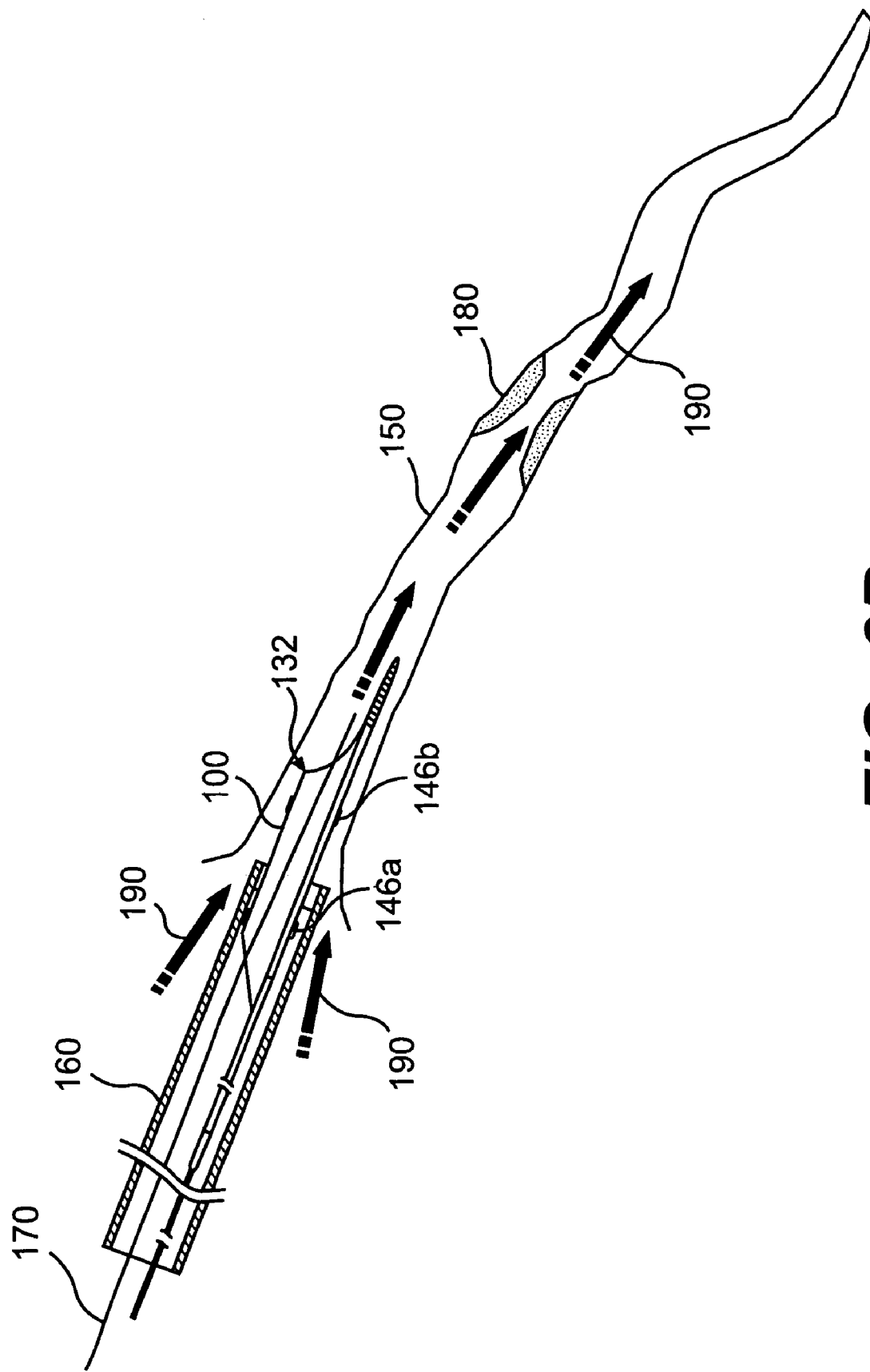

As shown in FIG. 6B, the evacuation sheath assembly 100 then is advanced over the guide wire 170 and positioned within the vessel 150 with the distal radiopaque marker 146b distal of the distal tip of the guiding catheter 160 (i.e., within the vessel 150) and the proximal marker 146a proximal of the distal tip of the guiding catheter 160 (i.e., within catheter 160), as determined through appropriate imaging techniques known in the art. Alternatively, the guide catheter 160 may be positioned within the ostium of the target vessel, and the evacuation sheath assembly 100 may be advanced through the catheter and beyond a major side branch of the target vessel.

Blood flow continues to be in the direction of normal arterial blood flow as shown by arrows 190. Because the assembly 100 has as relatively short evacuation head 132, the entire evacuation sheath assembly 100 can be advanced over a conventional length coronary guide wire 170 after the guide wire 170 has been placed within the guide catheter 160.

Figure 6C:
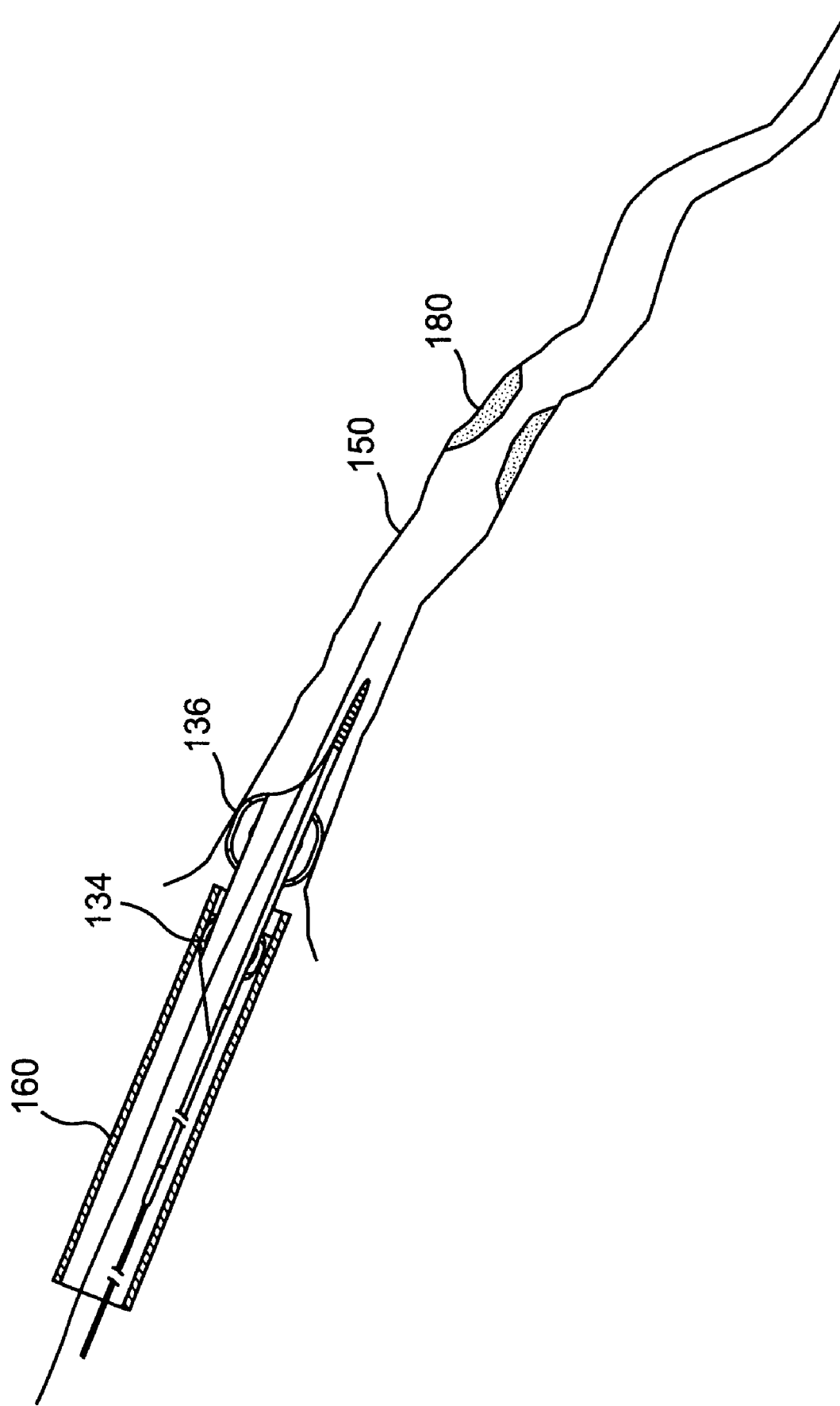

Once the evacuation head 132 is positioned with its distal end within the vessel 150 while its proximal end remains in the catheter 160, the distal and proximal sealing balloons 136, 134 are inflated as shown in FIG. 6C. The distal sealing balloon 136 provides a fluid tight seal between the sealing balloon 136 and the blood vessel 150 and the proximal sealing balloon 134 provides a fluid tight seal between the sealing balloon 134 and the interior diameter of the guiding catheter 160. A suitable valve 184, such as a touhy borst valve, attached to the guiding catheter 160 (shown in FIG. 5A) provides a fluid tight seal against the guide wire 170 and the proximal shaft portion 110 of the evacuation sheath assembly 100. The three fluid tight seals establish fluid communication between the distal end of the evacuation sheath assembly 100 and a fluid collection chamber, filter, and vacuum source 188, which is attached to the Y-adaptor (conventional) 184 shown in FIG. 5A. A blood pressure transducer 192 is commonly connected in fluid communication with the lumen of the guide catheter 160 (through additional stop cocks or manifolds as is well-known in the art) to monitor arterial blood pressure. As the sealing balloons 134, 136 are inflated to establish the fluid communication of the evacuation sheath assembly and guide catheter 160 with the collection chamber, filter, and vacuum source 188, the blood pressure waveform can be observed to change from a relatively high pressure and pulsatile waveform of the artery, to a relatively low and constant waveform of the venous pressure. This pressure observation is an important indicator that the sealing balloons 134, 136 have effectively isolated fluid communication to the coronary artery. With the three fluid tight seals in place, a normal antegrade flow within the artery is stopped. Thus, there is substantially no blood flow within the vessel 150, as indicated by the lack of arrows in FIG. 6C.

At this point, it may be desirable to inject a small amount of contrast into the blood vessel, via a dye injection apparatus 189 in fluid communication with the guide catheter 160, evacuation head 132, and blood vessel 150, to aid in navigation of the guide wire 170 across the stenosis 180. The evacuation lumen 140 of the evacuation head 132 becomes an extension of the guide catheter lumen for this contrast delivery. Because normal antegrade blood flow in the coronary artery has been effectively, stopped, the contrast will remain in the coronary artery, rather than quickly washing away. This may be advantageous for the subsequent navigation of the guide wire 170.

Once antegrade flow is stopped, as shown in FIG. 6C, the guide wire 170 is advanced across the stenosis 180. In most cases, to begin advancing the guide wire 170, the touhy borst valve 184 on the Y-adaptor (shown in FIG. 5A) will need to be opened just enough to allow for movement of the wire 170, but not so much to allow vigorous backbleeding. In the procedure described here, it is preferred to open the valve only enough such that there is little to no backbleeding, otherwise the venous pressure head in the coronary artery can cause retrograde flow during this step, thereby pushing all of the contrast back into the guide catheter and out of the blood vessel.

Once the wire has crossed the stenosis 180, it may be desirable to cause retrograde flow in the coronary artery (FIG. 6D), as the act of crossing a stenosis 180 with a wire 170 (particularly a fragile lesion (stenosis), such as in an SVG) may in itself dislodge material. Any material dislodged will not travel downstream, as the antegrade flow has already been stopped. Retrograde flow can be used to remove the dislodged material.

With all seals in place, blood flow may now be established from the distal end of the evacuation head 132 to the collection chamber, and filter 188 to remove any dislodged material. Retrograde flow is represented in FIG. 6D by arrows 195. This retrograde flow is due to the venous pressure head, and will begin once the pressure in the collection bottle 188 is vented to atmospheric pressure. Flow can also be increased by applying vacuum to the collection chamber and filter 188. This retrograde flow will carry any dislodged material out of the patient and into a collection chamber. The collection chamber may be a simple syringe or may be any other suitable container. If a syringe is used, withdrawal of the plunger automatically causes a vacuum to induce retrograde flow. After enough volume has been removed, the flow can be stopped by closing the valve to atmosphere pressure or by releasing the vacuum. If desired, after any dislodged material has been removed, the balloons 134, 136 of the evacuation sheath assembly 100 may be temporarily deflated, allowing for a period of antegrade blood flow and perfusion of the vessel 150.

Figure 6E:
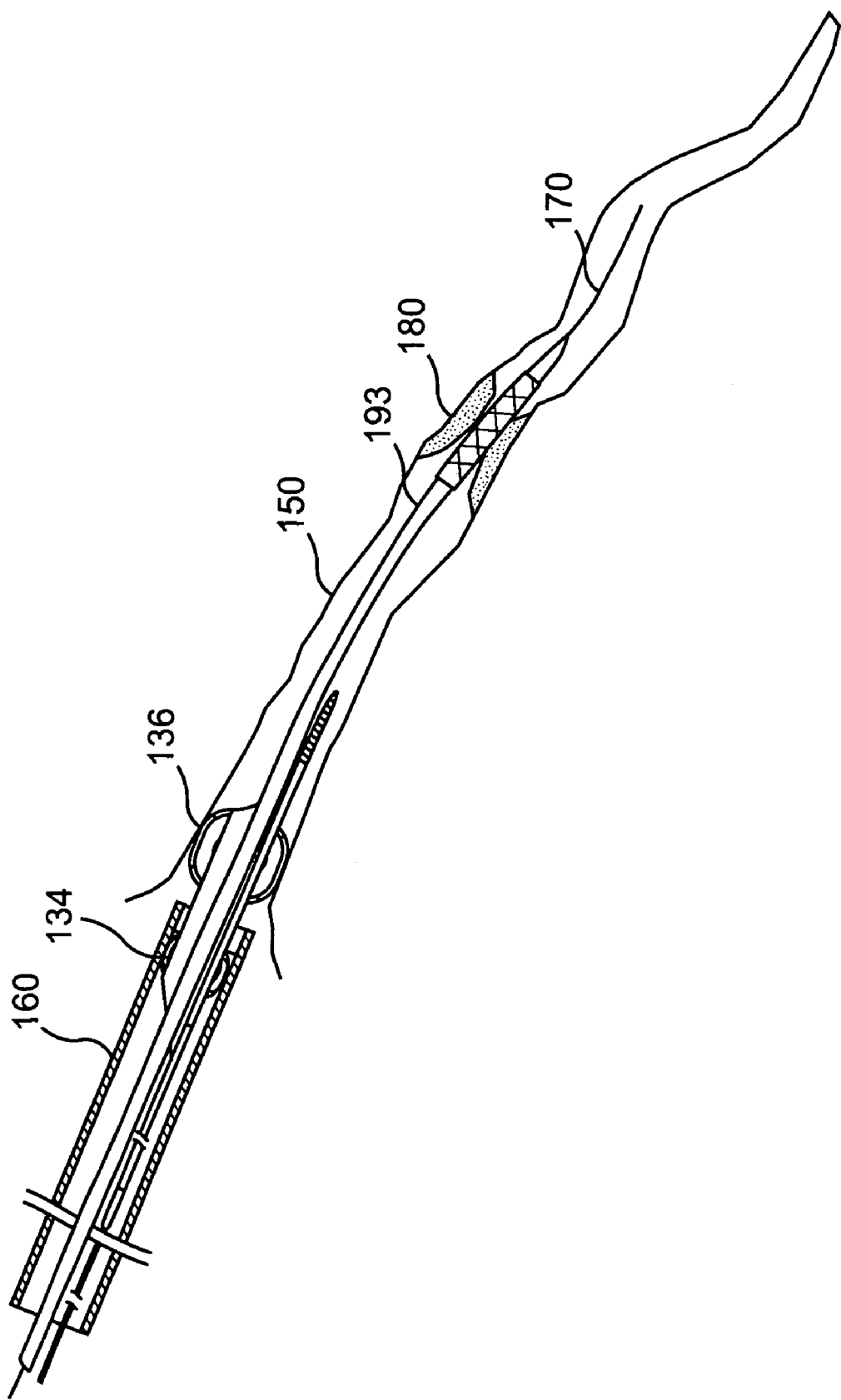

After any dislodged material has been removed, and after normal antegrade blood flow has been allowed, if so desired, all seals are again established. With all seals in place, a therapeutic device such as a stent delivery system 193 is advanced across the stenosis 180 with antegrade flow stopped, as shown in FIG. 6E. The touhy borst valve 184 attached to the guide catheter 160, which is shown in FIG. 5A, seals against the proximal end of the therapeutic device, the guide wire 170 and the proximal shaft portion 110 of the evacuation sheath assembly 100. Alternatively, advancement of the delivery system may be done with retrograde flow. In a step similar to that for the guide wire advancement, some contrast may be delivered into the vessel, allowing continuous visualization of the vessel and stenosis for more precise placement of the stent delivery catheter 193. Again, to effectively keep the contrast in place, the touhy borst valve 184 through which the stent delivery catheter 193 passes must be opened just enough to allow for advancement of the device with little to no backbleeding.

Figure 6F:
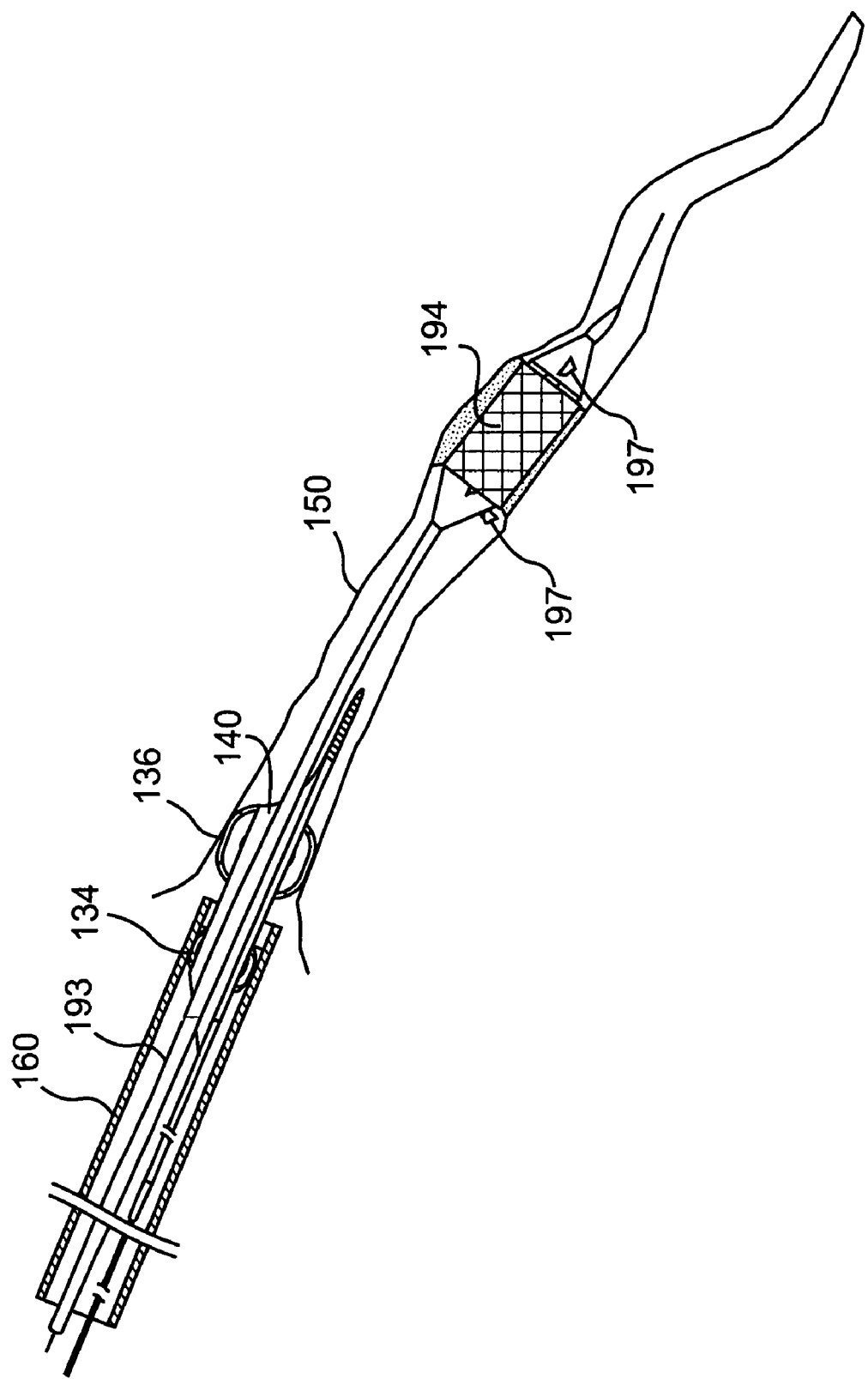

Once the stent delivery system 193 is accurately positioned adjacent the stenosis 180, a stent delivery balloon is inflated to expand a stent 194 against the vessel wall, opening a passage for blood flow through the stenosis 180 (FIG. 6F). During inflation of the stent balloon, retrograde flow (if present) is discontinued by the occlusion of the blood vessel by the therapeutic device and the stoppage of any applied vacuum.

Figure 6G:
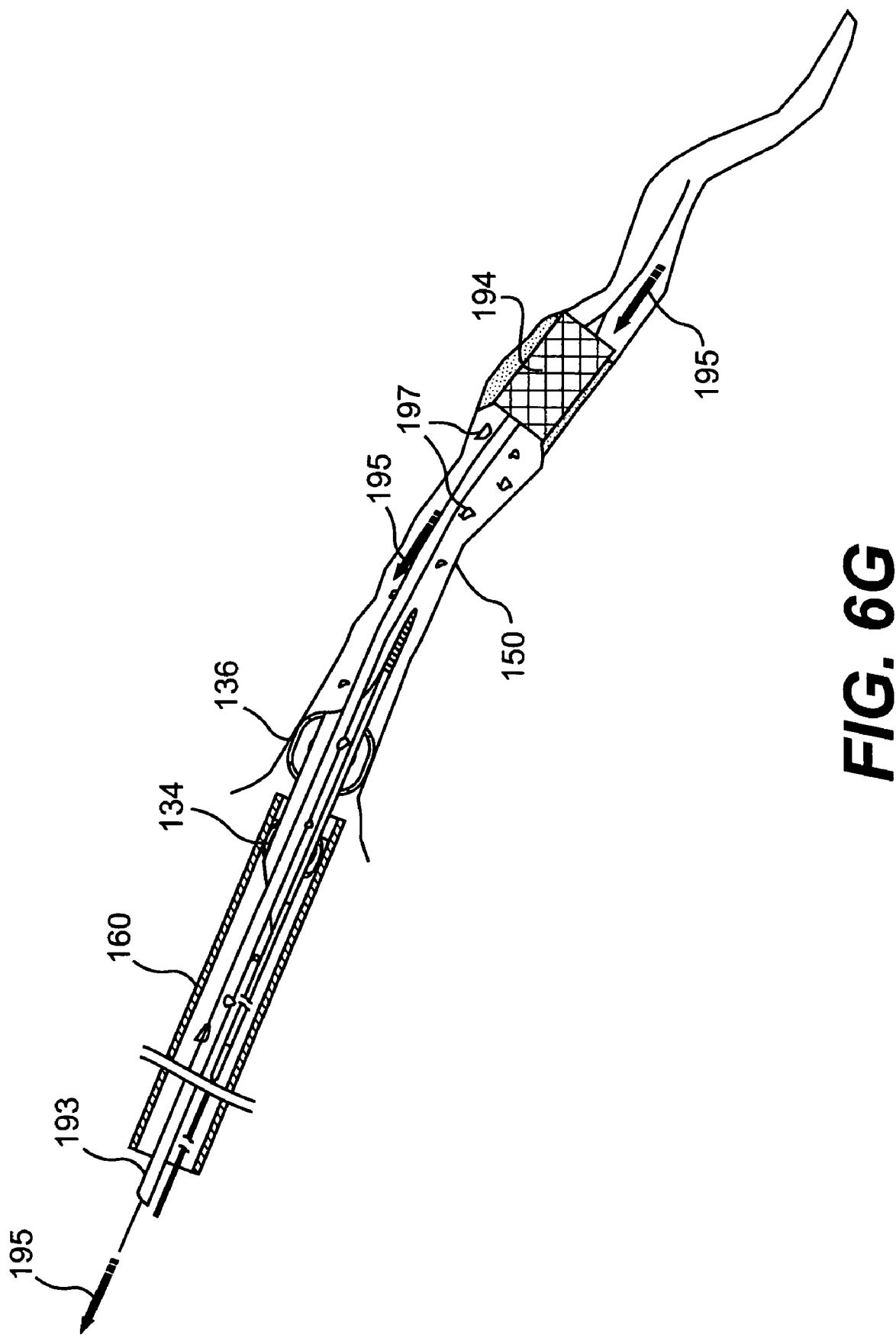

After the stent 194 is applied to the stenosis 180, the stent delivery balloon is deflated and retrograde flow is re-established in the vessel 150. Any embolic material 197 dislodged from the therapeutic site is carried back to the evacuation lumen 140 of the evacuation head 132 by the retrograde flow 195 (FIG. 6G). The embolic material 197 may include material dislodged during advancement of the therapeutic device, or during the expansion of the stent 194, in the case where the therapeutic device includes a stent 194. To remove this potentially embolic debris 197, the retrograde flow 195 is re-established when the therapeutic device is no longer occluding the blood flow, and additional vacuum is preferably applied to the evacuation lumen 140. The therapeutic device may be left in place while there is retrograde flow, or it may be positioned proximal to the stenosis 180, or even brought back within the lumen of the guide catheter 160. In some instances, once the particulate 197 has been removed, additional contrast delivery to the blood vessel may indicate a need for more therapeutic steps, e.g., further dilation of the stent with the balloon. In this, case, it is more convenient to have the balloon catheter already in position for any subsequent use.

Figure 6I:
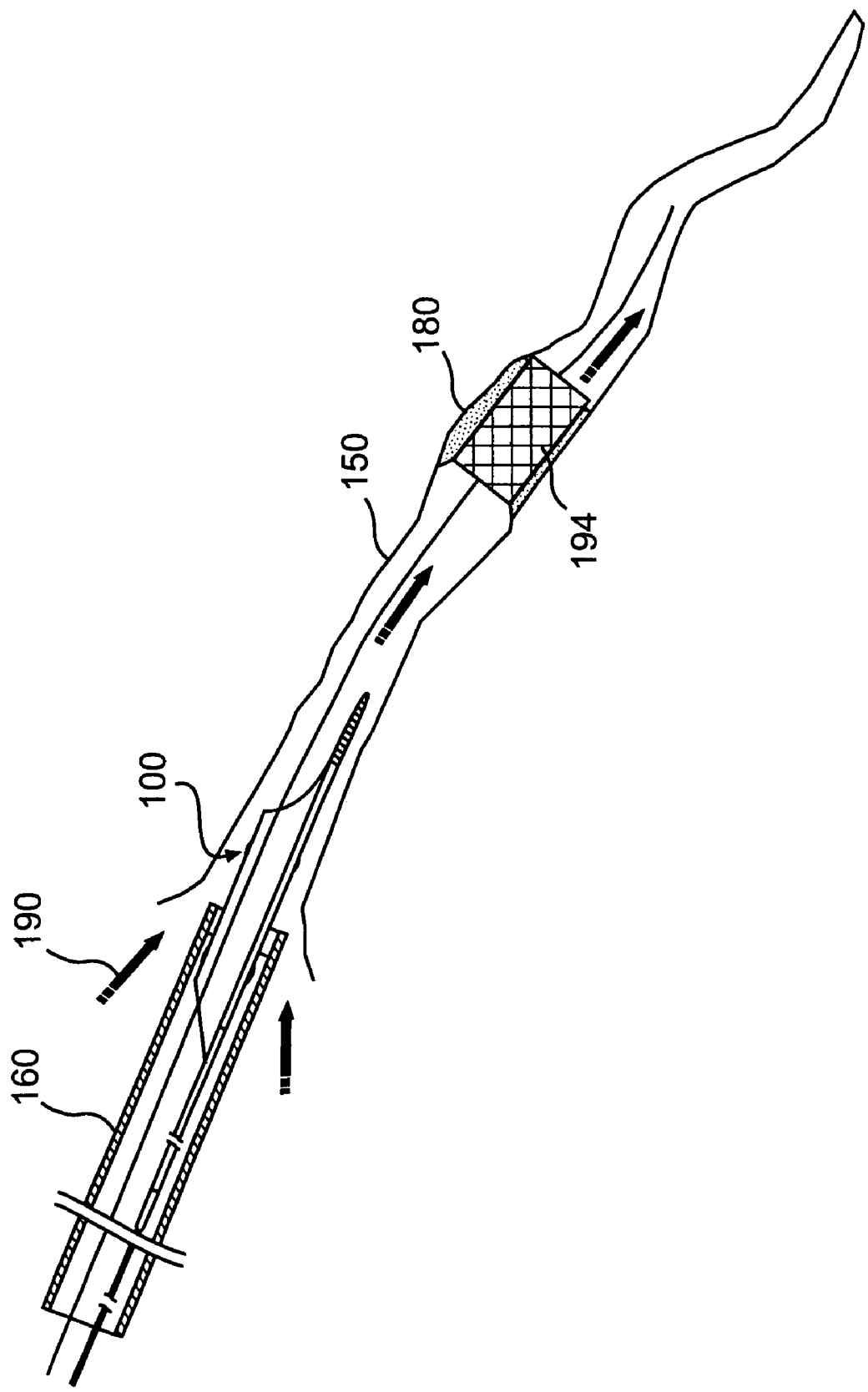

After the embolic material is removed, the therapeutic device is removed from the vessel 150 (retrograde flow may or may not be maintained) (FIG. 6H). The distal and proximal sealing balloons 136, 134 are then deflated (FIG. 6I), establishing normal arterial flow.

According to another aspect of the present invention, the diameter of an evacuation head may be expandable from a first introduction diameter to a second operational diameter. As embodied herein and shown in FIGS. 2A-2D, an evacuation sheath assembly 200 is provided with an expandable evacuation head 232. Many of the elements present in the previous embodiment are also shown in FIGS. 2A-2D and where these elements are substantially the same, similar reference numerals have been used and no detailed description of the element has been provided.

Figure 2E:
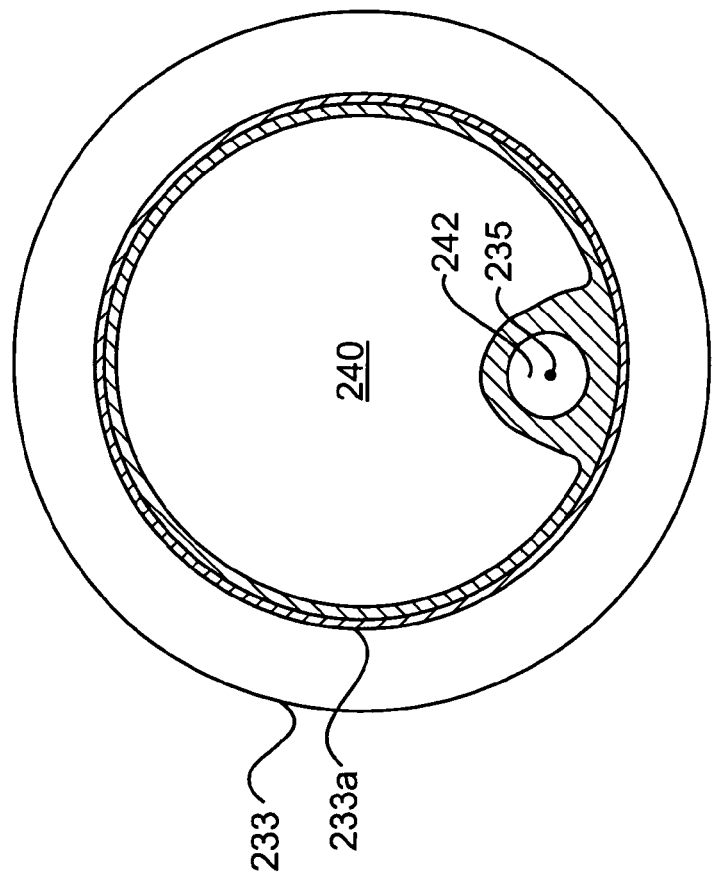
FIG. 2E is a cross-sectional view of the expanded evacuation sheath taken a long line 2E-2E of FIG. 2C.
Figure 2D:
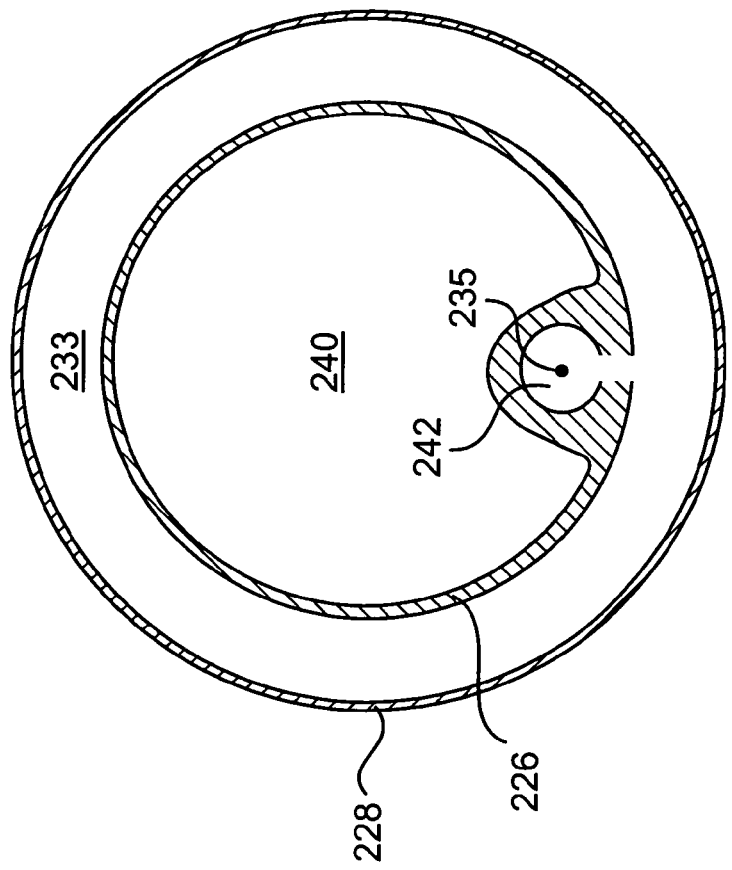
FIG. 2D is a cross-sectional view of the expanded expandable evacuation sheath taken along line 2D-2D of FIG. 2C.

As shown in FIG. 2B, the evacuation head 232 preferably includes an inner layer 226 that will serve as an evacuation lumen and an outer layer 228 that will serve as the sealing surfaces. Preferably, the inner layer 226 is fabricated from polyethylene PET or Pebax, but other suitable materials may be used. The evacuation head 232 has a proximal end 232a and a distal end 232b. FIGS. 2A and 2B show the evacuation head 232 in an unexpanded state and FIGS. 2C, 2D, and 2E show the evacuation head 232 in an expanded state. The inner layer 226 of the evacuation head 232 preferably comprises a tube that unfolds to increase in diameter. In FIG. 2C, the increase in diameter assumes a step-wise shape. Thus, preferably, a distal portion of the inner layer 226 of the evacuation head has an expanded diameter which is larger than a diameter of a guide catheter 260.

The expanded shape of the inner layer 226 of the expandable evacuation head 232 may include a proximal portion having a first diameter and a distal portion having a second diameter, the second diameter being larger than the first such that the inner layer 226 of the evacuation head 232 has a larger dimension in the region which resides within the blood vessel, as shown in FIG. 2C. Alternatively, the diameters of the proximal and distal portions of the inner layer 226 of the evacuation head 232 may be the same, such that the diameter of an expanded inner layer 226 is the same for the region outside of the guide catheter as the region which resides within the guide catheter. In such an embodiment, it would be necessary to provide the distal portion of the evacuation head 232 with a larger or more expansible outer layer, i.e., sealing surface (distal sealing balloon), to ensure a proper seal with blood vessel 250.

The distal and proximal ends of the expanded evacuation head 232 may be angled relative to its longitudinal axis, as discussed with respect to the embodiment shown in FIG. 1A, although this is not shown in FIGS. 2A-2D. The low profile folded delivery state of the evacuation head 232 may not require such angles. Furthermore, if the distal end of the head 232 is not angled relative to the longitudinal axis, the entire open distal end of the expandable evacuation head 232 is suitable for positioning close to the desired therapy site.

The outer layer 228 of evacuation head includes multiple spherical balloons (or balloon regions) 233, including a proximal most balloon 234 and a distal most balloon 236, with a cylindrical waist between each balloon. The inner and outer layers 226, 228 of the evacuation head 232 may be seam welded or bonded together around the circumference at each waist location, while the inner layer 226 is in its expanded condition. Prior to insertion of the evacuation sheath assembly 200 into the guide catheter 260, the evacuation head 232 is folded into its unexpanded condition, as shown in FIGS. 2A and 2B. When fluid, either a gas or liquid, is infused between the inner and outer layers, the outer layer 228 expands radially. As the outer layer 228 expands into multiple balloon regions 233, it pulls the inner layer 226 with it, opening the evacuation lumen 240. Thus, the inner and outer layers expand together in the radial direction when inflated.

As discussed with respect to the embodiment shown in FIGS. 1A-1C, the evacuation head 232 comprises a multi-lumen tube 238 having an evacuation lumen 240 and an inflation lumen 242. As in the embodiment shown in FIGS. 1A-1C, the inflation lumen 242 is in fluid communication with intermediate and proximal shaft portions 210, 220 and is in fluid communication with the individual balloon segments 233, 234, 236, such that when fluid is infused into inflation lumen 242, the evacuation head 232 expands. Further infusion of fluid into the inflation lumen of the evacuation sheath assembly will inflate the distal and proximal sealing balloons until they are appropriately sized to cause effective sealing.

As described previously, in addition to intermediate balloons 233, the evacuation head 232 includes a proximal sealing balloon 234 and a distal sealing balloon 236. The proximal sealing balloon is configured to seal with an inner diameter of the guide catheter 260 and the distal sealing balloon is configured to seal with the inner walls of blood vessel 250. The remaining balloons 233 need only be sized to an inflated diameter sufficient to "pull" open the inner layer 226 of the expandable evacuation head 232. Although three intermediate balloons 233 are shown in FIG. 2C, more or fewer balloons may be provided as appropriate, for example depending upon the length of the evacuation head to be expanded. Although intermediate balloons 233 are intended to "pull" open evacuation lumen 240 of the evacuation head 232, balloons 233 may also provide addition sealing under certain circumstances, as shown in FIG. 2C. However, it is less important that the remaining balloons 233 be elastomeric, as they do not necessarily require a range of expanded diameters.

As shown in FIGS. 2A and 2B, prior to insertion into the guide catheter 260, the evacuation head 232 is folded into a reduced diameter configuration. As illustrated, this folding may be in a generally "w" type fold, however other folding configurations are contemplated, such as "s" folds or "c" folds. It is also preferable to heat set the folded evacuation head 232 in this configuration. Because the evacuation head has been heat set in a folded configuration, once the sealing balloons and remaining balloons are deflated after a procedure, the evacuation head will refold toward its pre-expanded configuration.

The low profile of the evacuation head 232 in its delivery configuration and the soft tip 244 at the end of evacuation sheath assembly 200 allow the expandable evacuation sheath assembly 200 to be passed through smaller and more tortuous lumens and blood vessels. The expandable evacuation lumen 240 also allows the evacuation sheath assembly 200 to be sized more closely to the guiding catheter 260 and larger than the guiding catheter 260 in the portion that is placed distal of the guiding catheter when it is in the expanded state. This larger lumen allows for high evacuation flow rates, and eases the ability for large particles to be removed from the blood vessel during or subsequent to the therapeutic procedure, while having a relatively small collapsed delivery condition.

In use, the evacuation sheath assembly 200 is deployed in a similar manner as discussed with respect to evacuation sheath assembly 100. The steps for using evacuation sheath assembly 200 with a guide catheter 260 in a vessel 250 are sequentially depicted in FIGS. 7A-7I.

Figure 7A:
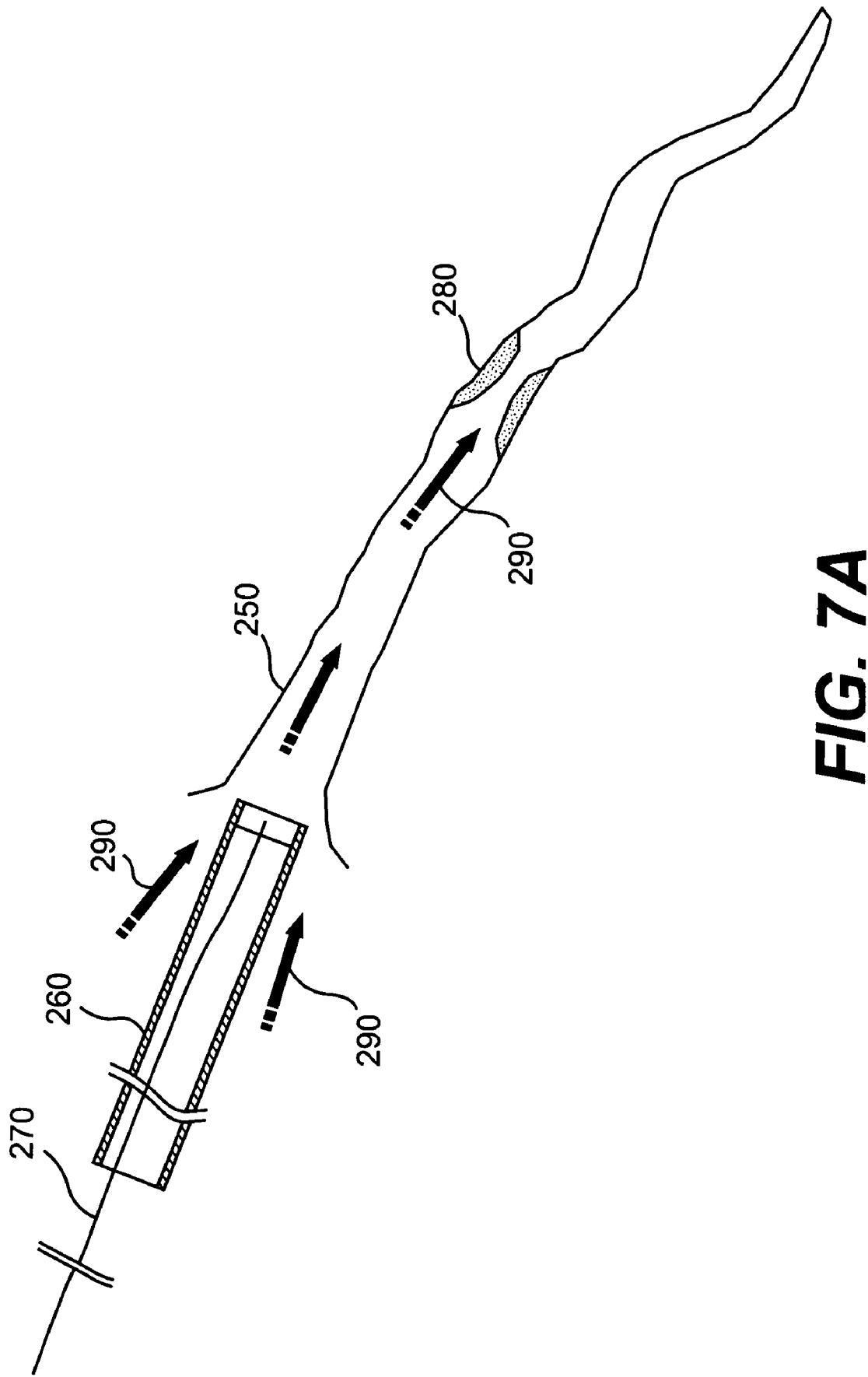
Figure 7B:
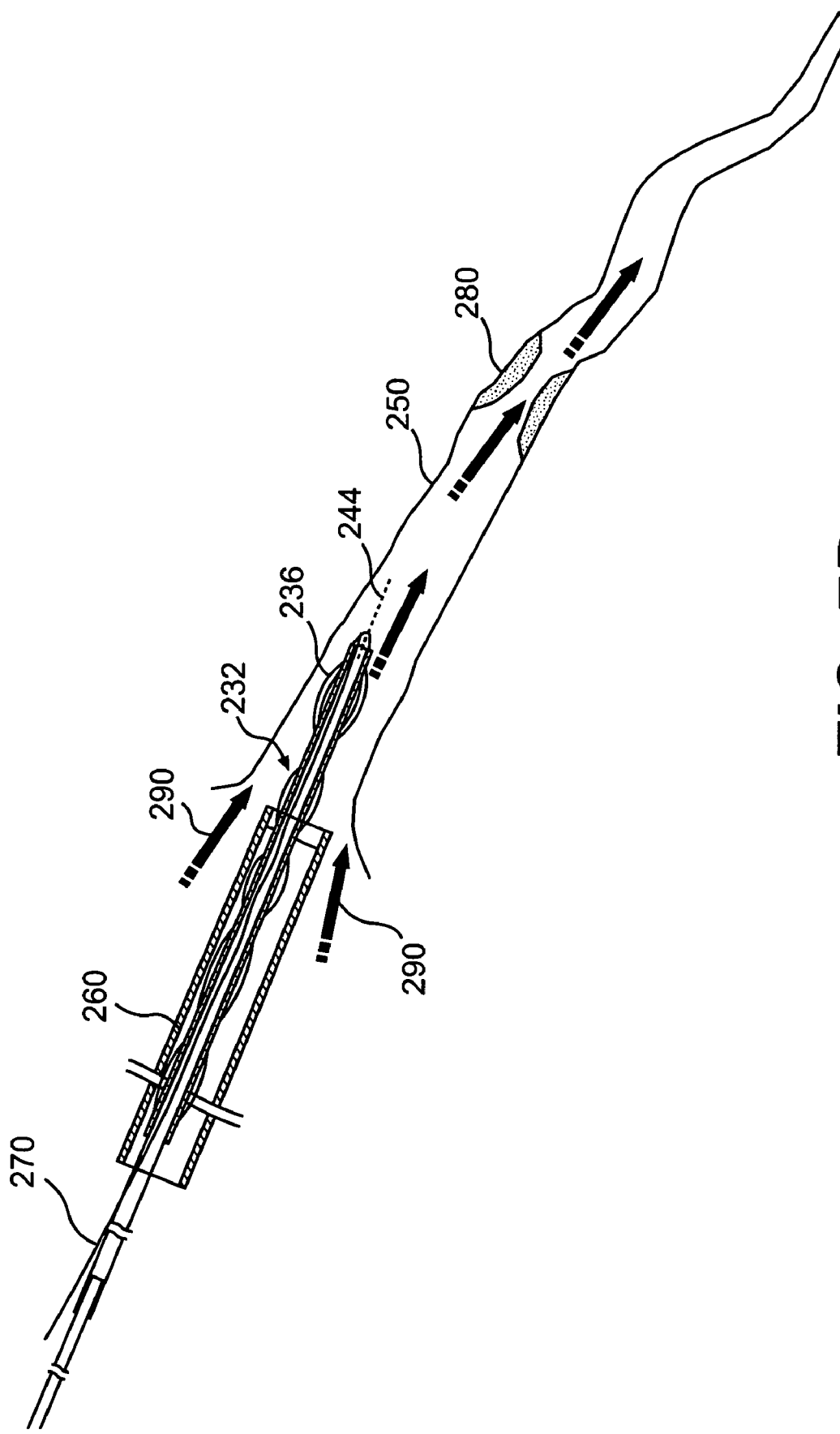
Figure 7C:
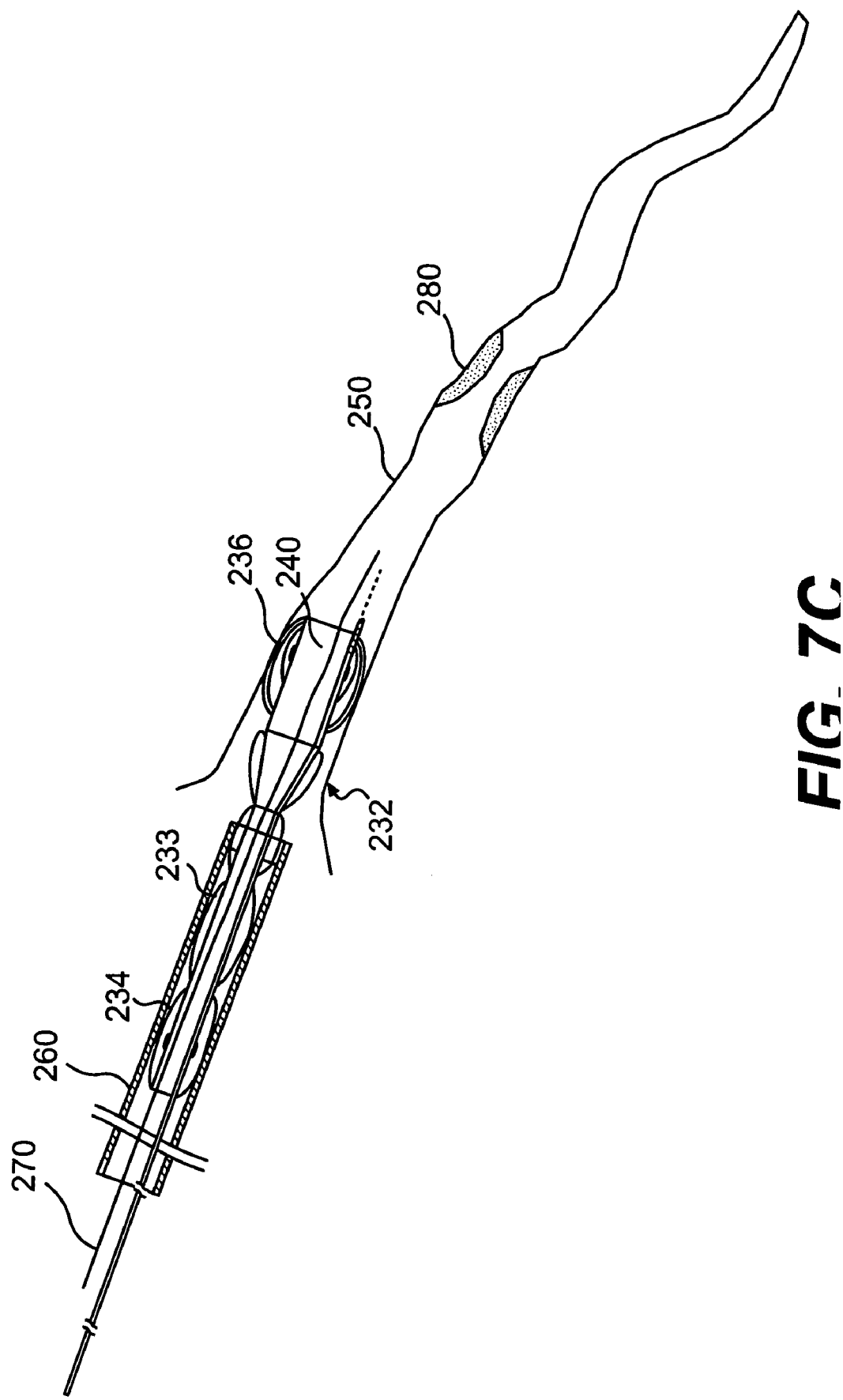
Figure 7D:
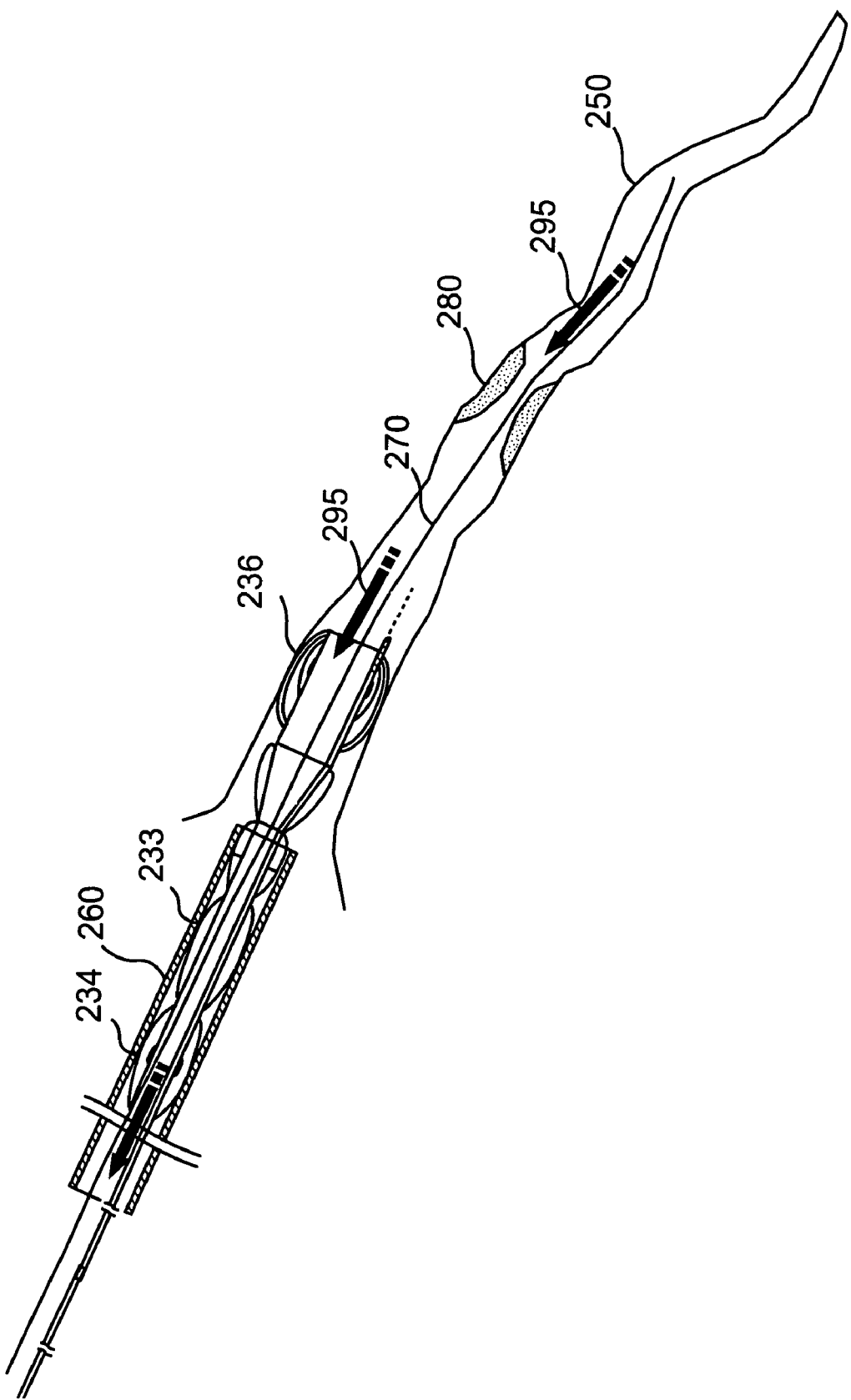
Figure 7E:
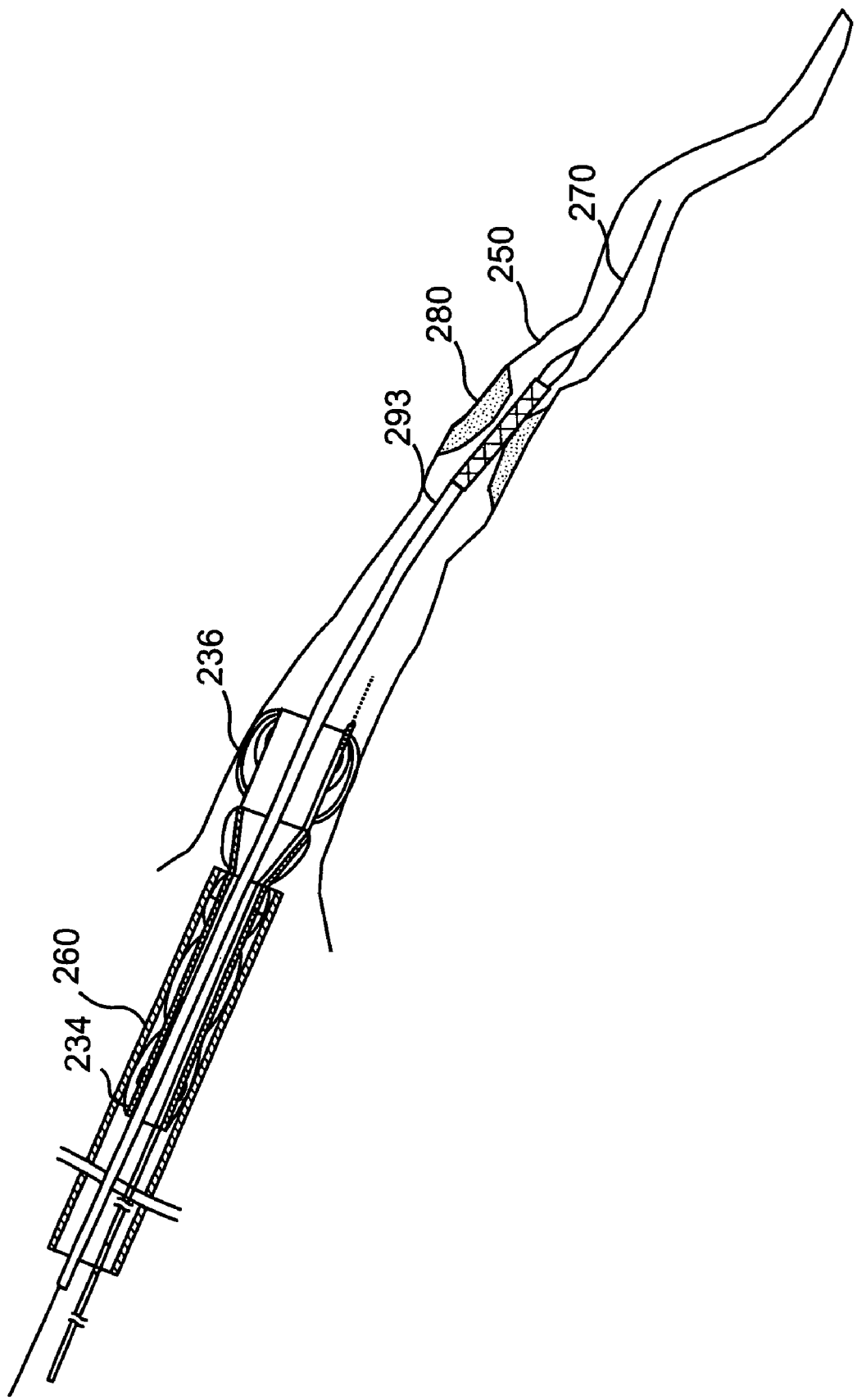
Figure 7F:
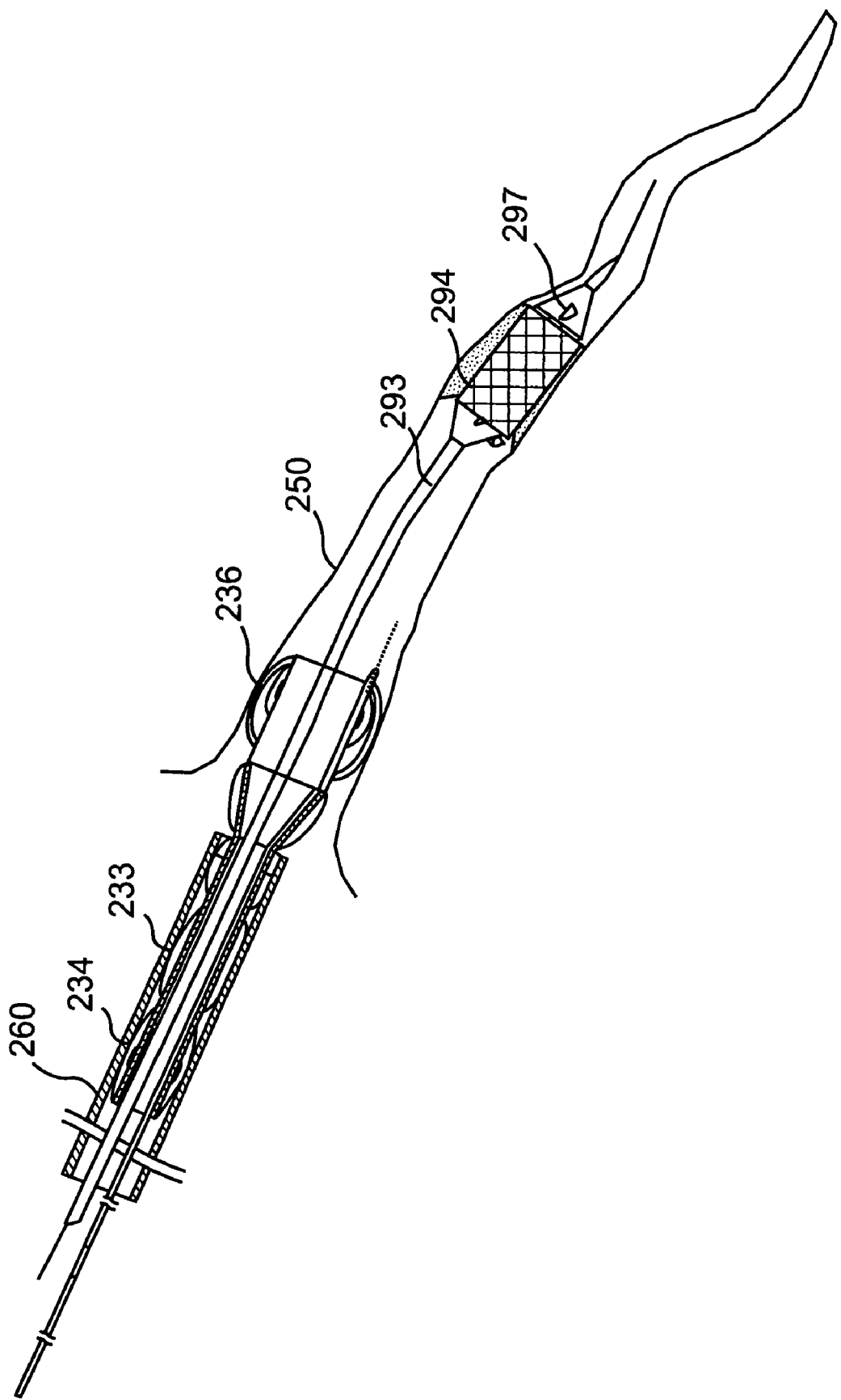
Figure 7G:
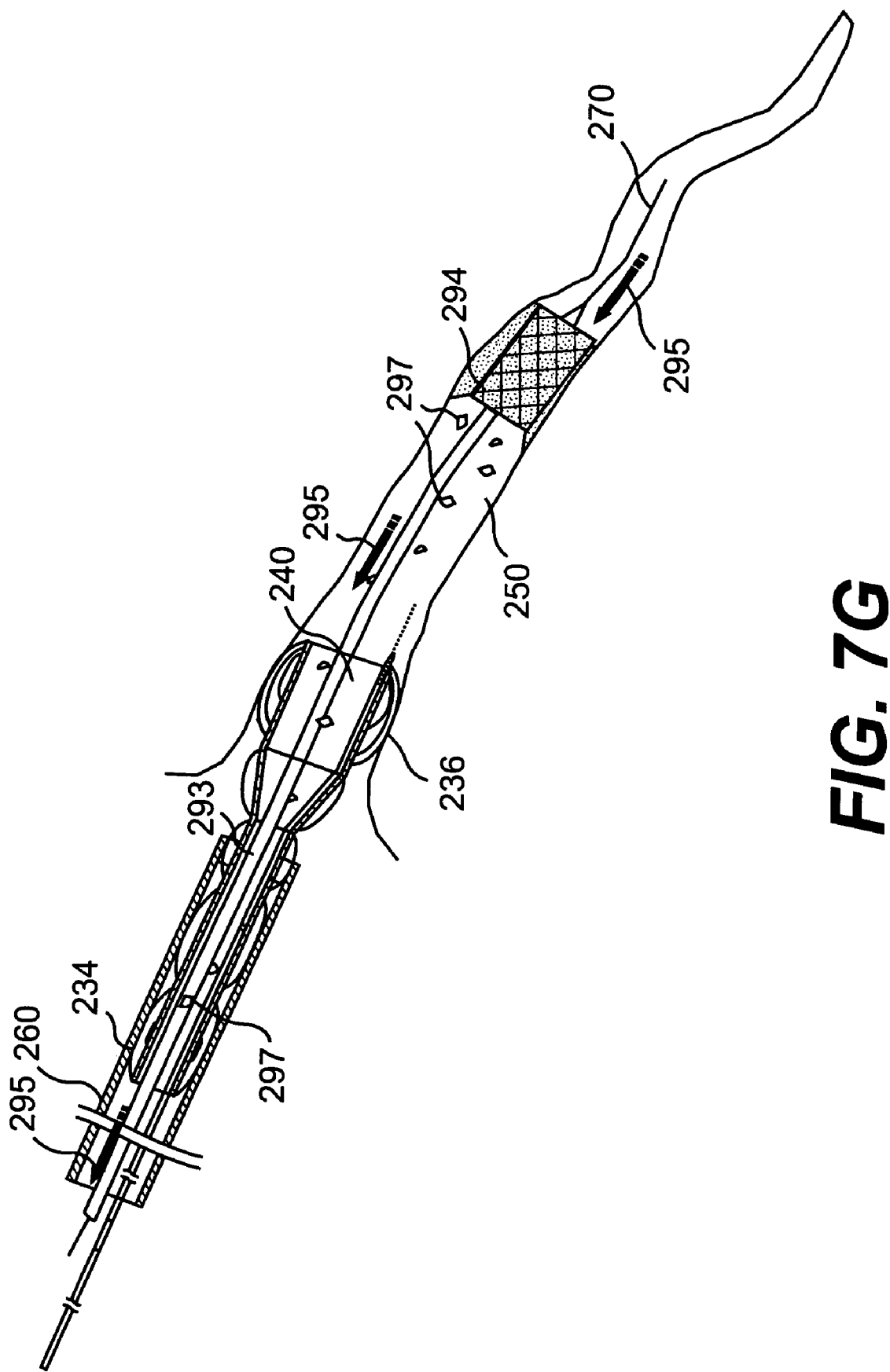
Figure 7H:
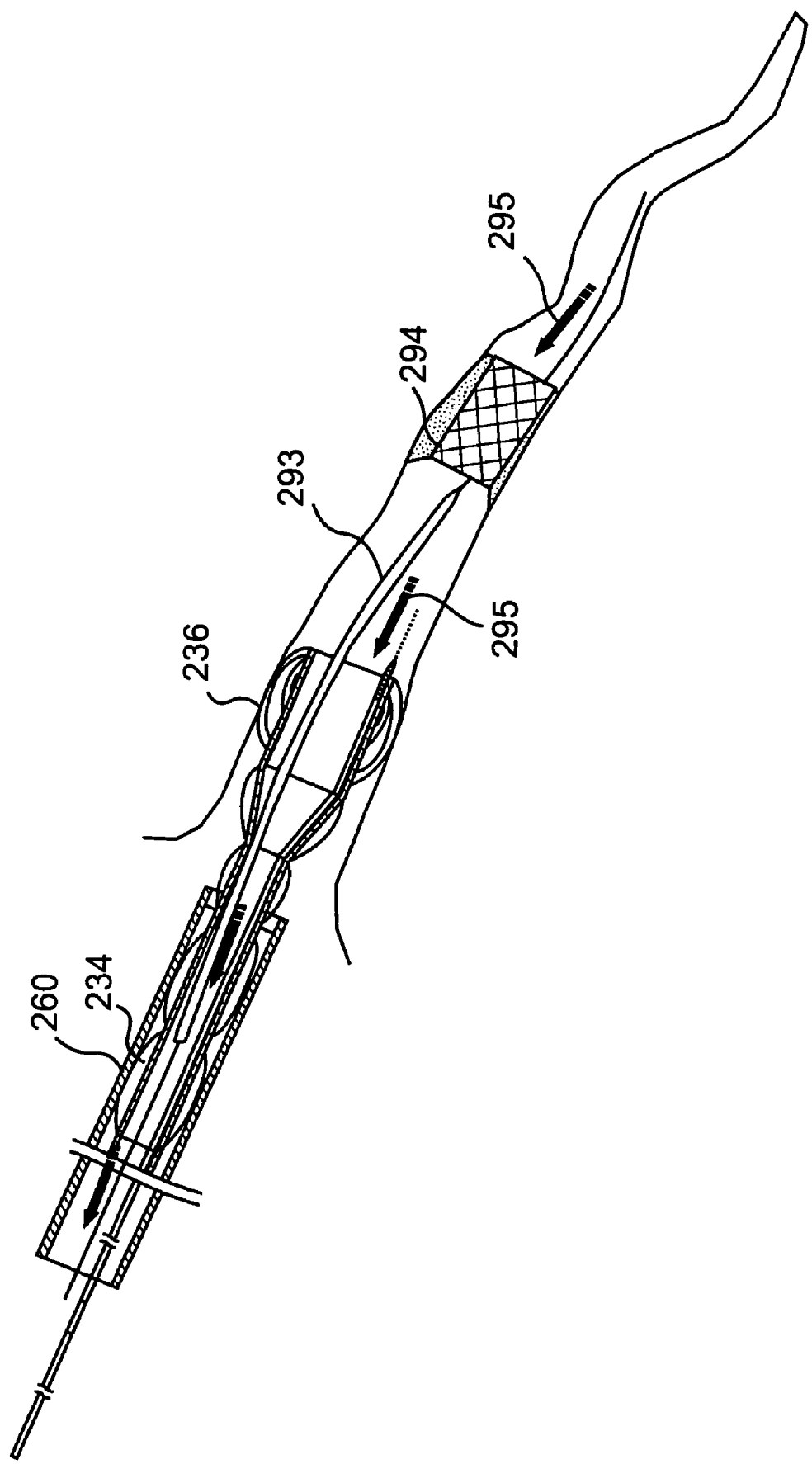
Figure 71:
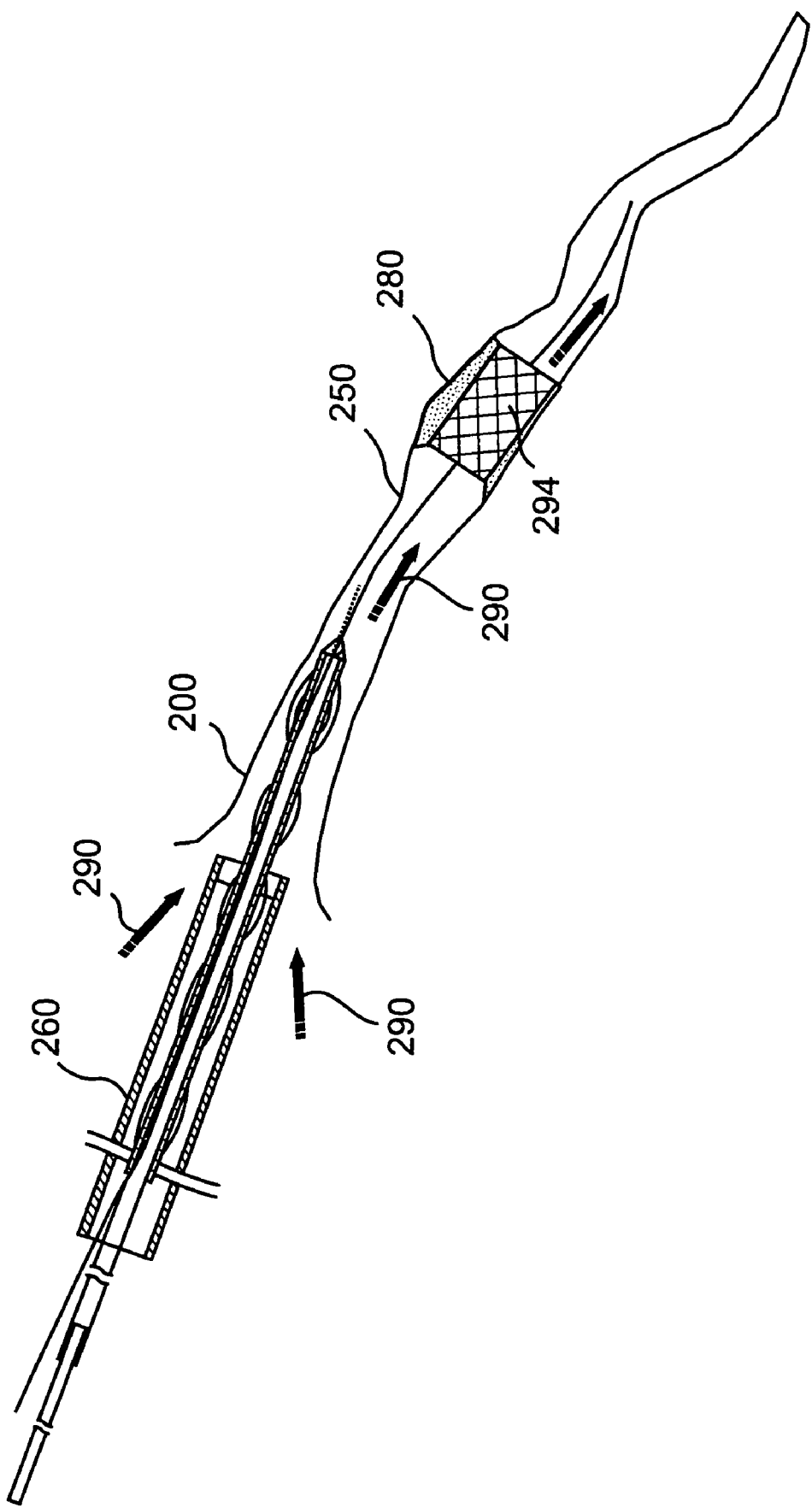

As shown in FIG. 7A, guide catheter 260 and guide wire 270 are advanced proximate to a blood vessel 250. Subsequently, evacuation sheath assembly 200, with evacuation lumen 240 in its delivery configuration, is advanced over the guidewire 270 into guide catheter 260 and blood vessel 250 (FIG. 7B). Once evacuation head 232 is properly positioned, as can be verified using proximal markers 115 and markers 246a, 246b, evacuation head 232 is expanded (FIG. 7C) until evacuation lumen 240 is open. Fluid continues to be injected into the balloons until proximal balloon 234 creates a seal with the lumen of guide catheter 260 and until distal balloon 236 creates a seal with blood vessel 250. After the proper seals are established, the stenosis 280 is treated and any embolic debris 297 is removed via retrograde flow 295 (FIGS. 7C-7H), as previously described with respect to FIGS. 6C-6H. After treatment, evacuation head 232, including proximal and distal sealing balloons 234, 236, is deflated and then removed from blood vessel 250 (FIG. 7I).

According to another aspect of the present invention, the evacuation head may comprise an elongated multi-lumen tube. As embodied herein and shown in FIGS. 3A and 3B, an evacuation sheath assembly 300 is provided with an evacuation head 332. Many of the elements present in the previous embodiments are also shown in FIGS. 3A and 3B and where these elements are substantially the same, similar reference numerals have been used and no detailed description of the element has been provided.

Figures 3A, 3B:
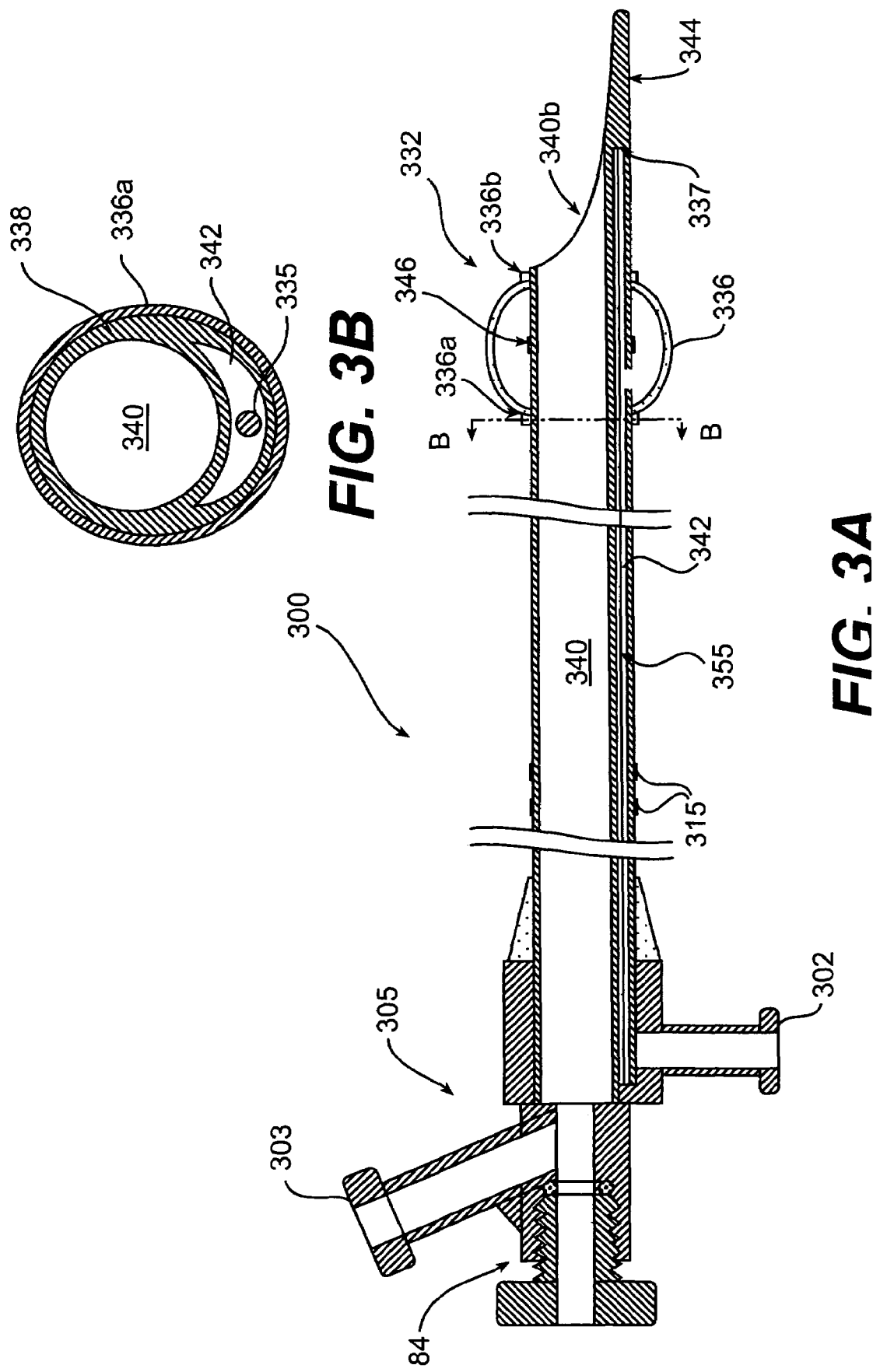
FIG. 3A is cross-sectional side view of a full-length evacuation sheath according to another embodiment of the present invention.
FIG. 3B is cross-sectional view of the full-length evacuation sheath taken along line 3B-3B of FIG. 3A.
Figure 5C:
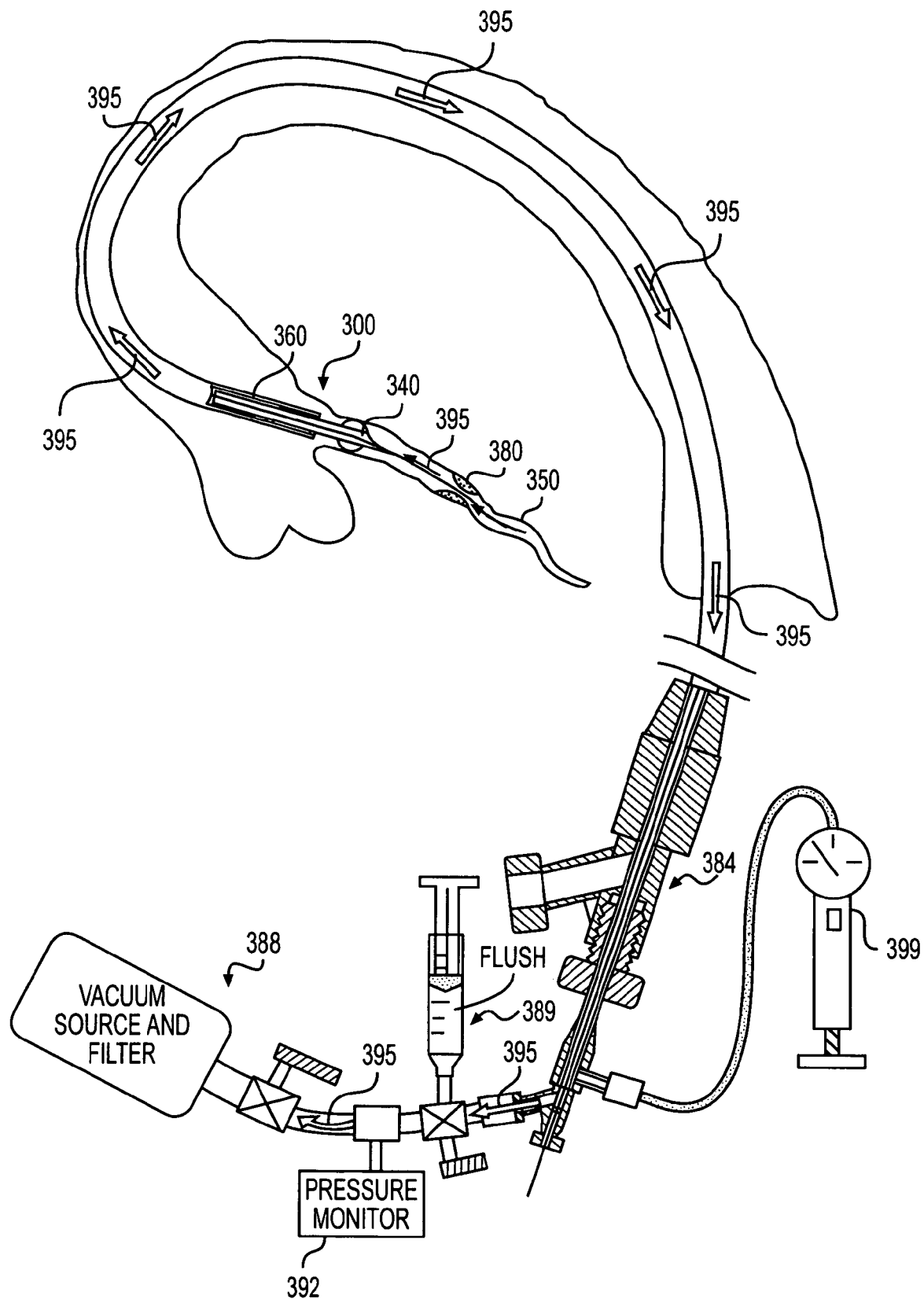
FIG. 5C is cross-sectional view of the full-length evacuation sheath of FIGS. 3A and 3B deployed within a vessel.

As shown in FIG. 3A, evacuation head 332 includes a single elongated multi-lumen tube 338. The size of the tube 338 allows it to be placed through a guiding catheter 360 and into a blood vessel 370 (see FIG. 5C). The tube may be made from a polymer such as polyethylene or Pebax® material or materials described with respect to FIG. 1A. In addition, the tube 338 may include a coil or braid, as in FIG. 1C, in all or only portions of the tube. The multi-lumen tube 338 includes two lumens 340, 342. The larger of the lumens, the evacuation lumen 340, is designed to allow for the passage of interventional devices such as, but not limited to stent delivery systems and angioplasty catheters. The lumen is also designed to allow for fluid flow, such as blood, blood/solid mixtures, radiographic dye and saline, within the lumen as discussed with respect to FIGS. 1A-1C.

A distal end of the tube 338 is tapered into a soft tip 344, as described in connection with previous embodiments. The soft tip 344 allows the evacuation sheath assembly 300 to be placed more smoothly into the blood vessel. The tube 338 includes inflation lumen 342, which allows for fluid communication between the proximal end of the evacuation sheath assembly 300 and an expandable sealing surface. The elongated multi-lumen tube 338 defines the entire evacuation lumen 340, unlike the devices shown in FIGS. 1A-2D which make use of a significant length of the lumen of the guide catheter for evacuation. For this reason, only a single expandable sealing surface is required.

The expandable sealing surface is preferably a distal sealing balloon 336. Distal sealing balloon 336 may comprise an elastomeric material such as polyurethane or silicone. The distal sealing balloon 336 is configured be positioned distal of the distal tip of a guiding catheter 360 and inflated against the blood vessel 350 causing a fluid tight seal between the blood vessel 350 and the balloon 336. Radiopaque marker 346 is preferably placed at the site of the sealing balloon 336. The radiopaque marker 346 allows the operator to radiographically position the sealing balloon 336 in the proper location within the blood vessel 350. A proximal shaft portion 310 of the evacuation sheath assembly 300 is sealed against a valve 384, such as a touhy borst valve, on the guide catheter 360 creating a fluid tight seal against the evacuation sheath assembly 300 and the guiding catheter 360.

The tube 338 includes proximal markers 315 placed on the exterior of the proximal portion of the tube 338. These markers 315 are positioned to indicate that the tube 338 has been advanced through the guiding catheter 360 to a location where the distal end of the evacuation sheath assembly 300 is just proximal to the distal end of the guiding catheter 360. A proximal portion of the tube 338 is secured to a bifurcated luer hub 305 by an overlapping weld or bond joint. The bifurcated luer hub 305 includes an inflation port 302 and a vacuum port 303 which allows the evacuation sheath assembly 300 to be connected to an inflation apparatus and a vacuum source, respectively.

In use, the evacuation sheath assembly 300 is deployed in a similar manner to that discussed with respect to evacuation sheath assembly 100. The steps of using evacuation sheath assembly 300 with a guide catheter 360 in a vessel 350 are sequentially depicted in FIGS. 8A-8I. The differences between the method discussed with respect to evacuation sheath assembly 100 and that for evacuation sheath assembly 300 are discussed below.

Because the lumen in evacuation sheath assembly 300 runs the full length of evacuation sheath assembly 300, the evacuation sheath assembly 300 should be inserted together with the coronary guide wire 370. Also, because the lumen of the guide catheter 360 is more fully obstructed by this evacuation sheath assembly 300, it is preferable to inject contrast directly into the proximal end of the evacuation lumen 340 of the evacuation sheath assembly 300 (or into both lumen 340 and the lumen of guide catheter 360), rather than just into the lumen of the catheter 360. Also, both the guide catheter lumen and the evacuation lumen 340 can be used for pressure monitoring, although it is more desirable to use the evacuation lumen 340 for pressure monitoring to confirm a tight seal between the distal balloon 336 and blood vessel 350 as needed. As opposed to the earlier discussed embodiments, only one sealing balloon 336 is used to provide the seal in the evacuation sheath assembly 300, as shown in FIGS. 8C-8H.

Figure 8B:
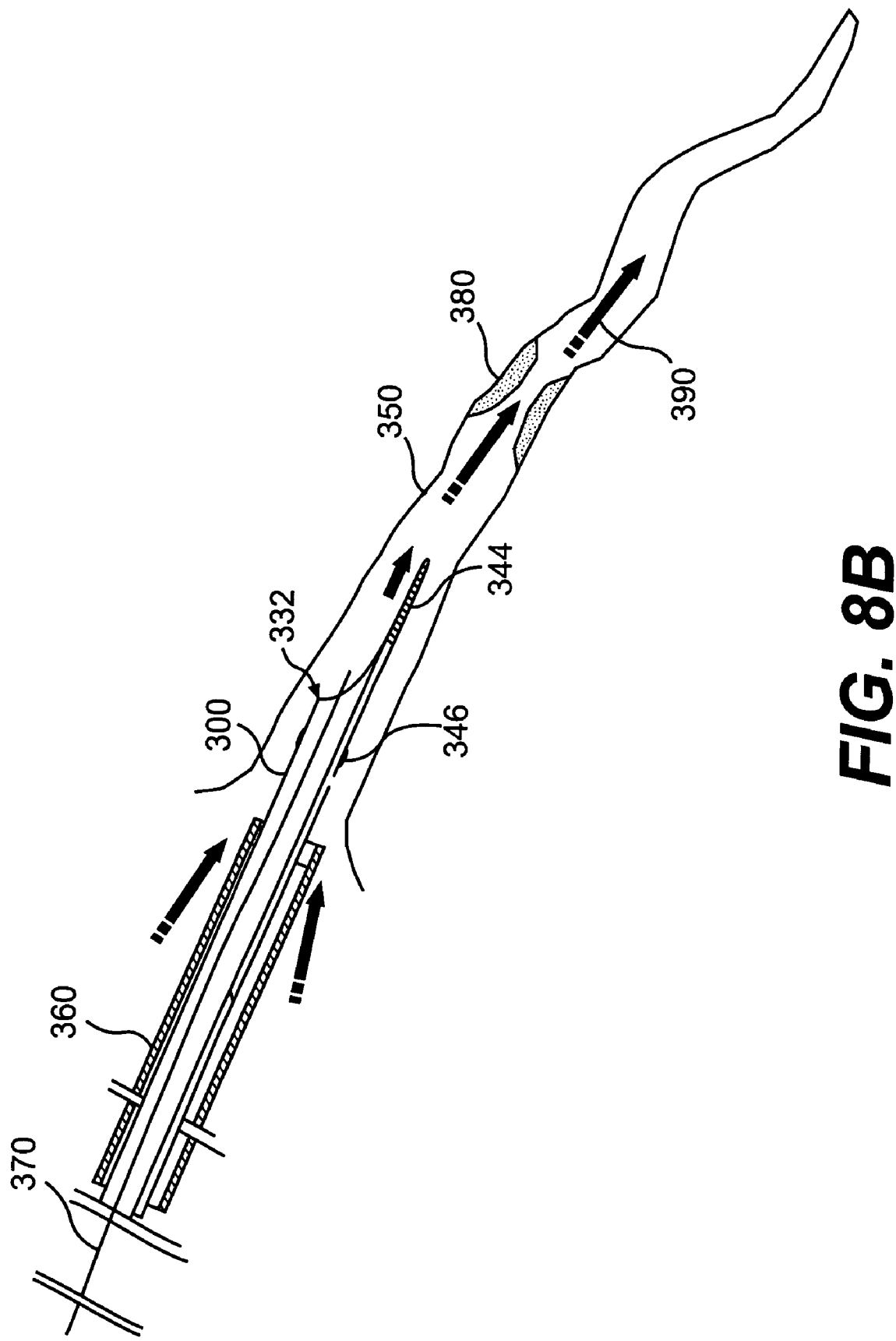
Figure 8C:
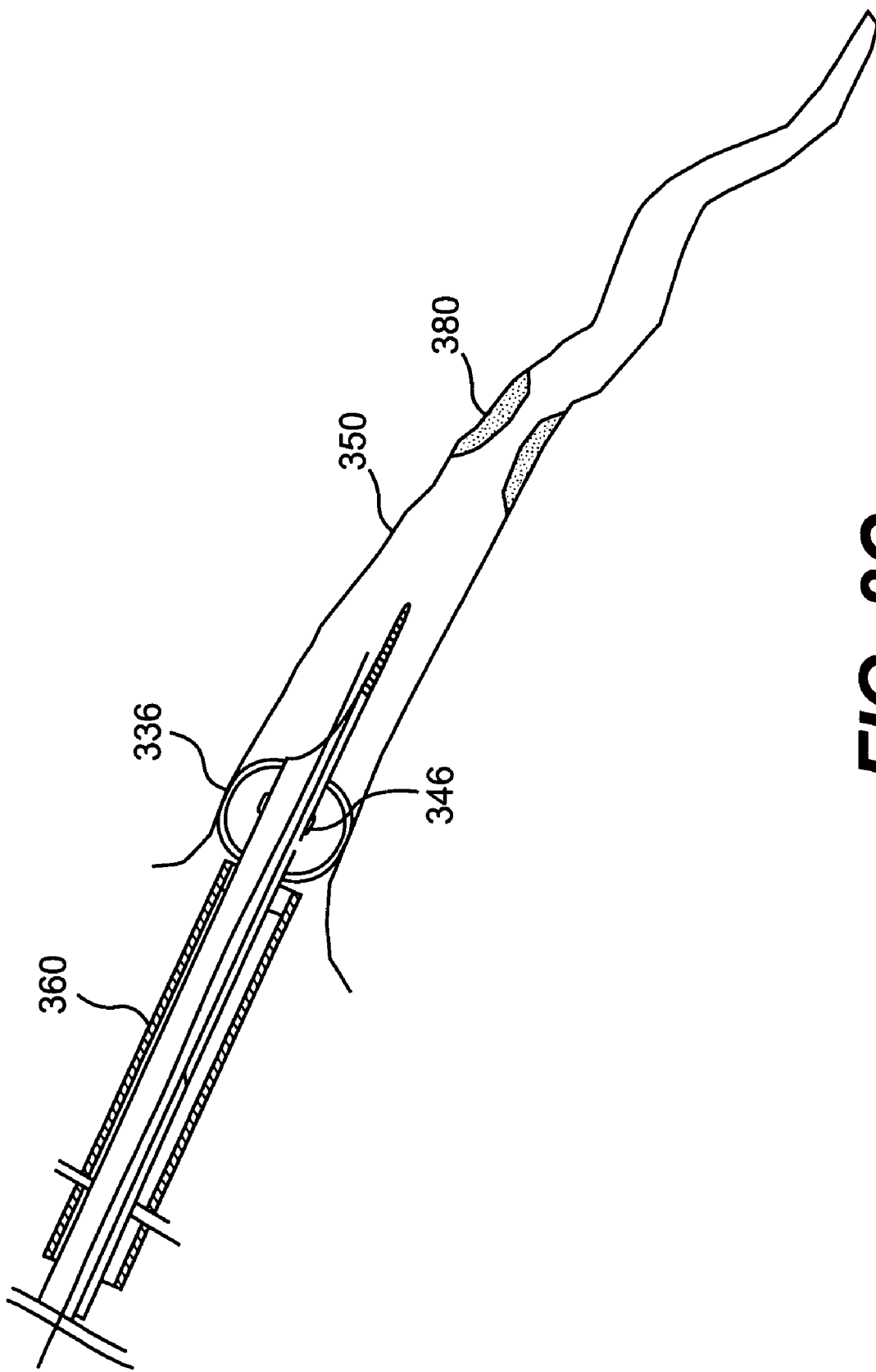
Figure 8D:
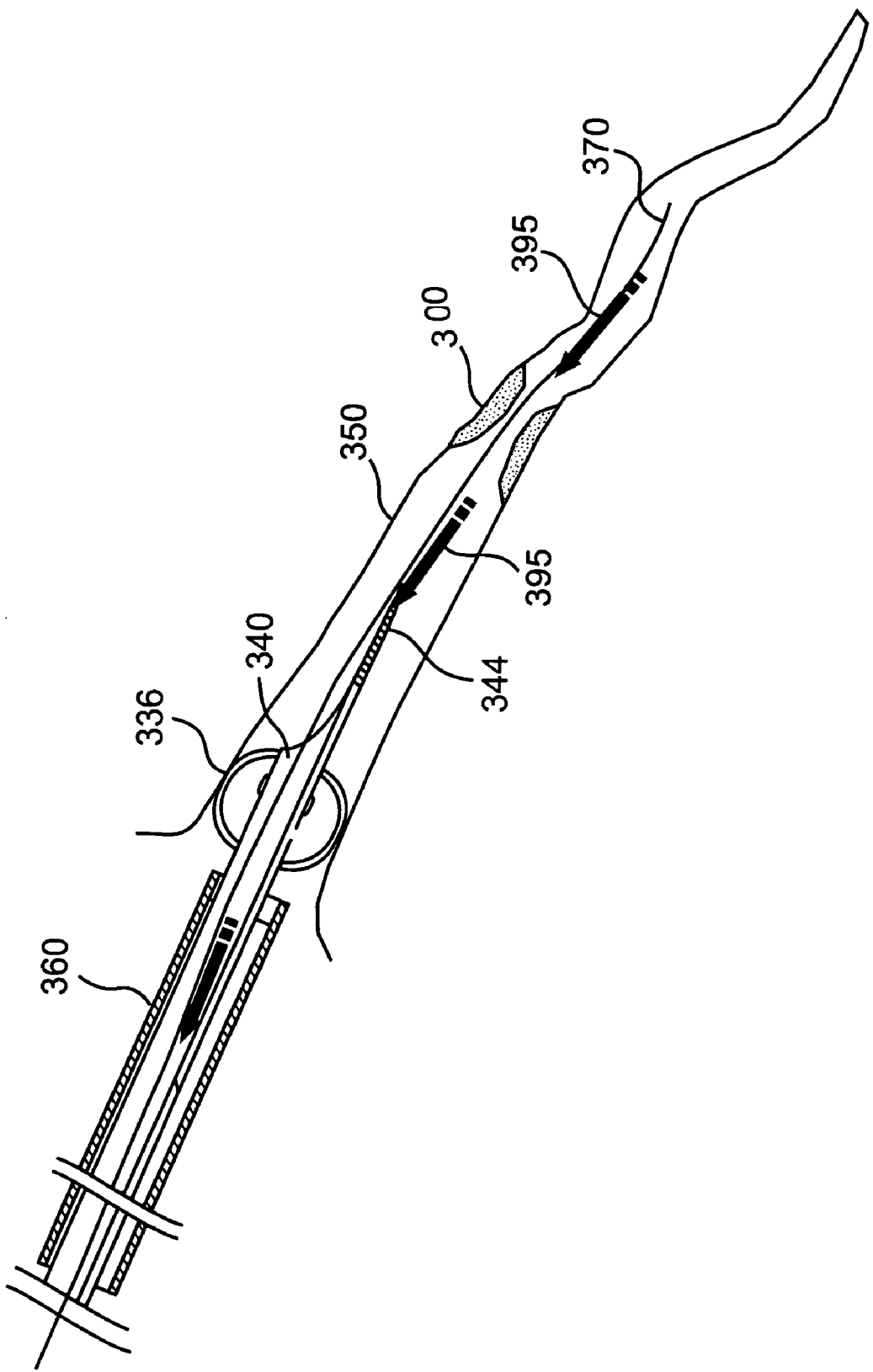
Figure 8E:
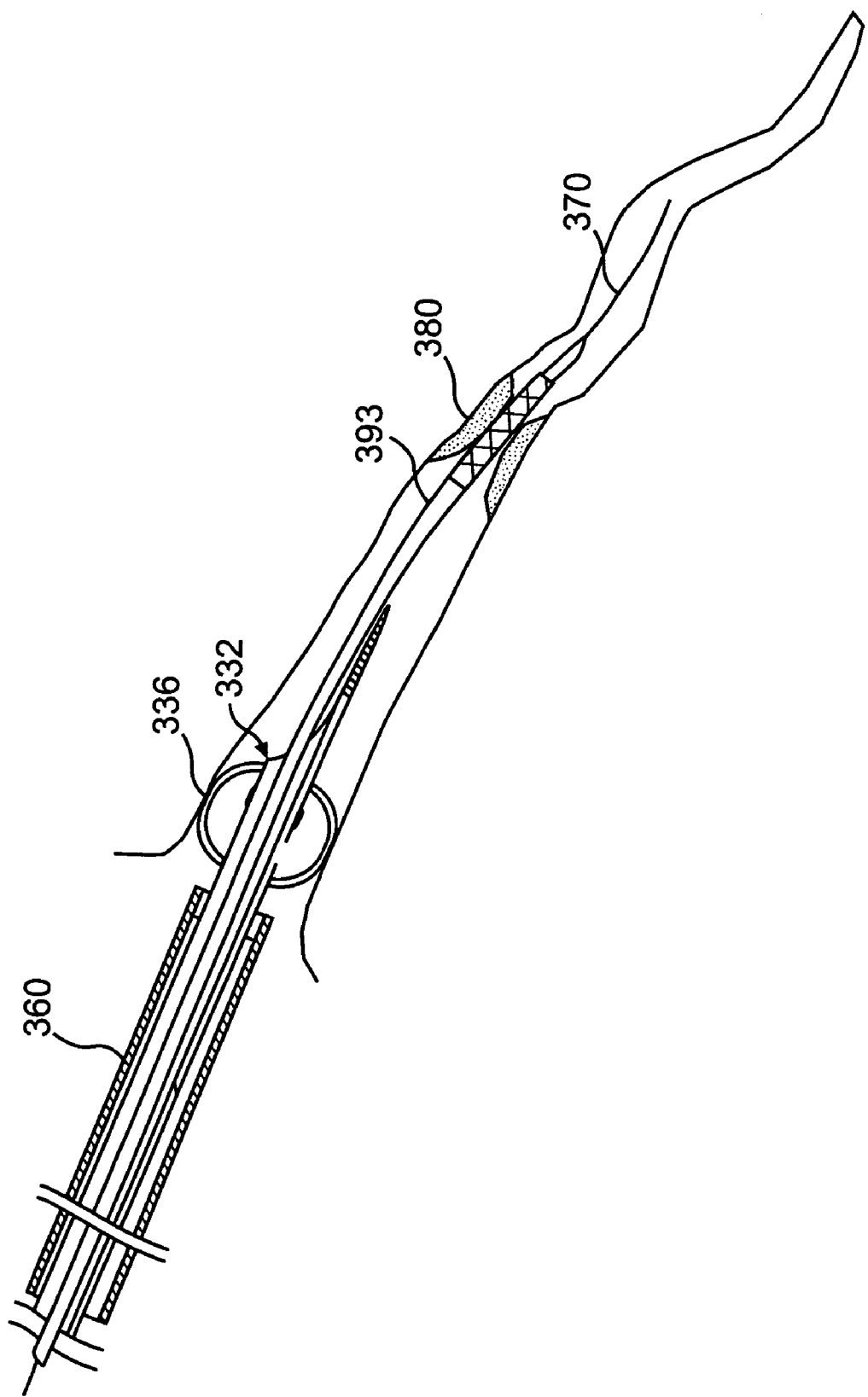
Figure 8F:
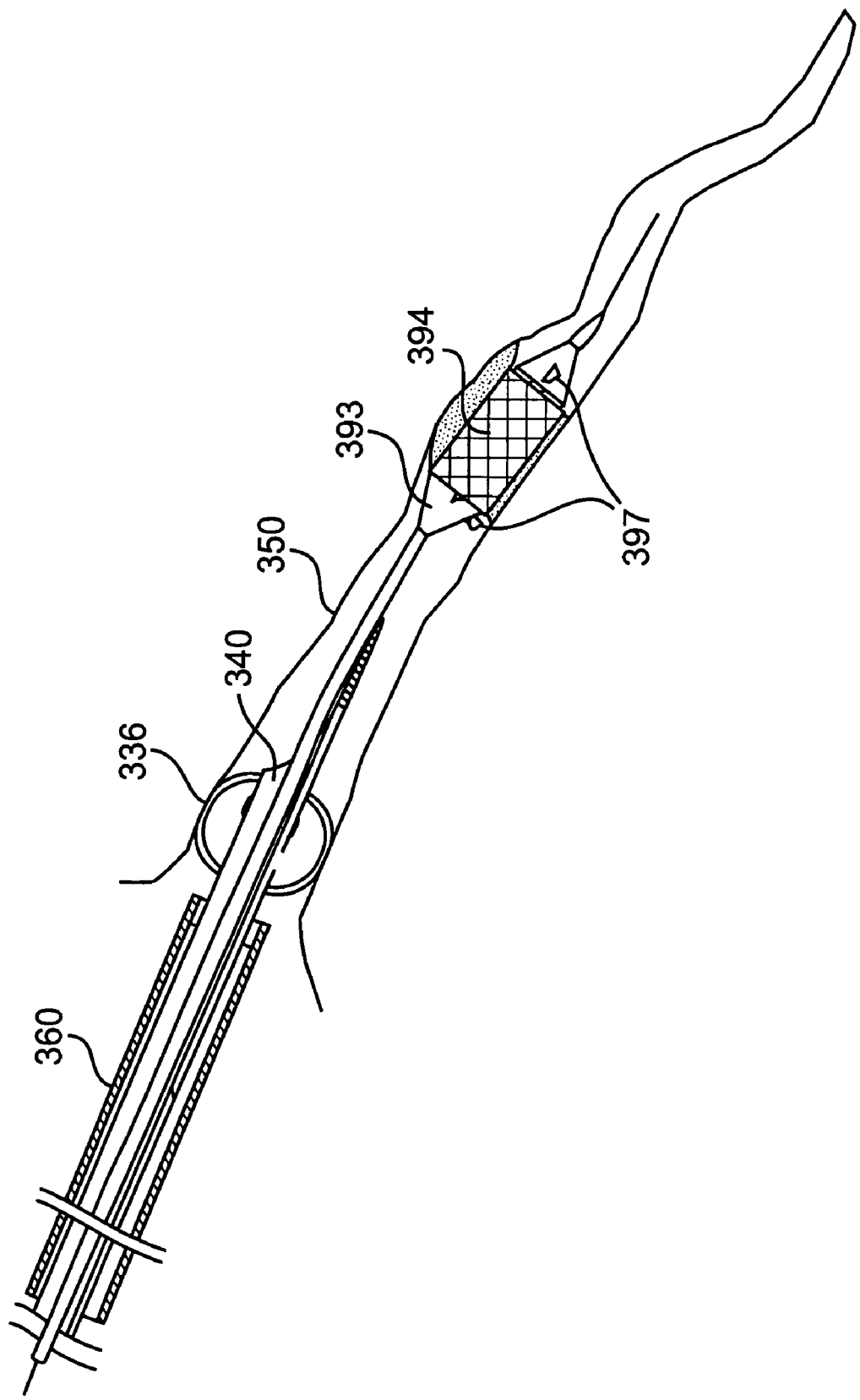
Figure 8G:
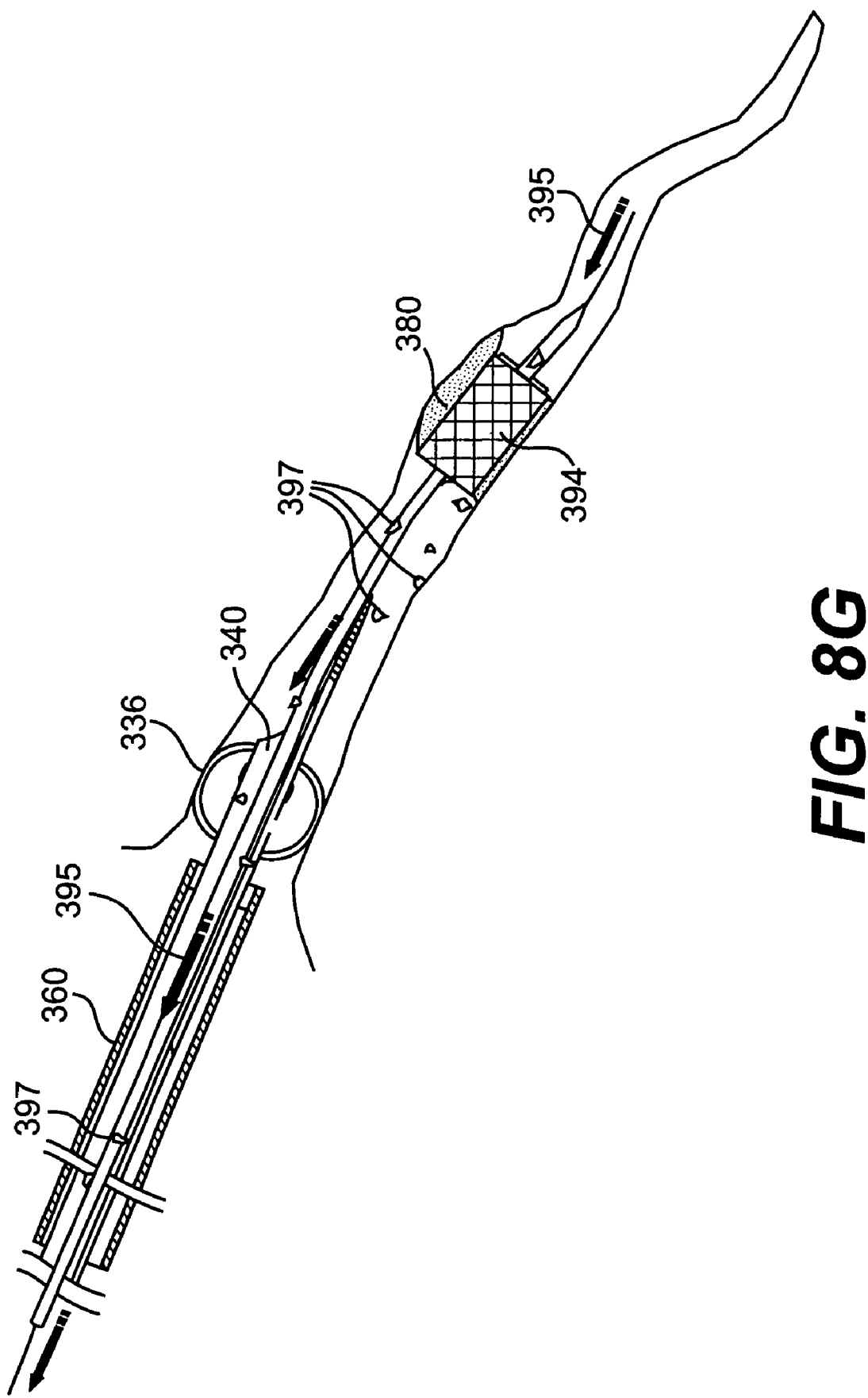
Figure 8H:
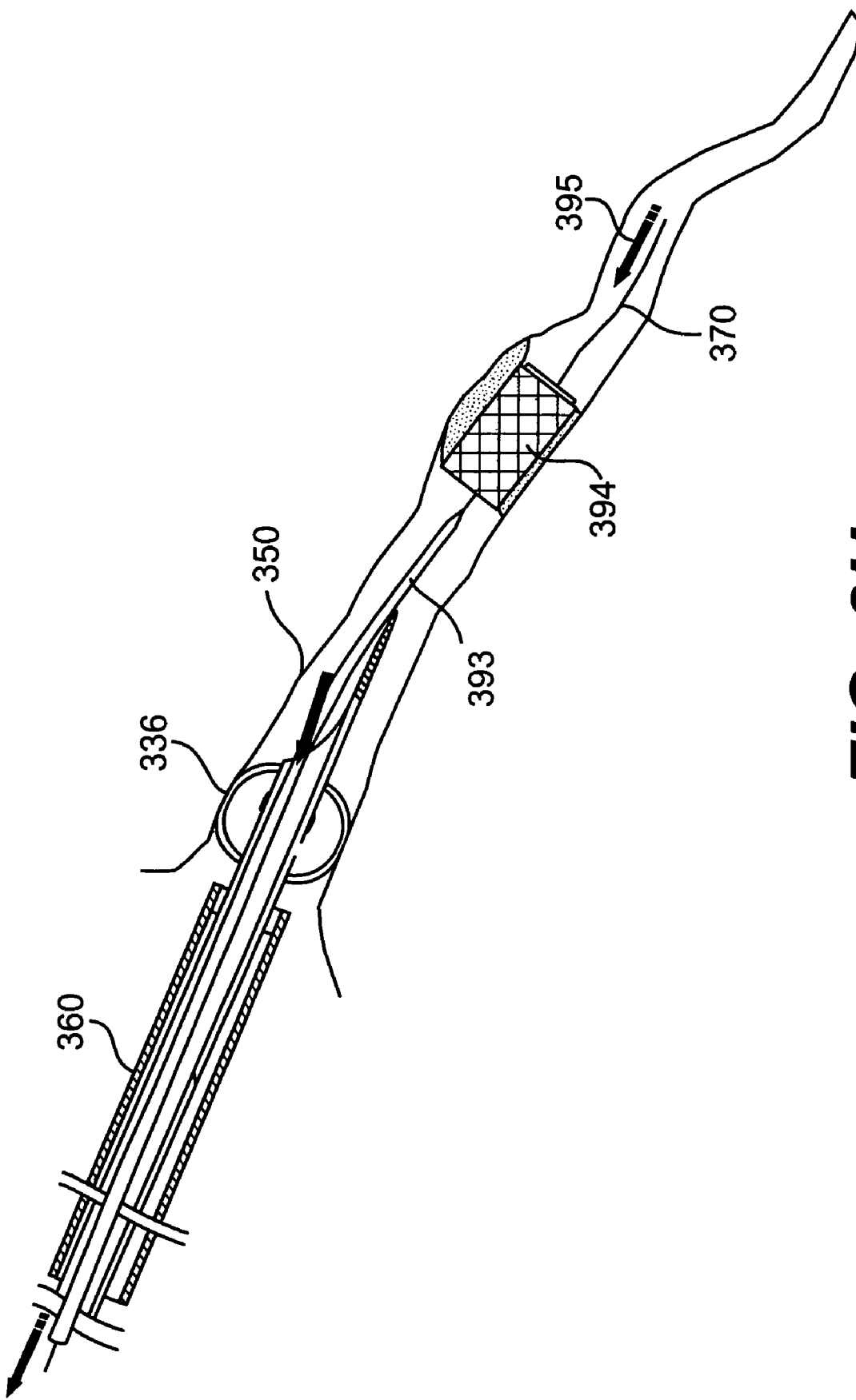
Figure 8I:
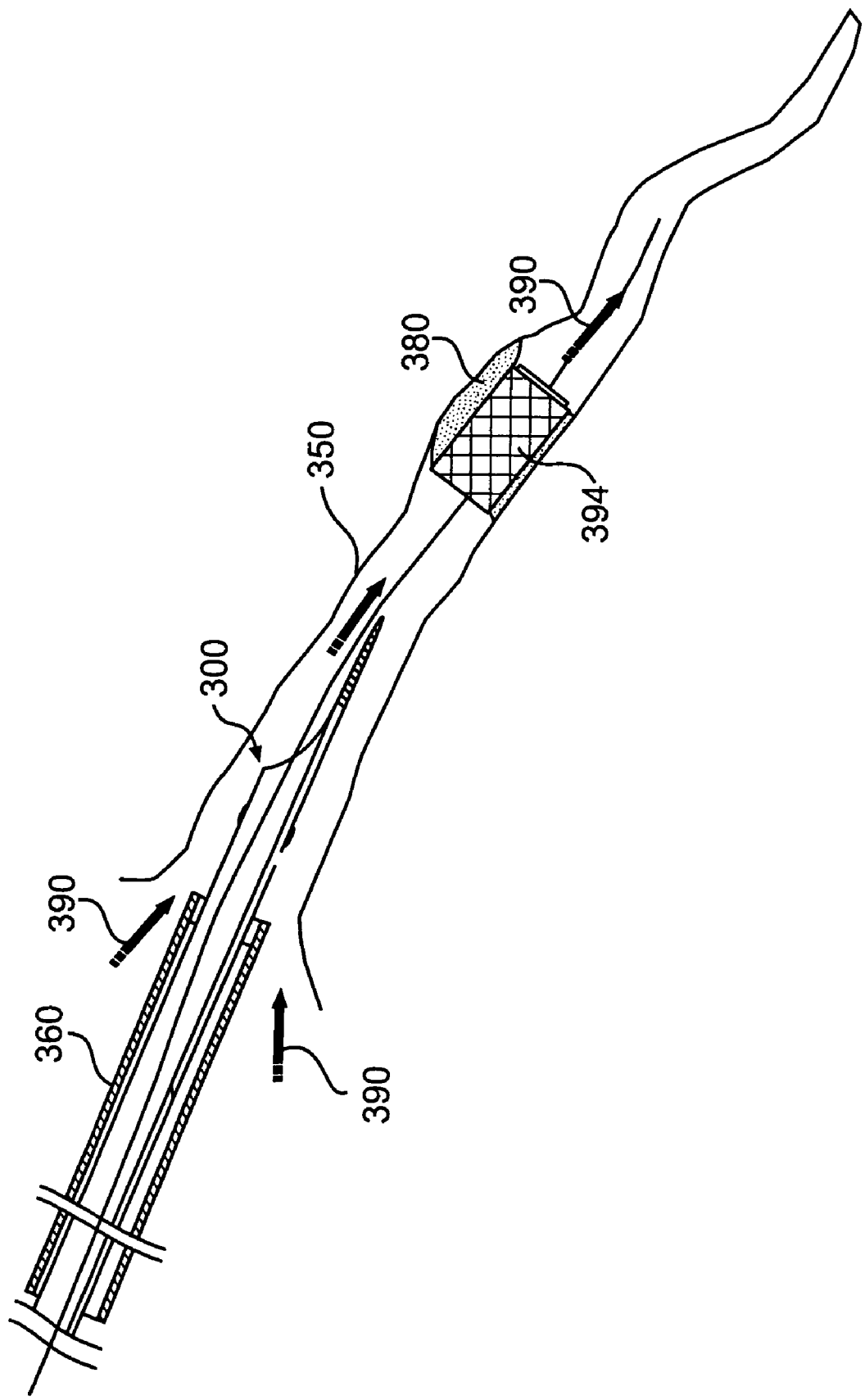

Thus, as shown in FIG. 8A, guide catheter 360 is positioned within blood vessel 350. Then evacuation sheath assembly 300 is advanced with guidewire 370 into blood vessel 350 (FIG. 8B). Proper positioning of a distal end of evacuation sheath assembly 300 may be confirmed using distal marker 346. Then distal sealing balloon 336 is inflated via inflation port 302, stopping blood flow within blood vessel 350. If desired, contrast dye may be injected through evacuation lumen 340 into blood vessel 350 to view blood vessel 350 prior to treating stenosis 380. Stenosis 380 is then treated and any embolic debris 397 is removed via retrograde flow 395 through evacuation lumen 340 (FIGS. 8C-8H), as previously described with respect to FIGS. 6C-6H. After treatment, distal sealing balloon 336 is deflated and evacuation sheath assembly 300 is removed from blood vessel 350 (FIG. 8I).

Figure 4B:
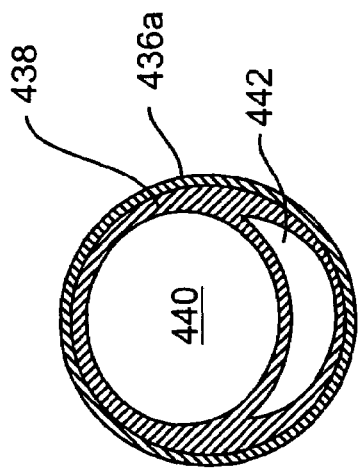
FIG. 4A is cross-sectional side view of a guiding catheter/evacuation sheath combination according to yet another embodiment of the present invention.

According to another aspect of the present invention, the evacuation sheath assembly may comprise an elongated multi-lumen tube which eliminates the need for a separate guiding catheter. As embodied herein and shown in FIGS. 4A and 4B, an evacuation/guiding sheath assembly 400 is provided with an evacuation/guiding lumen 440. Many of the elements present in the previous embodiments are also shown in FIGS. 4A and 4B and where these elements are substantially the same, similar reference numerals have been used and no detailed description of the element has been provided.

Figure 4A:
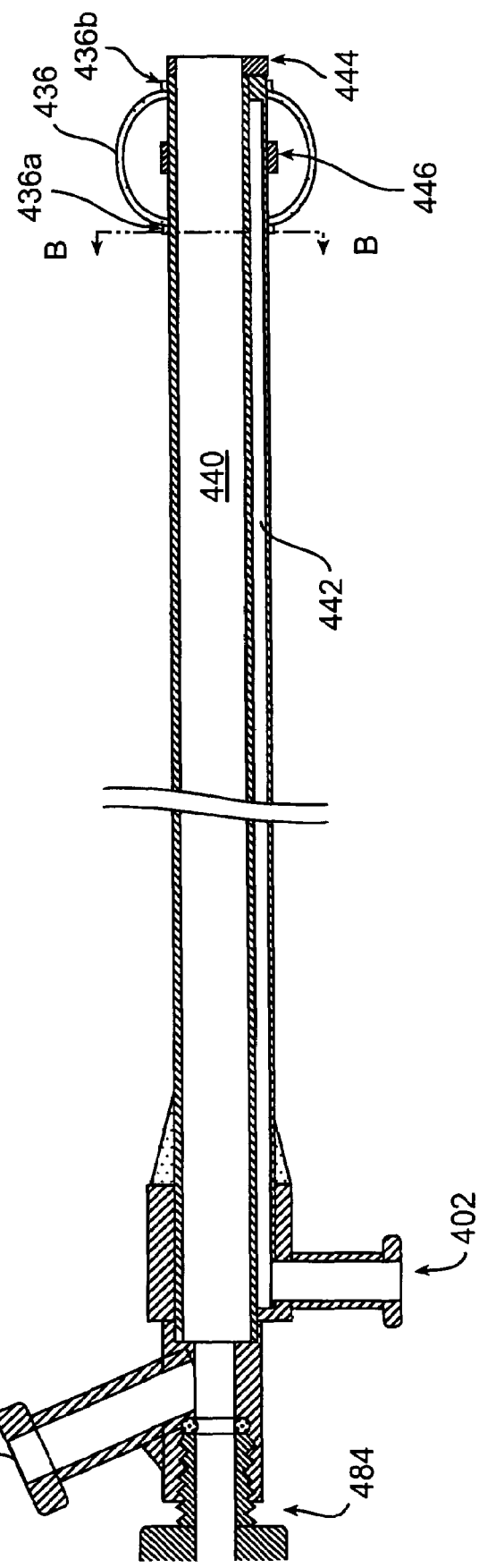

As shown in FIG. 4A, evacuation/guiding sheath assembly 400 includes a single elongated multi-lumen tube 438. The size of the tube 438 allows it to be used as a combination guiding catheter and evacuation lumen, to deliver interventional devices into a blood vessel 450. The multi-lumen tube 438 is preferably formed of a Pebax®, stainless steel and Teflon® composite material, very similar to conventional guide catheters, well known in the art, with the exception that an additional lumen in the wall of the tube is provided. Tube 438 can be made of other suitable polymers and metal materials. The multi-lumen tube 438 includes first and second lumens. The larger of the lumens, the evacuation/guiding lumen 440, is designed to allow for the passage of interventional devices such as, but not limited to, stent delivery systems and angioplasty catheters. The lumen 440 is also designed to allow for fluid flow, such as blood, blood/solid mixtures, radiographic dye and saline, within the lumen. This flow of fluid is allowed with or without an interventional device in the evacuation/guiding lumen 440.

The tube 438 can be pre-formed in various curvatures during manufacturing to allow for easy access to the ostium of several different blood vessels in a manner similar to conventional guide catheters as known in the art. Note that FIGS. 4A and 4B do not show these pre-formed curves. The distal end of the tube 438 is preferably fitted with a more flexible material, forming a soft distal tip 444. This flexible tip 444 allows the evacuation/guiding lumen 440 to be placed more smoothly into the blood vessel. The tube 438 also contains an inflation lumen 442, which allows for fluid communication between a proximal end of the evacuation/guiding sheath assembly 400 and an expandable sealing surface on a distal end of the evacuation/guiding sheath assembly 400.

Preferably, the expandable sealing surface is an inflatable sealing balloon 436. The sealing balloon 436 is preferably elastomeric and may comprise polyurethane or silicone, similar to that of the distal sealing balloon of FIGS. 1A-1C. The sealing balloon 436 is intended to be positioned distal of the ostium of the blood vessel 450 and inflated against the blood vessel 450 causing a fluid tight seal between the blood vessel 450 and the balloon 436. Radiopaque markers 446 are preferably placed at the site of the sealing balloon 436 to allow radiographically verifying the position of the sealing balloon 436. The proximal portion of the tube 438 is sealed against a interventional device by a bifurcated touhy borst valve 484 attached to the evacuation/guiding sheath assembly 400 to create a fluid tight seal against the evacuation/guiding sheath assembly 400 and the interventional device.

A proximal portion of the tube 338 is secured to the bifurcated touhy borst luer hub 484 by an overlapping weld or bond joint. The bifurcated luer hub allows the evacuation sheath assembly to be connected to an inflation apparatus and a vacuum source through an inflation port 402 and a vacuum port 403, respectively.

The steps of using evacuation/guiding sheath assembly 400 are sequentially depicted in simplified FIGS. 9A to 9H. Use of evacuation/guiding sheath assembly 400 is similar to the method described with respect to evacuation sheath assembly 100. The differences between the method discussed with respect to FIGS. 6A-6I and that for evacuation/guiding sheath assembly 400 are discussed below.

Figure 9A:
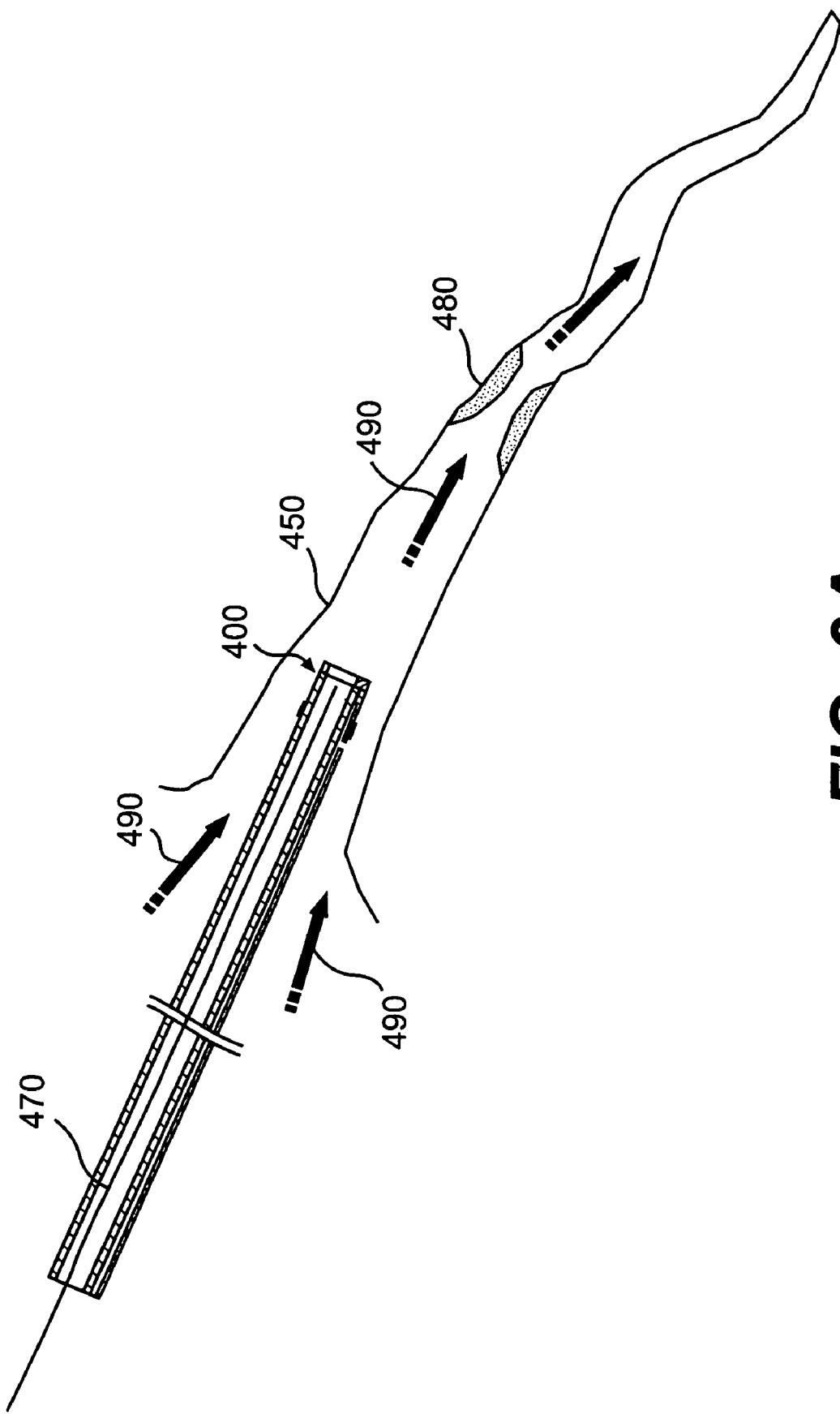
FIGS. 9A-9H are cross-sectional views of the guiding catheter/evacuation sheath of FIGS. 4A and 4B as employed in a method according to yet another aspect of the present invention.
Figure 9B:
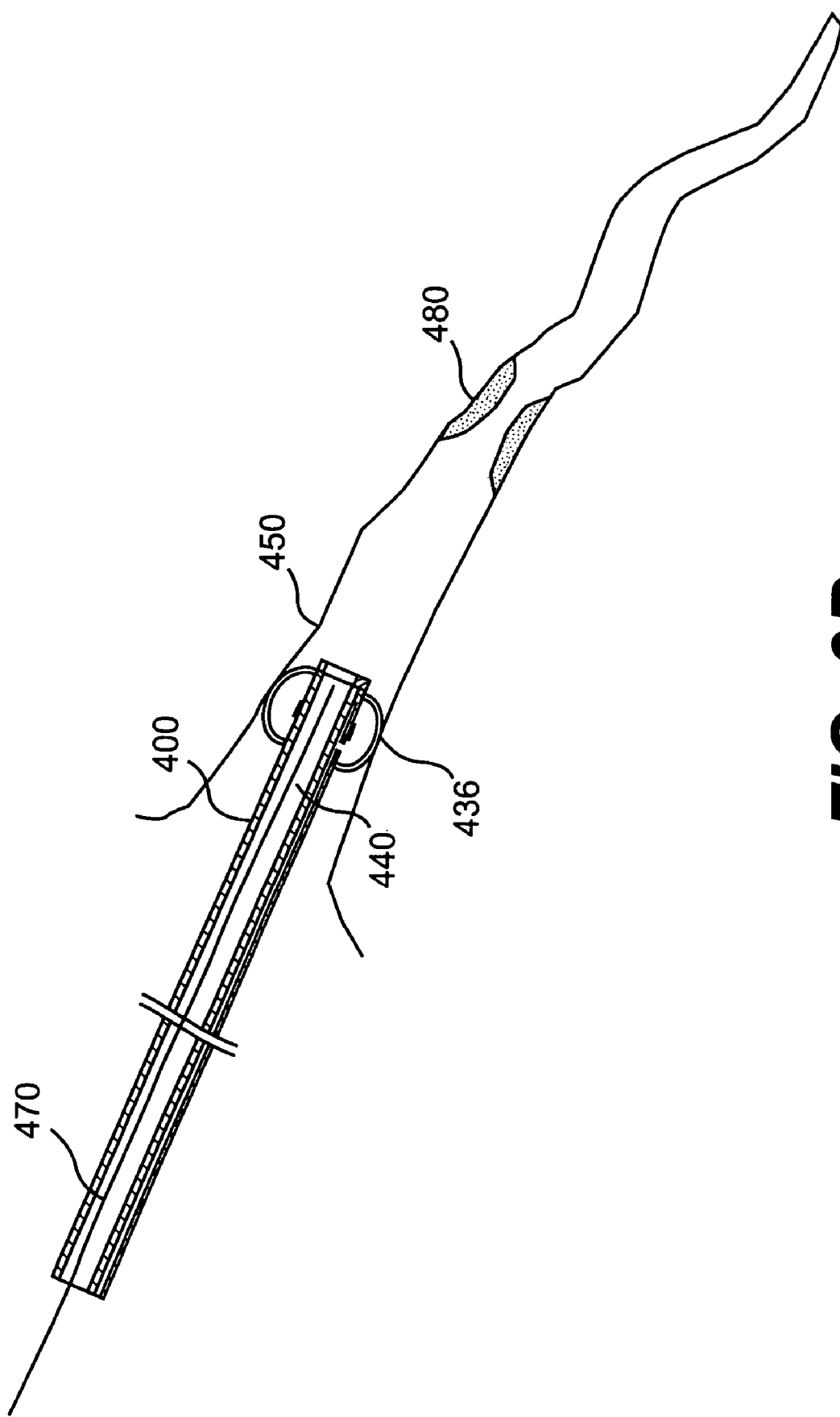
Figure 9C:
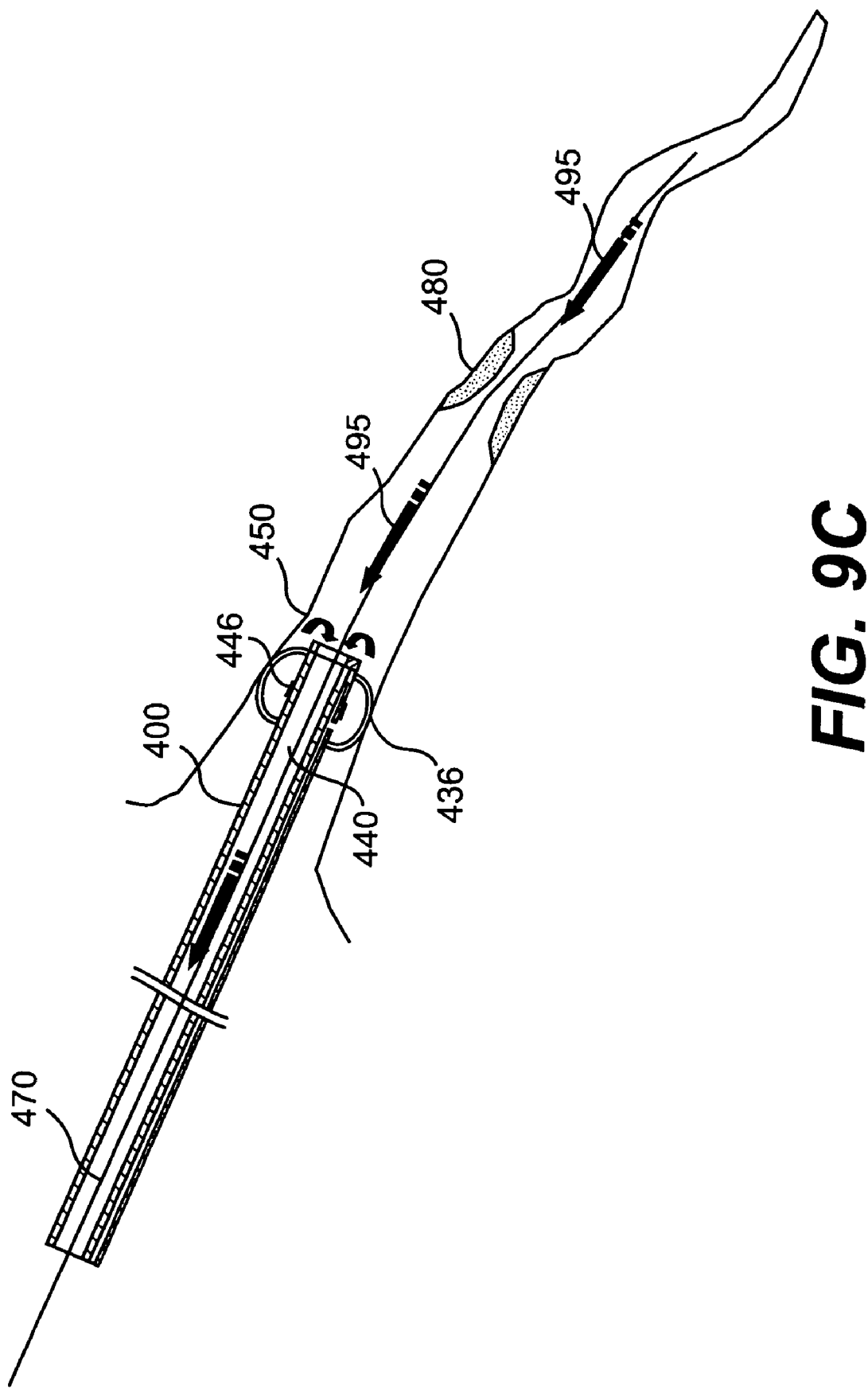
Figure 9D:
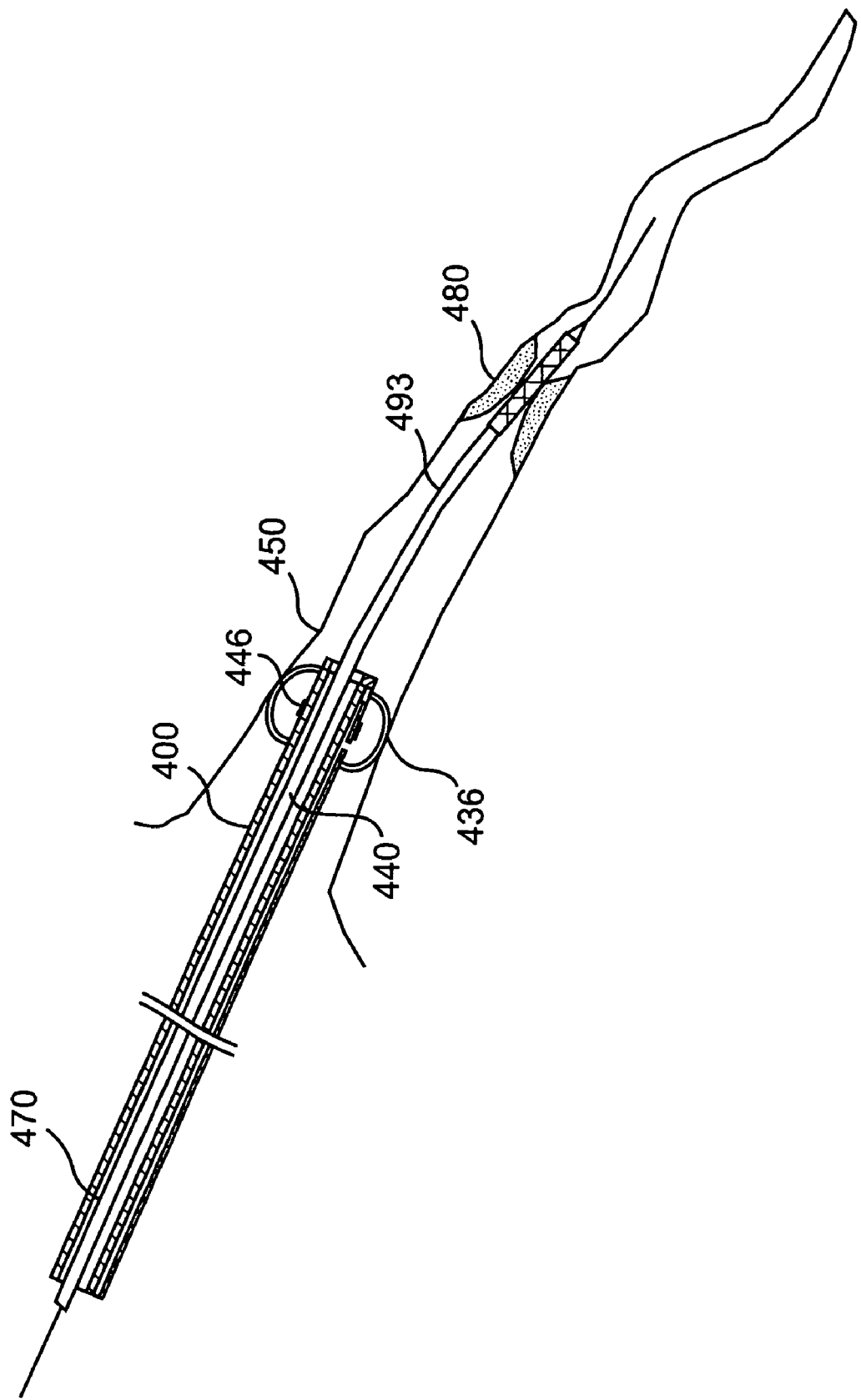
Figure 9E:
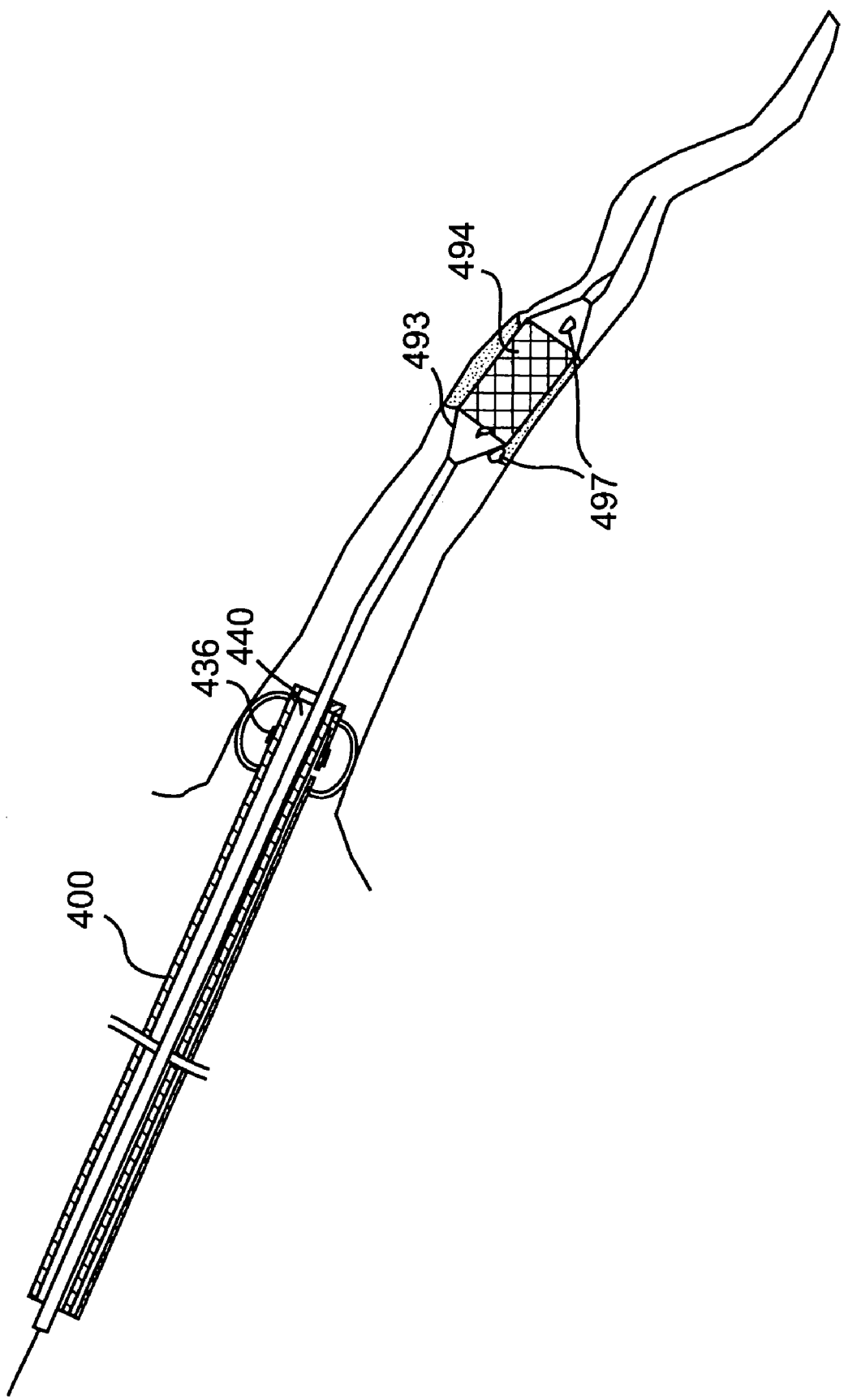
Figure 9F:
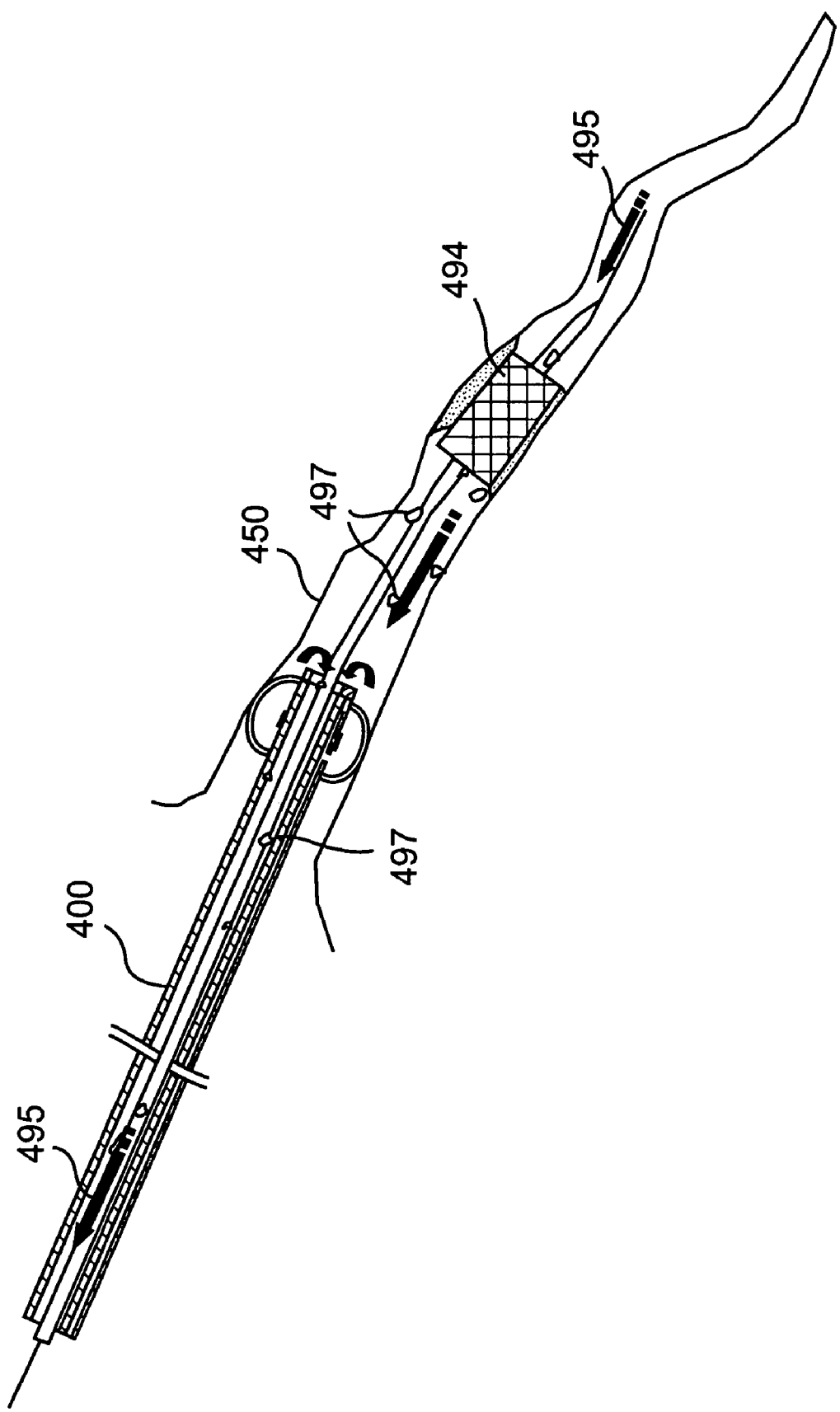
Figure 9G:
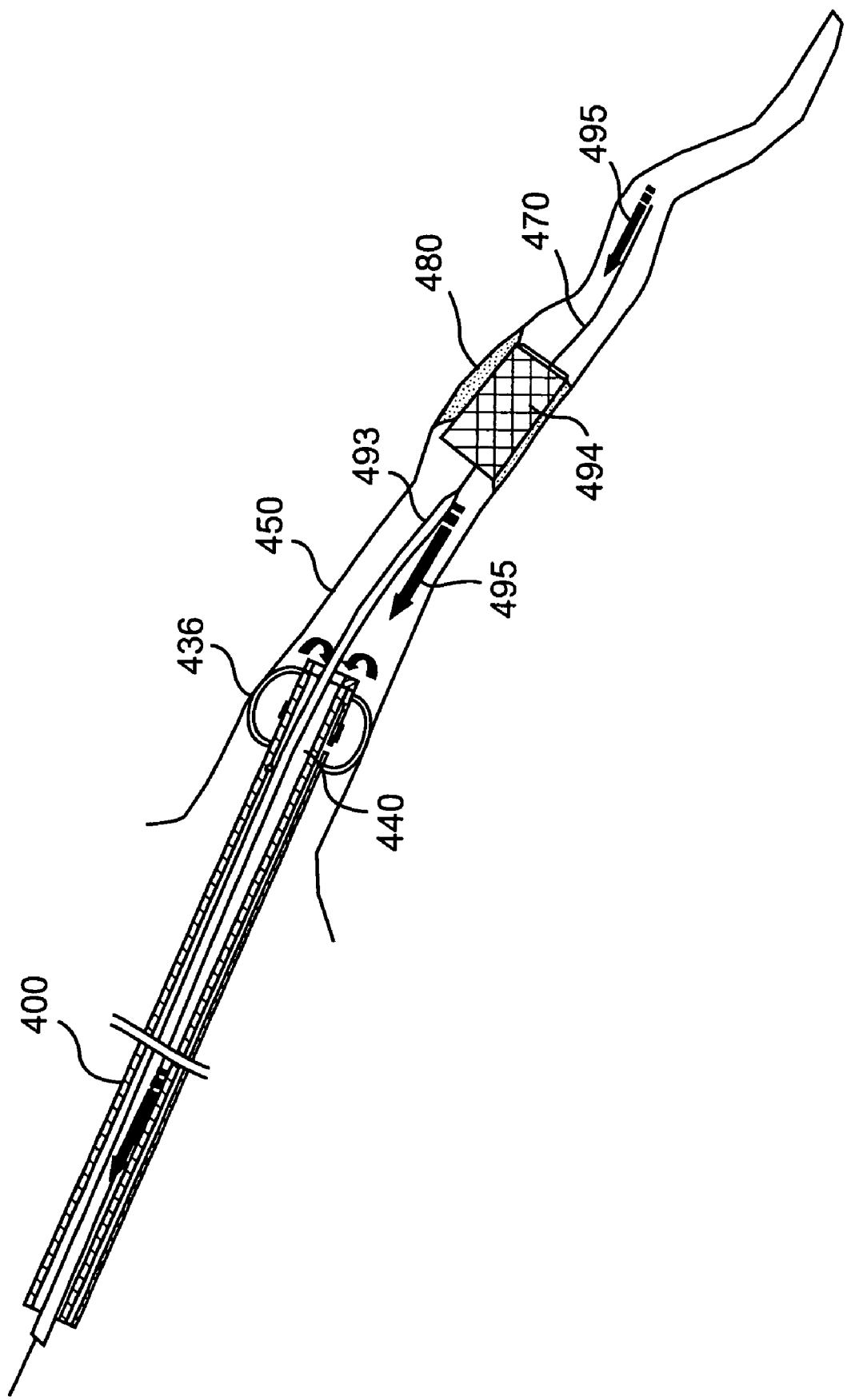

The lumen of the blood vessel 450 is accessed with the distal tip 444 of the evacuation/guiding sheath assembly 400. A guide wire 470 is advanced to a location just proximal to the distal tip 444 of the evacuation/guiding sheath assembly 400 (FIG. 9A). Blood flow at this point remains in the direction of normal arterial blood flow as shown by arrows 490. The evacuation/guiding sheath assembly 400 is then positioned with the distal marker band 446 distal of the ostium of the blood vessel 450. Once the positioning of the distal tip 444 of the evacuation/guiding sheath assembly 400 is verified, the distal sealing balloon 436 is inflated as shown in FIG. 9B to stop normal antegrade flow. The distal sealing balloon 436 provides a fluid tight seal between the sealing balloon 436 and the blood vessel 450. Alternatively, the distal sealing balloon 436 may be shaped such that it seals against the aortal surface and the most adjacent portion of the coronary ostium (not shown).

Figure 5D:
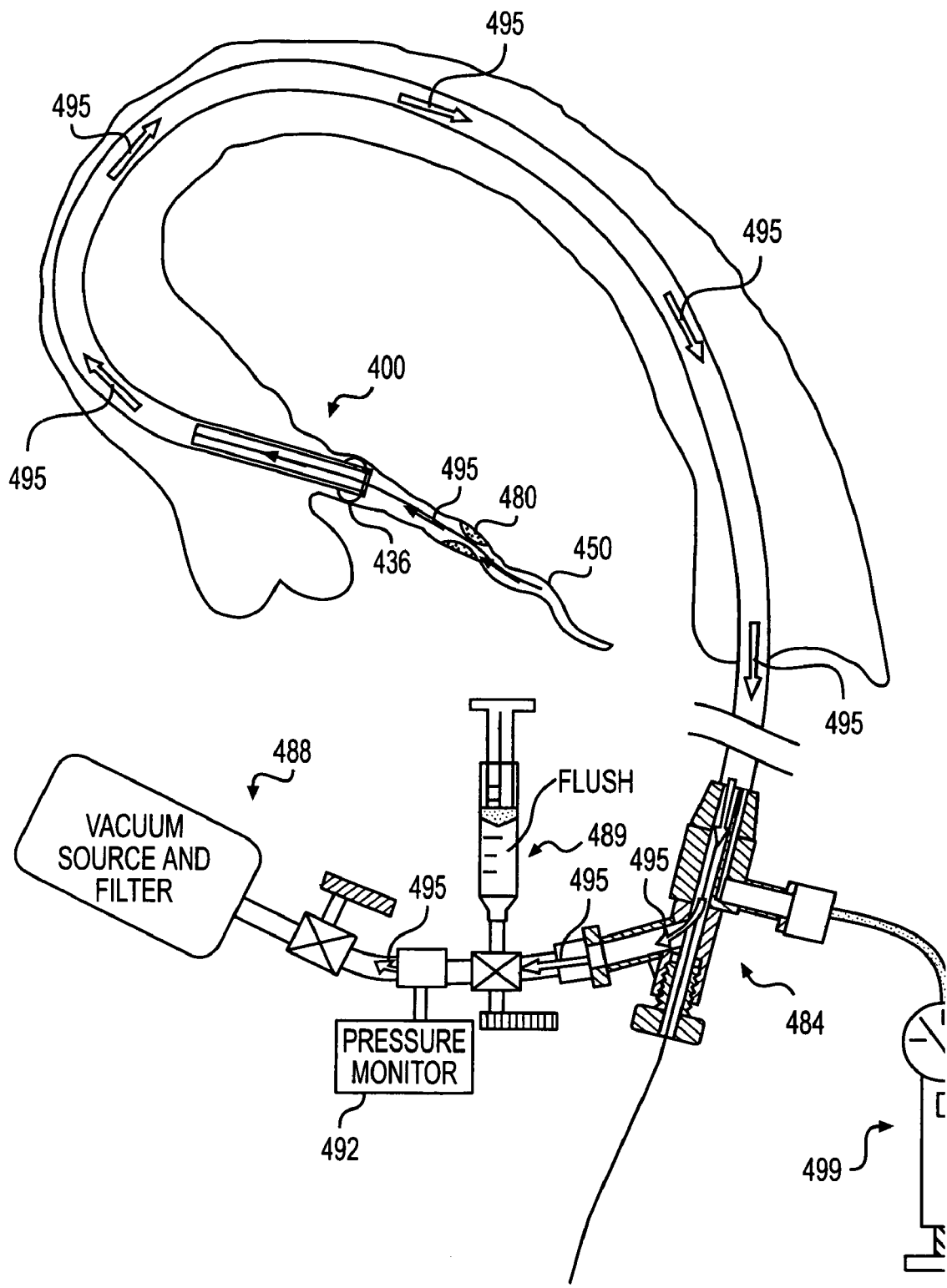
FIG. 5D is cross-sectional view of the guiding catheter/evacuation sheath combination of FIGS. 4A and 4B deployed within a vessel.

A touhy borst valve 484 attached to the evacuation/guiding sheath assembly 400 (shown in FIG. 5D) provides a fluid tight seal around the guide wire 470. The two fluid tight seals establish fluid communication between the distal end of the evacuation/guiding sheath assembly 400 and a fluid collection chamber, filter, and vacuum source 488, which is attached to the bifurcation lumen of the touhy borst valve 484 shown in FIG. 5D, and stop normal antegrade blood flow within blood vessel 450. A blood pressure transducer 492 is commonly connected in fluid communication with the lumen of the guide catheter to monitor arterial blood pressure.

Figure 9H:
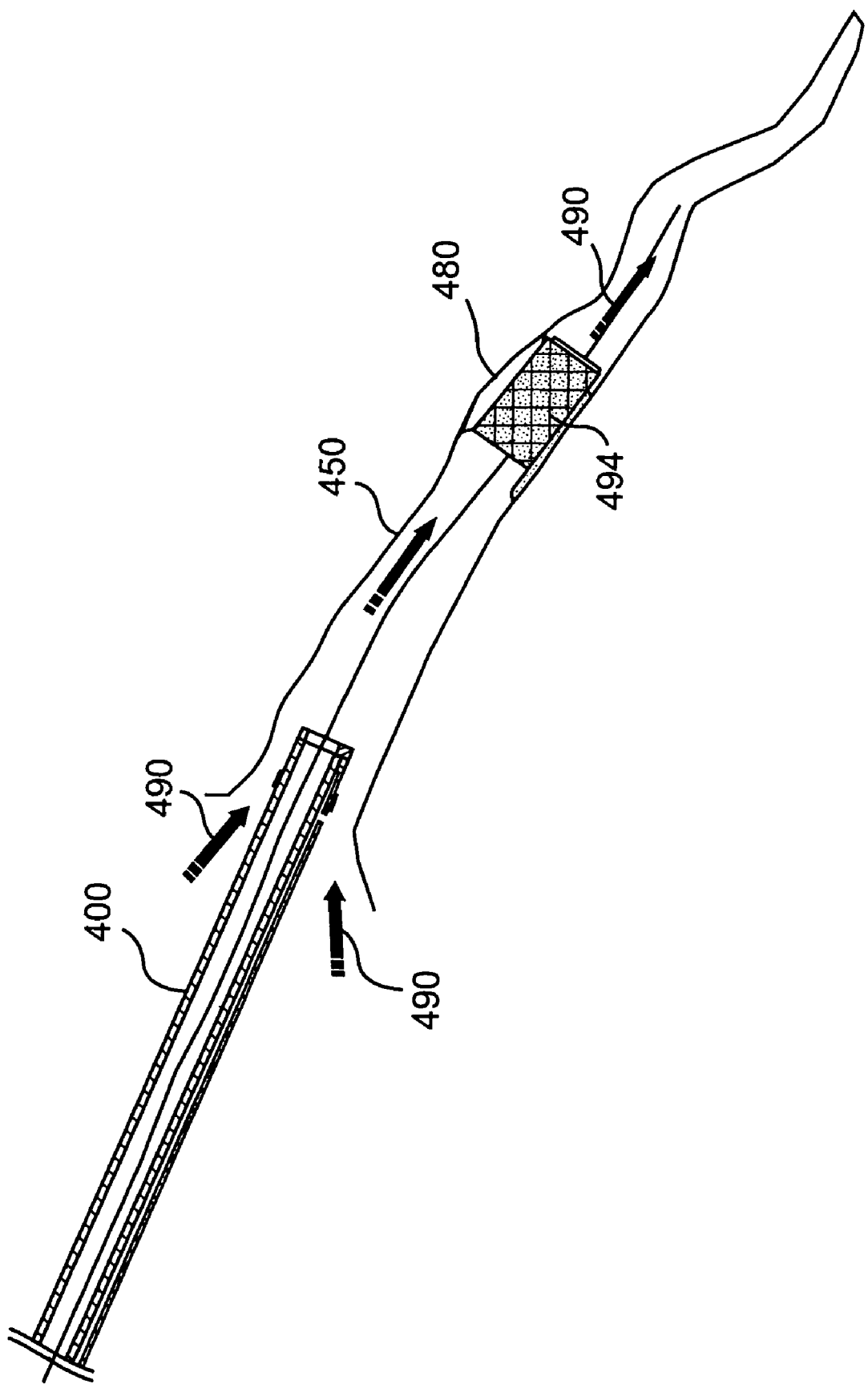

If desired, contra dye may be injected through evacuation/guiding lumen 440 into blood vessel 450 prior to treating stenosis 480. Stenosis 480 is then treated and any embolic debris 497 is removed via retrograde flow 495 through evacuation/guiding lumen 440 (FIGS. 9C-9G) as previously described with respect to FIGS. 6C-6H. After treatment, distal sealing balloon 436 is deflated and evacuation/guiding sheath assembly 400 is removed from blood vessel 450 (FIG. 9H).

According to another aspect of the present invention, the diameter of an evacuation head may be expandable from a first introduction diameter to a second operational diameter. As embodied herein and shown in FIGS. 10A-10D, an evacuation sheath assembly 500 is provided with an expandable evacuation head 532. Many of the elements present in the previous embodiment are also shown in FIGS. 10A-10D and where these elements are substantially the same, similar reference numerals have been used and no detailed description of the element has been provided.

The evacuation head 532 of the present embodiment is similar to the first and second embodiments previously discussed in that the evacuation sheath assembly 500 comprises a relatively short evacuation head 532. Evacuation sheath assembly 500 also makes use of the guide catheter 560 to form a part of an evacuation lumen 540.

Figure 10A:
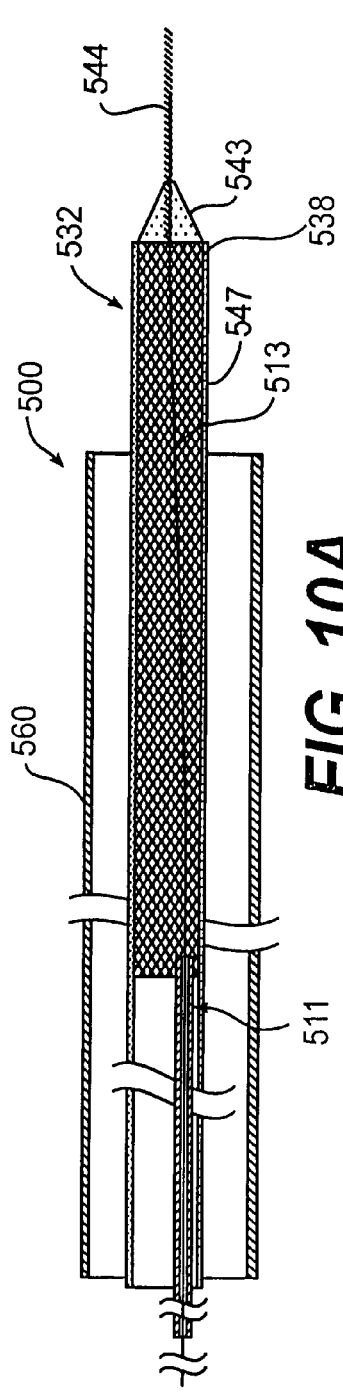
FIG. 10A is a cross-sectional side view of another embodiment of an evacuation sheath assembly enclosed in a delivery sheath and being delivered through a guiding catheter.
Figure 10B:
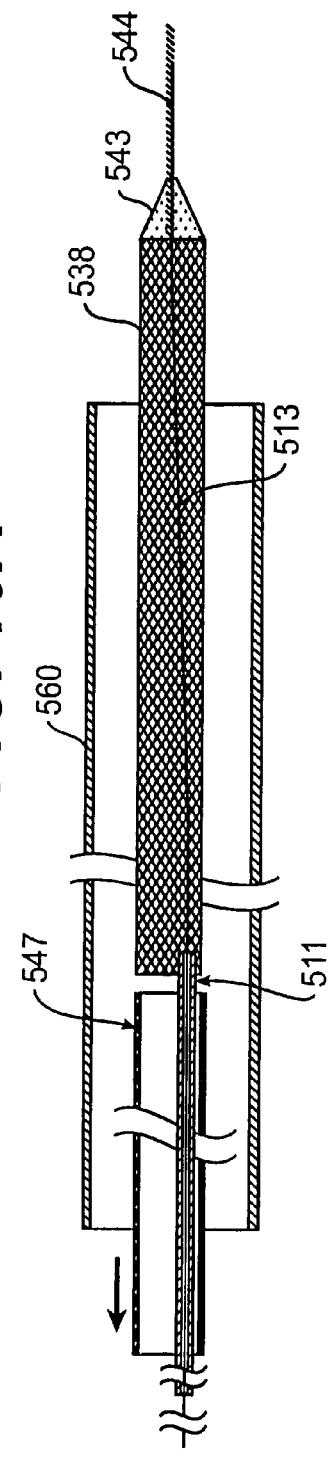
FIG. 10B is a cross-sectional side view of a braided sheath forming an evacuation head of the evacuation sheath assembly of FIG. 10A in an unexpanded state with the delivery sheath removed.

As shown in FIG. 10A, evacuation head 532 includes a tube 538 having a single expandable lumen, evacuation lumen 540. Evacuation head 532 may have a naturally unexpanded state. Alternatively, evacuation head 532 may be designed to normally be in an expanded state. However, it is preferred to have the evacuation head 532 fabricated to have its natural shape and size in the reduced dimension, as shown in FIG. 10B.

The evacuation head 532 includes two sealing surfaces 534, 536. A proximal sealing surface 534 is intended to seal against an inside distal portion of the guide catheter 560 and a distal sealing surface is intended to seal against the inside of the blood vessel 550, for example a coronary artery or an SVG. Although it is contemplated that the expandable evacuation head 532 could include two balloon-type seals, for example by adding a sealing balloon to each end of a tube 538 forming evacuation head 532, it is preferable to simply allow the outer surface of the expandable evacuation head 532 to create the sealing surfaces 534, 536.

Preferably, evacuation tube 538 is formed of a braided sheath and a coating or covering over the braided sheath. The braided sheath itself can be made of stainless steel (full hard or spring), Eligiloy™, nickel titanium alloy or other metals or polymers with high elasticity characteristics. Preferably the braided sheath which forms tube 538 has a length of between about 3 cm and about 20 cm.

The braided sheath can be coated with a polymer such as polyurethane, silicone and other similar elastomeric materials that can stretch and allow the braided sheath to expand. The covering or coating is preferably a thin and flexible elastomer, which is dip coated on the braided sheath. Since the elastomeric covering or coating is applied to the braided sheath in its reduced dimension, the covering or coating helps to retain the braided sheath in its reduced dimension.

Alternatively, the braided sheath can be fitted with a fluid tight woven material that has similar expansion qualities as the braided sheath. If the covering is a braided fabric, it is preferably made from polyester or other high strength polymer yarn.

Alternatively, the covering may be formed of a spun fibers laid down in multiple layers back and forth along the length of the braided sheath. If the fiber layers are laid down at the same helical angle as the primary braided sheath, the covering will behave similarly to the primary braided sheath upon expansion, requiring little or no expansile force to expand the covering from its reduced dimension to its expanded dimension. Each fiber layer will be made of several adjacent fiber windings to create a dense layer. Preferably, there are multiple layers, which together will be relatively impervious to fluid flow, thereby allowing sealing surfaces of the evacuation head 532 to effectively isolate fluid communication from the lumen of the guide catheter with the lumen of the blood vessel.

The braided sheath is preferably fabricated at its desired reduced diameter, for example, as utilized in an SVG with an 8 French guide catheter, about 0.4-1.5 mm. The braided sheath is then coated or covered at this reduced size. The braided sheath which comprises the evacuation head 532 is preferably connected to an actuation wire 513 by a few of the filaments near the distal end of the braided sheath. A proximal hollow shaft 511 is connected to a few of the braid filaments near a proximal end of the evacuation head 532 and serves as an anchor point. Actuation wire 513 sits within the hollow shaft 511 and the braided sheath is preferably bonded or welded to the proximal hollow shaft 511 at the proximal end of the braided sheath and to the actuation wire 513 on the distal end of the braided sheath. The bonds attach in a manner that does not considerably impede the free movement of the braided sheath during expansion and contraction.

The proximal hollow shaft 511 is a tube, which preferably decreases in stiffness from a proximal end to a distal end thereof. The proximal hollow shaft 511 can be made of stainless steel hypotubing, polyethylene, or a composite of polymers and metal.

Preferably, the evacuation head 532 includes a steerable spring tip 544 extending from the actuation wire 513. Surrounding a portion of the spring tip 544 is a nose cone 543. The nose cone 543 serves as a tapering transition between the spring tip 544 and a distal end of a delivery sheath 547. The nose cone 543 facilitates smooth advancement of the evacuation sheath assembly through a guide catheter 560 and into the blood vessel 550.

The delivery sheath 547 preferably comprises a tube which covers the entire length of the reduced dimension of the evacuation head 532. The delivery sheath 547 is connected to a wire shaft (not shown), which emerges from a proximal end of the guide catheter 560. During evacuation, the delivery sheath 547 may be fully removed from the lumen of the guide catheter 560, or can be left in position within the guide catheter 560.

If the delivery sheath 547 is intended to be removed completely from the guide catheter 560, it may include a perforated longitudinal line to allow for splitting of the delivery sheath 547 and removal of the delivery sheath 547 from the proximal hollow shaft 511 of the evacuation sheath assembly 500.

Figure 10C:
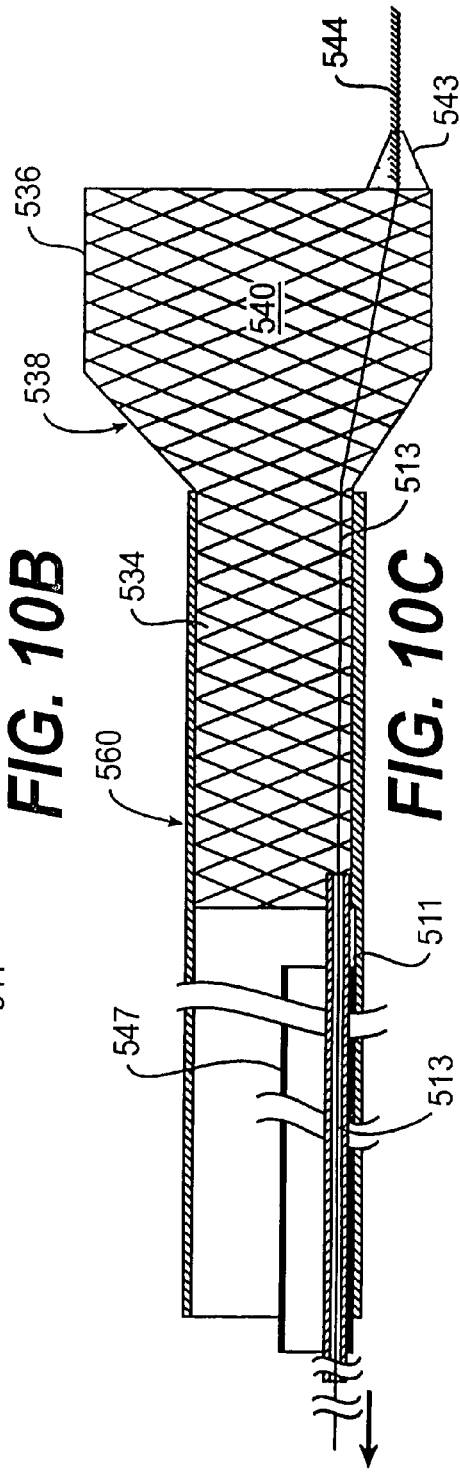
FIG. 10C is a cross-sectional side view of the braided sheath of FIG. 10B in the expanded state.

Alternatively, if the braided sheath has an expanded natural shape and size as shown in FIG. 10C, thereby being self-expanding upon removal of the delivery sheath 547, the delivery sheath 547 would preferably be usable during contracting and removal of the braided sheath. Thus, the delivery sheath 647 could be re-advanced to cover and constrain the braided sheath once the procedure is completed. In this manner, the evacuation sheath assembly 500 could be removed from the guide catheter 560.

The proximal end of the evacuation sheath assembly 500 may have an adjustable lock to anchor the actuation wire 513 to the proximal hollow shaft 511, allowing them to be held fixed to one another. This allows the braided sheath to be locked into a set position.

Figure 10D:
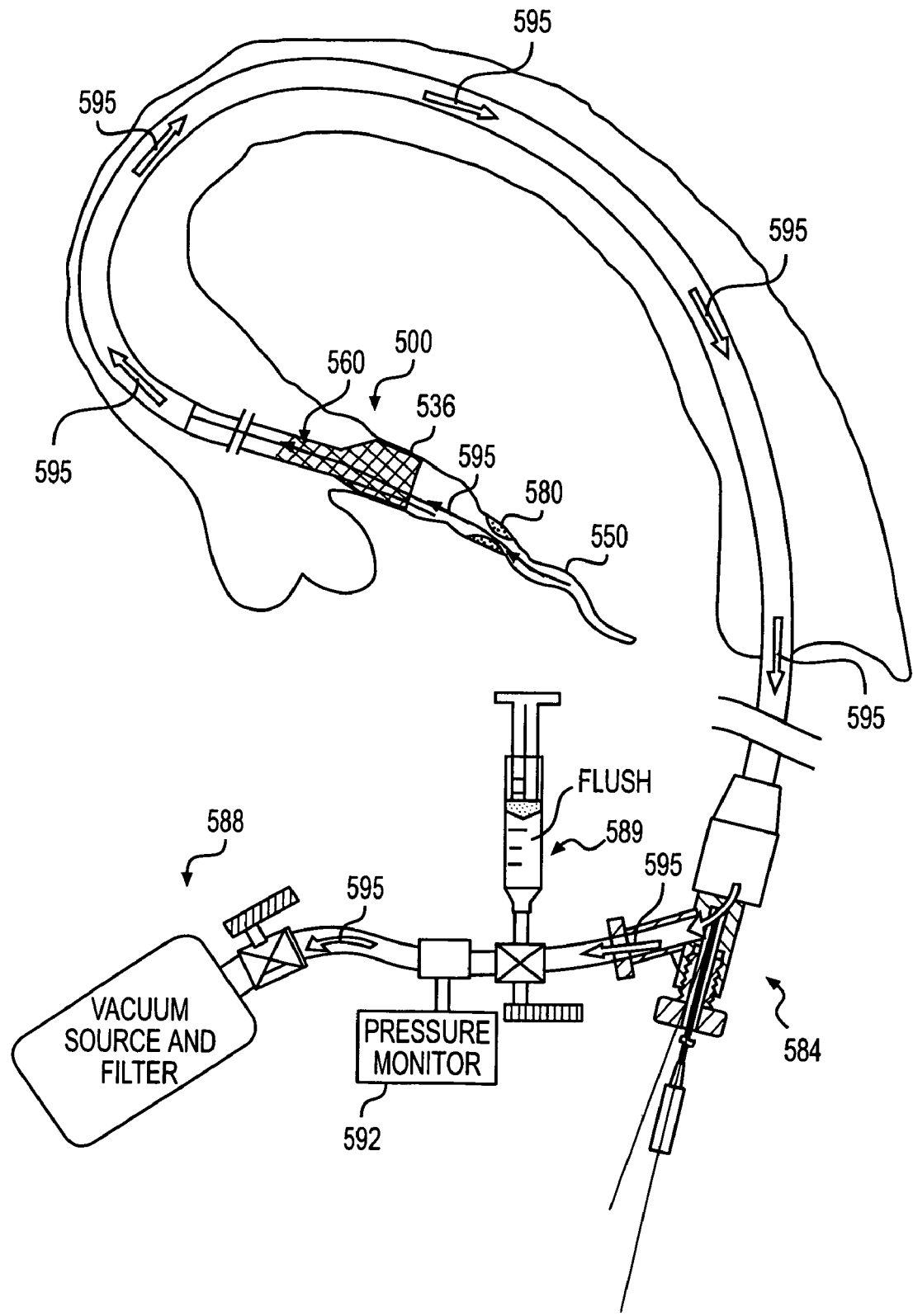
FIG. 10D is cross-sectional view of the guiding/evacuation lumen of the evacuation sheath assembly of FIGS. 10A-10C deployed within a blood vessel.

The evacuation sheath assembly 500, in use, is depicted in FIG. 10D. Use of evacuation sheath assembly 500 is similar to the method described with respect to evacuation sheath assembly 100. The differences between the method discussed with respect to FIGS. 6A-6I (evacuation sheath assembly 100) and that for evacuation sheath assembly 500 are discussed below.

In use, a guide catheter 560 is advanced into blood vessel lumen 550 over a guidewire 570. Evacuation sheath assembly 500, in a compressed state having a reduced diameter and enclosed in delivery sheath 547, is advanced through the lumen of guide catheter 560 over guidewire 570 and part way into blood vessel 550. Proper positioning of a distal end of evacuation sheath assembly 500 is confirmed using, for example, marker 545, nose cone 543, or by viewing the braided sheath through imaging.

After the positioning is verified, the delivery sheath 547 is removed from the evacuation head 532. The actuation wire 513 is then pulled proximally while the proximal hollow shaft 511 is held stationary, preferably by a valve. Pulling, the actuation wire 513 proximally longitudinally compresses the braided sheath forming evacuation lumen 540, causing it to expand in diameter. The evacuation lumen 540 expands and the proximal sealing surface 534 of the evacuation head 532 seals against the inside surface of the guide catheter 560. The portion of the evacuation lumen 540 extending beyond the guide catheter 560 and into the blood vessel 550 continues to expand until the distal sealing surface 536 of the evacuation head 532 seals against the inside surface of the blood vessel 550. Similar to previous embodiments, the expansion can be observed with fluoroscopy, and the blood pressure can be monitored 592 until the waveform changes from pulsatile arterial pressure to a venous pressure (again, in the example of a coronary or SVG blood vessel).

With both seals in place, normal blood flow is stopped. If desired, contrast dye may be injected through the catheter lumen into blood vessel 550 to view blood vessel 550 prior to treating stenosis 580. Stenosis 580 is then treated and any embolic debris is removed via retrograde flow 590 (FIG. 10D) as previously described with respect to FIGS. 6C-6H. After treatment, the actuation wire 513 is re-advanced to allow the braided sheath to contract and be maintained in its reduced dimension prior to withdrawing the evacuation sheath assembly 500 from blood vessel 550.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An evacuation sheath assembly, comprising:
   a multi-lumen tube having a proximal end, a distal end, a proximal opening, a distal opening, a central longitudinal axis, first and second lumens, and first and second sealing surfaces, the first lumen defined by a first wall of the multi-lumen tube, wherein the first wall is an integral part of the multi-lumen tube, wherein the first lumen is an evacuation lumen configured to be placed in fluid communication with a bloodstream and is sized to accept a therapeutic catheter, wherein the second lumen is an inflation lumen in fluid communication with at least one of the first and second sealing surfaces, wherein the first and second sealing surfaces are mounted on the multi-lumen tube and, upon inflation, define an arc that extends 360° around an outer surface of the multi-lumen tube, wherein at least one of the first and second sealing surfaces is adapted to form a fluid tight seal between the sealing surface and a blood vessel, wherein the evacuation lumen extends along an axis substantially parallel to the longitudinal axis of the multi-lumen tube, and wherein the proximal end has a generally circular edge that defines a first plane, the distal end has a generally circular edge that defines a second plane, the proximal and distal openings are arranged so that the first and second planes intersect the central longitudinal axis of the multi-lumen tube and at least one of the first and second planes forms an acute angle relative to the longitudinal axis of the multi-lumen tube; and a shaft in fluid communication with the inflation lumen of the multi-lumen tube and configured to connect to an inflation source, the shaft having a proximal end, a proximal region, a distal end, and a distal region, the multi-lumen tube being positioned on not more than the distal region of the shaft, wherein the multi-lumen tube has a first diameter and the shaft has a second diameter different from the first diameter.

2. The assembly of claim 1, wherein the first and second sealing surfaces are balloons.

3. The assembly of claim 1, wherein the first and second sealing surfaces are elastomeric.

4. The assembly of claim 1, wherein the first sealing surface is located on a proximal portion of the multi-lumen tube and the second sealing surface is located on a distal portion of the multi-lumen tube.

5. The assembly of claim 4, wherein the second sealing surface is expandable to a greater diameter than the first sealing surface.

6. The assembly of claim 1, wherein the evacuation lumen is configured to expand from a delivery configuration to an evacuation configuration.

7. The assembly of claim 1, wherein the multi-lumen tube includes an inner layer and an outer layer.

8. The assembly of claim 7, wherein the outer layer forms the sealing surfaces.

9. The assembly of claim 7, wherein the inner layer forms the evacuation lumen.

10. The assembly of claim 7, wherein the inner layer comprises a first material and the outer layer comprises a second, different material.

11. The assembly of claim 10, wherein the second material is an expandable material.

12. The assembly of claim 1, wherein the evacuation lumen is shorter than the inflation lumen.

13. The assembly of claim 1, wherein the first diameter is larger than the second diameter.

14. The assembly of claim 1, wherein the proximal opening is angled.

15. The assembly of claim 1, wherein the distal opening is angled.

* * * * *